US006447767B1

(12) United States Patent
Slavin et al.

(10) Patent No.: US 6,447,767 B1
(45) Date of Patent: Sep. 10, 2002

(54) NON-MYELOABLATIVE TOLEROGENIC TREATMENT

(75) Inventors: Shimon Slavin, Jerusalem; Tatyana Prigozhina, Rehovot, both of (IL)

(73) Assignee: Hadasit Medical Research Services and Development Ltd., Jerusalem (IL)

(*) Notice: Subject to any disclaimer, the term of this patent is extended or adjusted under 35 U.S.C. 154(b) by 0 days.

(21) Appl. No.: 09/506,082

(22) Filed: Feb. 16, 2000

Related U.S. Application Data

(63) Continuation-in-part of application No. 09/222,011, filed on Dec. 31, 1998, which is a continuation-in-part of application No. 08/862,550, filed on May 23, 1997, now abandoned.

(51) Int. Cl.[7] .......................... A61K 38/00; A61K 48/00; C12N 15/85
(52) U.S. Cl. .................. 424/93.1; 424/93.21; 514/2; 514/44; 435/325
(58) Field of Search .............................. 424/93.21, 93.1; 514/2, 44

(56) References Cited

U.S. PATENT DOCUMENTS

| | | | |
|---|---|---|---|
| 5,273,738 A | 12/1993 | Matthews et al. | ......... 424/1.49 |
| 5,514,364 A | 5/1996 | Ildstad | ........................ 424/1.49 |
| 5,635,156 A | 6/1997 | Idstad | ......................... 424/1.49 |

FOREIGN PATENT DOCUMENTS

| | | |
|---|---|---|
| WO | WO 93/13785 | 7/1993 |
| WO | WO 94/09803 | 5/1994 |
| WO | WO 95/03062 | 2/1995 |
| WO | WO 96/37208 | 11/1996 |
| WO | WO 96/38178 | 12/1996 |

OTHER PUBLICATIONS

Bacher–Lustig et al., "Megadose of T cell–depleted bone marrow overcomes MHC barriers in sublethally irradiated mice," *Nature Medicine*, 1(12):1268–1273 (1995).
Bacher–Lustig et al., "Megadose of T cell–depleted bone marrow overcomes MHC barriers in sublethally irradiated mice," *Chemical Abstracts*, Abst. No. 80953e, 124(7):670 (1996).
Boyer et al., "The Role of B7 Costimulation by Murine Acute Myeloid Leukemia in the Generation and Function of a CD8+ T–Cell Line . . . Properties," *Blood*, 89(9):3477–3485 (1997).
Colson et al., "A Nonlethal Conditioning Approach to Achieve Durable Multilineage Mixed Chimerism and Tolerance Across Major . . . Barriers," *J. Immunology*, 155:4179–4188 (1995).
Eto et al., "Prolongation of Kidney Graft Survival by Cyclophosphamide–Induced Tolerance in Rats," *J. Urology*, 153:1693–1696 (1995).
Field et al., "Alloantigen Priming After Total Lymphoid Irradiation Alters Alloimmune Cytokine Responses," *Transplantation*, 60(7):695–702 (1995).

Goss et al., "Induction of Allogeneic Islet Survival by Intrahepatic Islet Preimmunization and Transient Immunosuppression," *Diabetes*, 45:144–147 (1996).
Greenstein et al., "The use of tolerance for transplantation across xenogenic barriers," *Nature Biotechnology*, 15:235–238 (1997).
Kawai et al., "Mixed Allogeneic Chimerism and Renal . . . Monkeys," *Transplantation*, 59(2):256–262 (1995).
Knobler et al., "Tolerance to Donor–Type Skin in the Recipient of a Bone Marrow Allograft," *Transplantation*, 40(2):223–225 (1985).
Korngold et al., "Graft–Versus–Myeloid Leukemia Responses Following Syngeneic and Allogeneic Bone Marrow Transplantation," *Transplantation*, 58(3):278–287 (1994).
Kwak et al., "Transfer of myeloma idiotype–specific immunity from an actively immunised marrow donor," *Lancet*, 345:1016–1020 (1995).
Latinne et al., "Tolerance to Discordant Xenografts," *Transplantation*, 57(2):238–245 (1994).
Lee et al., "Mechanism of Tolerance in Mixed Xenogeneic Chimeras Prepared With a Nonmyeloablative Conditioning Regimen," *Transplantation Proceedings*, 26(3):1197–1198 (1994).
Maeda et al., "Role of Peripheral Hemopoietic Chimerism in Achieving Donor–Specific tolerance in Adult Mice," *J. Immunology*, 150(3):753–762 (1993).
Marquet and Heystek, "The Induction and Abolition of Specific Immunosupression of Heart Allografts in Rats by Use of Donor Blood and Cyclophosphamide," *J. Immunology*, 115(3):405–408 (1975).
Mayumi et al., "Drug–Induced Tolerance to Allografts in Mice," *Transplantation*, 40(2):188–194 (1985).
Mayumi et al., "Long–Lasting Skin Allograft Tolerance in Adult Mice Induced Acress Fully Allogeneic . . . Using Cyclophosphamide," *J. Exp. Med.*, 169:213–238 (1989).

(List continued on next page.)

*Primary Examiner*—Robert A. Schwartzman
*Assistant Examiner*—Anne Marie Beckerleg
(74) *Attorney, Agent, or Firm*—Townsend and Townsend and Crew LLP

(57) ABSTRACT

The present invention features a method of inducing donor-specific tolerance in a host. Tolerogenic treatments of the present invention may be administered to a host prior to transplantation of donor-derived materials. The tolerogenic treatment involves (1) administering an immunosuppressive agent to a host mammal in a non-myeloablative regimen sufficient to decrease, but not necessarily to eliminate, the host mammal's functional T lymphocyte population; (2) infusing donor antigens from a non-syngeneic donor into the host mammal; (3) eliminating those host T lymphocytes responding to the infused donor antigens using a non-myeloablative dose of lymphocytotoxic or tolerizing agent; and (4) administering donor hematopoietic cells to the host mammal. Donor lymphoid cells used for cell therapy of a host mammal can be depleted of host specific immunological reactivity by methods essentially similar to those use for tolerizing a host mammal prior to transplantation.

16 Claims, 21 Drawing Sheets

OTHER PUBLICATIONS

Mayumi et al., "The Necessity of Both Allogeneic Antigens and Stem Cells for Cyclophosphamide–Induced Skin Allograft Tolerance in Mice," *Immunobiology*, 178:287–304 (1989).

Morecki et al., "Alloantigen Persistence in Induction and Maintenance of Transplantation Tolerance," *J. Exp. Med.*, 165:1468–1480 (1987).

Myburgh et al., "Transplantation tolerance in Primates Following Total Lymphoid Irradiation and Allogeneic Bone Marrow Injection, I. Orthotopic Liver Allografts," *Transplantation*, 29(5):401–404 (1980).

Myburgh et al., "Transplantation tolerance in Primates Following Total Lymphoid Irradiation and Allogeneic Bone Marrow Injection, II. Renal Allografts," *Transplantation*, 29(5):405–408 (1980).

Parkman et al., "Immunological reconstruction following bone marrow transplantation," *Immun. Reviews*, 157:73–78 (1997).

Pixley et al., "Transplantation in utero of Fetal Human Hematopoietic Stem Cells into Mice Results in Hematopoietic Chimerism," *Pathobiology*, 62:238–244 (1994).

Pugatsch et al., "Minimal Residual Disease in Murine B–Cell Leukemia (BCL1) Detected by PCR," *Leukemia Res.*, 17(11):999–1002 (1993).

Ran, Xinze et al., "Effects of blood transfusion on bone marrow transplantation for the survival of rats after total Lymphoid . . . cyclophosphamide," *Chemical Abstracts*, Abst. No. 141429d, 126(11):251 (1997).

Reisner et al., "Bone marrow transplantation across HLA barriers by increasing the number of transplanted cells," *Immunology Today*, 16(9):437–440 (1995).

Sachs, "Transplantation Tolerance," *Ann. Thorac. Surg.*, 56:1221–1227 (1993).

Scheding et al., "Transplantation of ex–vivo expanded peripheral blood progenitor cells . . . patients," *Chemical Abstracts*, Abst. No. 325042d, 126(25):44 (1997).

Shapira–Nahor et al., "Human T Cells Recovered from Human/Balb Radiation Chimeras Are Hypersensitive to Human Immunodeficiency Virus Type 1 Infection," *J. Virology*, 71(5):1–6 (1997).

Sharabi et al., "Mixed allogenic chimeras prepared by a non–myeloablative regimen: requirement for chimerism to maintain tolerance," *Bone Marrow Transplantation*, 9:191–197 (1992).

Sikes, "Xenogeneic Tolerance," Abstract in program for IBC's Second Bi–Annual Symposium on Xenotransplantation, (Oct. 1–2, 1996), San Diego, CA, 11:30 a.m. session.

Slavin et al., "Immunohematopoietic Reconstruction by Allogeneic and Autologous Bone Marrow Grafts as a Means for Induction . . . Autoimmune Disorders," *Transplantation Proceedings*, 25(1):1274–1275 (1993).

Slavin et al., "Immunotherapy of Minimal Residual Disease by Immunocompetent Lymphocytes and Their Activation by Cytokines," *Cancer Investigation*, 10(3):221–227 (1992).

Sykes et al., "Achieving allogengraftment without graft–versus–host disease: approaches using mixed allogeneic bone marrow transplantation," *Bone Marrow Transplantation*, 3:379–386 (1988).

Sykes et al., "Bone Marrow Transplantation as a means of inducing tolerance," *Seminars in Immunology*, 2:401–417 (1990).

Truitt et al., "Impact of Pretransplant Conditioning and Donor T Cells . . . Transplantation," *Blood*, 77(11):2515–2523 (1991).

Truitt et al., "Characterization of Alloimmunization–induced T Lymphocytes Reactive against AKR Leukemia In Vitro and Correlation . . . In Vivo," *J. Immunology*, 131(4):2050–2058 (1983).

Zanjani et al., "Engraftment and Long–term Expression of Human Fetal Hemopoietic Stem Cells in Sheep following Transplantation in Utero," *J. Clin. Investigation*, 89:1178–1188 (1992).

Zeis et al., "Eradication of residual disease by administration of Leukemia–specific T cells after experimental allogeneic bone marrow transplantation," *Experimental Hematology*, 26:1068–1073 (1998).

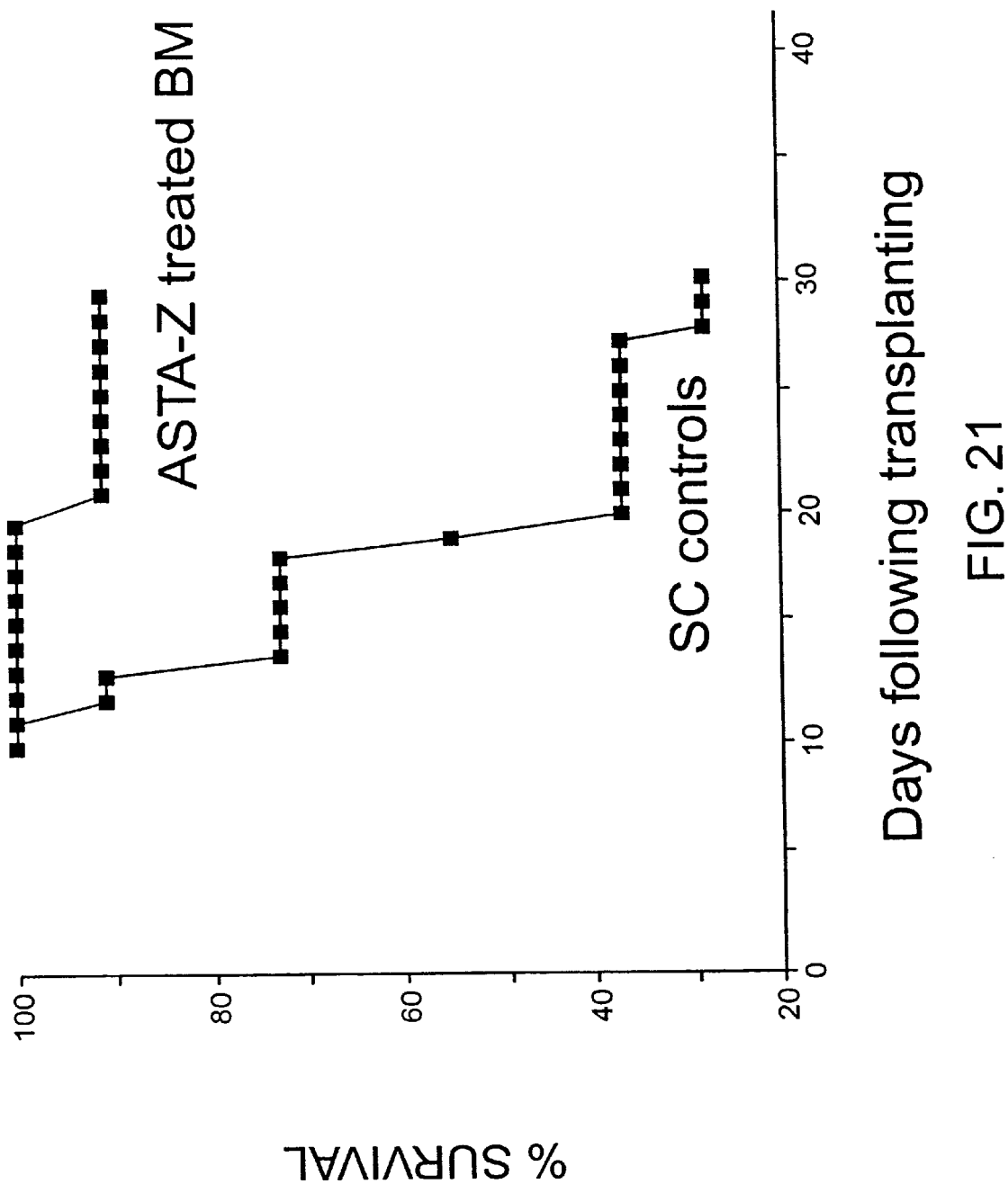

NON-MYELOABLATIVE TOLEROGENIC TREATMENT

CROSS-REFERENCES TO RELATED APPLICATIONS

This application is a continuation-in-part of U.S. application Ser. No. 09/222,011, filed Dec. 31, 1998, which is a continuation-in-part of U.S. application Ser. No. 08/862,550, filed on May 23, 1997, now abandoned.

STATEMENT AS TO RIGHTS TO INVENTIONS MADE UNDER FEDERALLY SPONSORED RESEARCH AND DEVELOPMENT

BACKGROUND OF THE INVENTION

Transplantation of organs, hematopoietic cells and somatic cells has been a crucial therapeutic regimen for patients suffering from a variety of maladies. Although the techniques necessary for transplants are quite straightforward, the great stumbling block for successful transplantation has been the immune system. A fundamental problem has been the great vigor with which the host immune system reacts against introduction of antigens found in donor tissues or cells.

Transplantation of allogeneic donor (i.e., the same species but not genetically identical to the host patient) or xenogeneic donor (i.e., a species other than that of the host) grafts has posed particularly great difficulties. The continued functioning of any donor graft depends upon continued functioning of the donor cells that make up that graft. The cells of donor grafts, however, can elicit an immune reaction on the part of the host that, if unchecked, may lead to destruction of the graft.

One method of alleviating the reaction by the host against a graft has been administration of immunosuppressive treatment to the host. Unfortunately, despite the availability of new and very effective immunosuppressive drugs, recurrent episodes of acute and chronic graft rejection remain common, frequently causing loss of graft function. Moreover, the long-term success of transplantation is often limited by complications resulting from drug-related toxicity and from long-term immunosuppression (e.g. infections and secondary malignancies). In addition, transplantation of bone marrow cells (BMC) or small intestine, which are rich in immunocompetent lymphocytes, frequently is associated with a potential life-threatening complication due to graft versus host disease (GVHD).

It has been shown that a full hematopoietic chimera, i.e., a patient whose own BMC have been 100% replaced by permanently engrafted BMC from another individual (donor), can permanently accept donor-derived allografts with no need for maintenance immunosuppressive therapy. However, induction of full hematopoietic chimerism has been difficult to accomplish. First, substantially complete destruction of the host's immunohematopoietic compartment ("lethal" conditioning) is usually required for engraftment of matched and especially mismatched BMC. With lethal conditioning of the host, GVHD consistently causes morbidity or mortality. In such cases, T cell depletion of the graft hematopoietic material represents the only approach for effective prevention of GVHD. T cell depletion in turn is associated with an increased incidence of graft rejection. To overcome the problem of graft rejection, recipients of T cell depleted marrow allografts may require particularly strong conditioning or, alternatively, very high numbers of T cell depleted BMC. Subjecting patients to aggressive rejection-prevention protocols, such as total body irradiation (TBI) alone or TBI in combination with a short course of immunosuppressive drugs is unlikely to be accepted by clinicians treating patients in need of organ allografts.

It has been proposed that true bilateral tolerance associated with mixed donor/recipient hematopoietic chimerism, i.e., the condition in which a patient possesses both recipient (host) and donor hematopoietic stem cells, rather than with full chimerism, would be preferable in clinical organ transplantation. Several experimental protocols have been designed to induce transplantation tolerance leading to mixed chimerism. Conditioning has required the use of high dose TBI followed by infusion with a mixture of T cell depleted donor and recipient BMC (Sachs et al., *Ann. Thorac. Surg.*, 56:1221 (1993); Ildstad et al., *Nature*, 307:168 (1984)) or inoculation with donor BMC after lower dose TBI and infusion of a mixture of antibodies against $CD4^+$ T cells, $CD8^+$ T cells and NK cells leading to general pancytopenia. Tomita et al., *J. Immunol.*, 153:1087 (1994); Tomita et al., *Transplantation*, 61:469 (1996). An alternative approach has been developed recently involving irradiation with a sublethal dose of TBI and inoculation with a very high number of T cell depleted donor-derived hematopoietic cells. Reisner et al., Immunol. Today, 16:437 (1995); Bachar-Lustig et al., *Nature Medicine*, 12:1268 (1986). Tolerogenic treatments using cyclophosphamide (hereinafter also referred to as "Cytoxan" or "Cy") in combination with TBI have also been described.

Total lymphoid irradiation (TLI) has been employed successfully as the sole preparatory regimen prior to infusion with donor BMC, to induce mixed hematopoietic chimerism and bilateral transplantation tolerance. Slavin S., *Immunol. Today*, 3:88 (1987); Slavin et al., *Isr. J. Med. Sci.*, 22:264 (1986). TLI is non-myeloablative and routinely given safely on an outpatient basis to transplant recipients and patients with Hodgkin's disease. Unfortunately, consistent induction of chimerism using TLI has required very high cumulative doses of radiation (3,400–4,400 cGy) that again would not be desirable for transplant recipients. TLI has significant advantages over TBI, especially in the clinical setting. TLI, which involves selective irradiation of the lymphoid compartment without exposing the whole body to ionizing irradiation, is well tolerated. In addition, TLI preserves intact a significant portion of the host's immunohematopoietic system, with resultant retained memory to recall antigens including infective agents. However, long courses of TLI can be time consuming and may be associated with short and long-term side effects that may not be suitable for routine clinical application.

SUMMARY OF THE INVENTION

The invention provides a new method for treating a host mammal to induce transplantation tolerance to cell, tissue and organ allografts and xenografts. Such transplants can provide replacement therapy for enzyme or metabolic disorders and adoptive immunotherapy for cancer and life-threatening infections in humans. The method also can be used to provide new animal models for tolerance induction toward allogeneic and xenogeneic cells. The invention also provides a new method of non-syngeneic cell therapy in which the cell population used for therapy is substantially depleted of responsiveness to host antigens prior to administration to the host.

In general, the invention features a method of treating a host mammal, including (a) administering donor antigens from a non-syngeneic donor to the host mammal; (b) administering a non-myeloablative dose of lymphocytotoxic agent (e.g., cyclophosphamide) or tolerizing agent to the host mammal to selectively eliminate the host mammal's lymphocytes responding to the donor antigens; and (c) administering a preparation of hematopoietic stem cells from the non-syngeneic donor to the host mammal.

Prior to step (a), the host mammal can be administered an immunosuppressive agent in a non-myeloablative regimen sufficient to decrease the host mammal's functional T lymphocyte population. The immunosuppressive agent can include one or more of an immunosuppressive drug, an alkylating agent, ionizing radiation, or anti-leukocyte or anti-leukocyte function antibodies. It is particularly advantageous to use a short course of TLI (sTLI) as the immunosuppressive agent, for example 1–12, frequently 1–6, doses of 200 cGy/dose.

The donor antigens administered to the host mammal can include non-cellular antigens, cells, tissues and/or organs. For example, the donor antigens can include hematopoietic stem cells or other viable cells. If the donor antigens include viable cells such as hematopoietic stem cells, then the immunosuppressive regimen referenced above should decrease the T lymphocyte population of the host to a level permitting at least transient survival of the donor's cells. For example the T lymphocyte population of the host can be decreased by 90%, 95% or 99%.

The host mammal can be an animal or a human, for example a human cancer patient. The donor can be allogeneic or xenogeneic to the host mammal. Following performance of the method, the host mammal's blood can contain 20% or more donor cells. After administering the preparation of donor hematopoietic stem cells, with resultant engraftment of such cells in the host, the host can be treated with allogeneic cell therapy. This involves infusing allogeneic lymphocytes from the donor into the host mammal. Alternatively, the host can receive transplanted cells, tissues or organs from the donor, with the transplants becoming engrafted in the host due to the donor-specific tolerance induced in the host mammal.

In another aspect, the invention features a host-derived hematopoietic cell 25 composition, including host-originating and donor-originating hematopoietic cells, with the composition being depleted of donor-specific, host-originating lymphocytes. The hematopoietic cell composition can be made by treating a host mammal as described above, then isolating the hematopoietic cell composition from the host mammal.

In a further aspect, the invention features a method of making a non-human mammal/human chimera. This involves performing the methods described above, with the host mammal being a non-human mammal and the donor being a human being. The host mammal can be, for example, a rodent or pig. The result is a rodent, pig or other non-human mammal stably engrafted with human hematopoietic stem cells. As such, the non-human mammal host constitutes a hematopoietic mixed chimera.

The invention also encompasses a composition of cells containing a cell population from a first individual mammal. The cell population contains lymphocytes and is depleted of responsiveness to antigens of a second individual mammal that is non-syngeneic (i.e., allogeneic or xenogeneic) with the first individual mammal. The depletion of responsiveness is by a method involving the following sequential steps: (a) administering an antigen source expressed by the second individual mammal to the first individual mammal; (b) administering a non-myeloablative dose of a lymphocytotoxic or tolerizing agent to the first individual mammal; (c) administering a preparation of hemopoietic cells from the second individual mammal to the first individual mammal; and (d) isolating the cell population from the first individual mammal. In the composition of the invention, cells endogenous to the first individual mammal are 50% to 100% of the cells of the population. The antigen used can be cancer cells and the first individual mammal and the second individual mammal can both be humans. Alternatively, the first individual mammal can be a non-human primate, and said second individual mammal can be a human, or the first individual mammal can be a pig and said second individual mammal can a human.

The invention also features a method of treating a mammal with non-syngeneic cell therapy. The method involves infusing a population of cells from a donor mammal into a host mammal, with the donor mammal and the host mammal being non-syngeneic with each other. The cell population can contain lymphocytes, and prior to infusing, the cell population can be depleted of responsiveness to antigens expressed by the host mammal. The depletion of responsiveness can be by substantially eliminating T cells from the cell population. Elimination of T cells can be by exposing the cell population to an immunosuppressive agent in a non-myeloablative regimen or by contacting the cell with mafosphamide. These eliminations can be performed in vitro or in vivo.

Alternatively, the depletion of the cell population can be accomplished by contacting the lymphocyte population with a composition comprising antigens expressed by said host mammal and the contacting can be in vitro or by administering the antigens to the first individual mammal. The method can further include the step of, after the contacting with the antigen composition, delivering a non-myeloablative dose of a lymphocytotoxic or tolerizing agent to the lymphocyte population. This delivering can be in vitro or by administering the non-myeloablative dose to the donor mammal. The method can also optionally include the steps of: (a) after the delivering, administering a preparation of hemopoietic stem cells from the host mammal to the donor mammal; and/or (b) prior to the contacting with antigen, exposing the lymphocyte population to an immunosuppressive agent in a non-myeloablative regimen sufficient to decrease the number of functional T lymphocytes in the lymphocyte population. In (b) the exposing can be in vitro or by administering the immunosuppressive agent to the donor mammal. The antigen composition can contain one or more antigen sources, e.g., cells, organs, tissues, and non-cellular antigens. For example, the antigen can include hemopoietic cells or cancer cells expressing major histocompatibility complex molecules of the host mammal. The cancer cells can, for example, be from the host mammal.

Also within the invention is an article of manufacture that includes packaging material and a biological cell container within the packaging material. The cell container can contain a composition that includes hematopoietic stem cells and the packaging material can contain a label or package insert indicating that the hematopoietic stem cells are to be used in step (a) or step (c) in a method of inducing non-syngeneic donor-specific tolerance in a host mammal. The method includes the steps of: (a) administering donor antigens from a non-syngeneic donor to the host mammal; (b) administering a non-myeloablative dose of lymphocytotoxic or tolerizing agent to the host mammal to selectively eliminate the host mammal's lymphocytes responding to the donor antigens; and (c) administering a preparation of hematopoietic stem cells from the non-syngeneic donor to the host mammal.

Another article of manufacture encompassed by the invention is one that includes packaging material, a biological cell container within said packaging material, with the cell container containing any of the cell compositions of the invention described above. The packaging material contains a label or package insert indicating that the composition is to be used in a method of treatment including administering the composition to a second individual mammal that is in need of the composition.

The invention also features a method of inducing tolerance in a host mammal to a graft from a non-syngeneic host mammal. The method includes the following steps: (a) administering donor antigens from a non-syngeneic donor to the host mammal; (b) administering an immunosuppressive agent to the host mammal in a non-myeloablative regimen sufficient to decrease the host mammal's functional T lymphocyte population; (c) transplanting cells, a tissue, or an organ from the donor into the host animal, (d) administering a non-myeloablative dose of lymphocytotoxic or tolerizing agent to the host mammal to selectively eliminate the host mammal's lymphocytes responding to the donor antigens; and (e) administering a preparation of hematopoietic stem cells from the non-syngeneic donor to the host mammal. Steps (a), (b), and (c) of the method are performed on the same day and prior to steps (d) and (e).

The term "non-myeloablative" as used herein includes any therapy that does not eliminate substantially all hematopoietic cells of host origin. "Transplantation" as used herein refers to transplantation of any donor-derived material including cells, tissues and organs. The cells may be hematopoietic or non-hematopoietic. "Donor antigens" as used herein refers to any donor-derived material that elicits a host immune response, including non-cellular antigens, cells, tissues or organs. Stem cells are particularly useful as donor antigens. A "lymphocytotoxic agent" is an agent that kills T cells or paralyzes T cell function. A "tolerizing agent" is an agent that energizes or "vetos" T cells by preventing development of normal T cell-dependent responses. The term "cancer" as used herein includes all pathological conditions involving malignant cells; this can include "solid" tumors arising in solid tissues or organs as well as hematopoietic tumors such as leukemias and lymphomas. The term "donor-specific tolerance" as used herein refers to tolerance of the host to donor-derived material. "Non-syngeneic" as used herein can be allogeneic or xenogeneic. "Depletion of responsiveness" in a particular cell population, as used herein, means either a decrease in the number of responsive cells, a decrease in the responsiveness of responsive cells, or both. Where cells are herein said to be "endogenous" to an individual mammal, it is understood that the cells themselves, or their precursors, were in that individual mammal prior to any administration of cells from another individual mammal.

Induction of donor-specific tolerance across strong major histocompatibility complex MHC and minor histocompatibility loci (MiHL) barriers, as well as across species barriers (xenogeneic tolerance) may be achieved in mammalian hosts using the tolerogenic treatment described herein. Induction of donor-specific transplantation tolerance while avoiding the need for maintenance immunosuppressive treatment is a highly desirable goal in clinical transplantation.

The non-myeloablative tolerogenic treatment described herein induces a state of long-lasting donor-specific tolerance to a wide variety of donor-derived material. Such an approach is attractive for allogeneic and xenogeneic transplantation of cells, tissues and organs in clinical settings, since all the steps of the protocol are well tolerated and relatively safe. Since there is no need to eradicate the entire host immunohematopoietic system during the course of the procedure, the recipients retain immune memory and are in a better position to resist graft-versus-host disease on the one hand and infectious complications on the other. This can be of crucial importance in clinical practice. The protocols for inducing donor-specific tolerance may be delivered, at least in part, as outpatient procedures.

The methods of non-syngeneic cell therapy provided herein can be especially useful in conditions in which cell, tissue, or organ failure or misfunction occurs. They can therefore be useful in, for example, metabolic deficiencies (including genetic metabolic deficiencies), autoimmune diseases, and cancer. The methods are therefore useful in passively transferring, from a donor to a host, immunity to one more infectious agents. They can be used without prior treatment of the host or subsequent to tolerization of the host to donor antigens by one of the tolerization methods of the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting. Other features and advantages of the invention will be apparent from the following detailed description, and from the claims.

BRIEF DESCRIPTION OF THE DRAWINGS

FIG. 21. Survival of sub-lethally irradiated BALB/c mice after infusion of either untreated or ASTA-Z treated bone marrow cells from B6 mice.

DESCRIPTION OF THE SPECIFIC EMBODIMENTS

A. Tolerance Protocols

Figure 1:
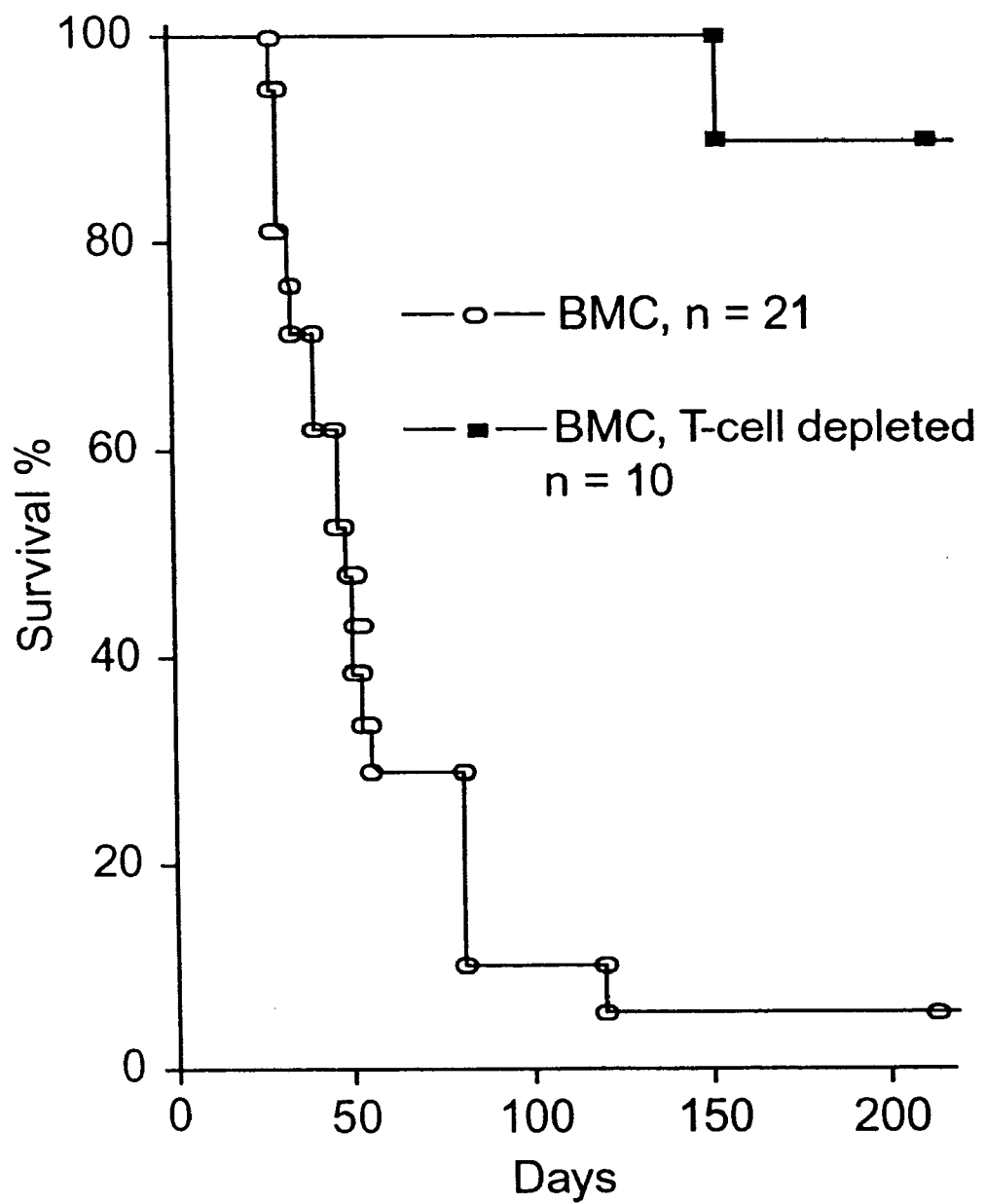
FIG. 1. Effect of T cell depletion from a second BMC infusion on survival of tolerant mice.

The present inventor has employed novel, non-myeloablative tolerogenic protocols to induce stable and donor-specific tolerance to non-syngeneic transplants (i.e., transplants of cells, tissues or organs not genetically identical to the host). A protocol for the tolerogenic treatment can be summarized as follows:

Step 1: Administer an immunosuppressive agent to a host mammal in a non-myeloablative regimen sufficient to decrease, but not eliminate, the host mammal's functional T lymphocyte population.

Step 2: Infuse donor antigens, preferably viable hematopoietic cells, from a non-syngeneic donor into the host mammal.

Step 3: Eliminate those host T lymphocytes responding to the infused donor antigens using a non-myeloablative dose of lymphocytotoxic or tolerizing agent.

Step 4: Administer a preparation of donor hematopoietic stem cells to the host mammal.

This non-myeloablative, donor-specific tolerogenic treatment results in conversion of a host to a hematopoietic mixed chimera with high levels of donor hematopoietic cells. Typically, the mammalian hosts are human patients, although a recipient of the tolerogenic treatment may be any mammal. Non-syngeneic transplantation can include allogeneic as well as xenogeneic transplantation of organs, tissues or cells. Hence, hematopoietic stem cells and other donor antigens used in steps 2 and 4 may be derived from allogeneic or xenogeneic sources.

Human patients for which the tolerogenic treatment is appropriate include without limitation those with loss of organ or tissue function including loss of metabolic function such as in diabetes; patients with enzyme deficiencies caused by inborn genetic diseases such as Gaucher's disease, metachromatic leukodystrophy and Hurler's Syndrome; patients with autoimmune disorders such as lupus erythematosus and rheumatoid arthritis; and cancer patients. Patients suffering from heart, liver or kidney failure, for example, are excellent candidates for conditioning with the tolerogenic treatment prior to transplantation with the appropriate organ. Patients requiring a skin or bone graft may also be subjected to the tolerogenic treatment prior to grafting. Cancer patients receiving the tolerogenic treatment can include patients suffering from any malignancy, either solid tumors such as breast cancer or hematopoietic malignancies including acute and chronic leukemia, lymphoma, and myelodysplastic and myeloproliferative disorders.

In accordance with this invention, a significant number of the host mammal's functional T lymphocyte population remains in the host after the non-myeloablative regimen of Step 1. Nevertheless, engraftment of donor cells can occur because (a) donor-reactive host T lymphocytes are eliminated in step 3, and (b) donor-derived T lymphocytes and/or stem cells present in the subsequent infusion or infusions (Step 4) may act as "veto" cells to produce a veto effect. Veto cells, as used herein, include T lymphocytes, especially $CD8^+$ T cells, that result in down regulation, rather than stimulation, of other T lymphocytes. Veto effects may be induced by other proliferating hematopoietic cells including T cell-depleted stem cells that are poorly immunogenic but that can veto host T cells. In the veto effect, host-originating T lymphocytes are down-regulated by donor-derived veto cells, including stem cells and/or lymphocytes. Other replicating donor-derived cells, or even non-cellular antigens, can also veto host allo- or xeno-reactive T cells if provided repeatedly and in relatively high concentrations. Similarly, immunocompetent T cells present in the donor infusion may be down-regulated by veto cells of host origin. Thus, tolerance of graft vs host and host vs graft may occur simultaneously due to a balanced equilibrium between veto cells of host and donor origin on the one hand and the degree of immunogenicity and alloreactivity of the graft on the other.

In some methods of the invention, it will not be necessary to perform all of steps 1–4 in order to induce tolerance. Tolerance can be induced using either (a) step 1 alone, (b) step 2 alone, (c) steps 1 and 2, (d) steps 2 and 3; (e) steps 2, 3 and 4, (f) steps 1, 2 and 3, or (g) steps 1, 2, 3, and 4.

(i) Step 1

Examples of immunosuppressive agents useful in Step 1 include without limitation immunosuppressive drugs such as methotrexate and fludarabine (FLU); alkylating agents such as Cy, melphalan, thiotepa and busulfan; polyclonal and monoclonal anti-thymocyte globulin (ATG) and anti-lymphocyte globulin (ALG); and ionizing radiation such as TLI and TBI. Due to its non-selective effects on all of the host's hematopoietic cells and its severe immediate and long-term side effects, TBI is not preferred. If TBI is used, it should be at a dose level that causes no severe or irreversible pancytopenia. The non-myeloablative regimen advantageously is a short and well-tolerated course of TLI (sTLI) which may cause a major reduction in the number and/or function of host T lymphocytes in all lymphoid organs. As discussed below, it has been discovered that sTLI can effectively induce unresponsiveness to donor antigens at relatively low cumulative radiation doses.

The sTLI immunosuppressive regimen may comprise, for example, 1 to 12 daily fractions of 200 cGy/each depending on the host-versus-graft potential and the T lymphocyte content in the stem cell preparation administered in Step 4. Stem cell preparations rich in T lymphocytes may require only 1–3 sTLI fractions, or may not require immunosuppression at all (zero sTLI fractions). Transplantation of T cell-depleted stem cell preparations or stem cell preparations with low levels of T lymphocytes, however, may require the use of 4–12 fractions. The sTLI regimen causes only a transient reduction in the number of host T lymphocytes and is clinically feasible on an outpatient basis. There are no anticipated severe side effects since a routine cumulative dose of TLI used clinically for lymphoma patients consists of 4,400 cGy.

The fludarabine immunosuppressive regimen can involve a single dose or multiple doses. For example, fludarabine can be administered to the host at a dose of about 25 mg/kg/day for 1, 2, 3, 4, 5, 6, 7, 8, 9 or 10 days.

Preferably, the immunosuppressive agent transiently decreases the host functional T lymphocyte population by at least about 90%. More preferably, the non-myeloablative regimen transiently decreases the host functional T lymphocyte population by at least about 95%, and most preferably, by at least about 99%. Reductions of less than 90% of the lymphocytes are also within the scope of this invention, provided that transient survival of donor antigens, provided in Step 2, is possible.

In some donor/recipient combinations, tolerance to donor antigens may be inducible without the necessity of performing Step 1. In this case, the preparation of donor hematopoietic stem cells administered in Step 4 must contain a sufficient number of T cells to provide a protective veto function against residual host T cells escaping the effects of Step 3.

(ii) Step 2

In Step 2 of the tolerogenic treatment, antigens from a non-syngeneic donor are administered to the host mammal in order to stimulate and cause proliferation of donor-specific T lymphocytes of the host. The stimulated subpopulation of donor-specific host T lymphocytes is then eliminated or tolerized in Step 3. The donor antigens may be administered (Step 2) to the host after the non-myeloablative immunosuppressive regimen (Step 1) described above. Alternatively, the donor antigens may be administered to a non-immunosuppressed host (if Step 1 is excluded as described above).

The donor antigens administered in step 2 can include, without limitation, non-cellular antigens, cells, organs, tissues or tissue extracts, or even anti-idiotypic antibodies that mimic donor antigens. In general, any donor antigens that elicit an immune response in the host are within the scope of this invention. Any source of donor antigens from a non-syngeneic donor can be used, and the non-syngeneic donor can be allogeneic or xenogeneic to the host.

The infusion of donor antigens should comprise donor antigenic determinants for which tolerance is desired. For example, if it is desired to transplant into the host donor-derived material bearing only class I histocompatibility antigens, it may be necessary to eliminate only class I-reactive host T lymphocytes in Step 3. This could be accomplished by infusing, in Step 2, donor antigens bearing only class I antigenic determinants. On the other hand, additional donor antigenic determinants may be present in the infusion of Step 2 even though host tolerance to these additional antigenic determinants may not be necessary. Thus, elimination of class I- and class II-reactive host T lymphocytes by infusion of donor antigens bearing class I and class II antigenic determinants may be performed even if the later transplanted donor material bears only Class I antigenic determinants.

The donor antigens infused in Step 2 can be viable hematopoietic stem cells from a non-syngeneic donor. The donor hematopoietic stem cells generally are not T cell depleted, although use of T cell depleted donor hematopoietic stem cells in Step 2 is also within the scope of this invention. Donor hematopoietic stem cells for use in Steps 2 and/or 4 may be obtained, for example, by direct extraction from the bone marrow or from the peripheral circulation following mobilization from the bone marrow. The latter can be accomplished by treatment of the donor with granulocyte colony stimulating factor (G-CSF) or other appropriate factors that induce mobilization of stem cells from the bone marrow into the peripheral circulation. The mobilized stem cells can be collected from peripheral blood by any appropriate cell pheresis technique, for example through use of a commercially available blood collection device as exemplified by the CS3000 Plus blood cell collection device marketed by the Fenwal Division of Baxter Healthcare Corporation. Methods for performing apheresis with the CS3000 Plus machine are described in Williams et al., *Bone Marrow Transplantation* 5: 129–133 (1990) and Hillyer et al., *Transfusion* 33: 316–321 (1993). Alternative sources of stem cells include neonatal stem cells (e.g., cord blood stem cells) and fetal stem cells (e.g., fetal liver of yolk sac cells). Stem cells that have been expanded in vitro with a mixture of hematopoietic cytokines also may be used. Other useful stem cell preparations include stem cells that have been transduced with genes encoding donor-type MHC class I or class II molecules, as well as stem cell preparations containing stem cells and/or T cells transduced with herpes simplex thymidine kinase or other "suicide" genes to render the mature T cells sensitive to ganciclovir or other appropriate drugs in the event of severe GVHD.

(iii) Step 3

With respect to Step 3, "elimination" of the proliferating donor-specific host T lymphocytes as used herein includes host T lymphocyte inactivation or tolerization as well as host T lymphocyte death. Examples of lymphocytotoxic agents useful in Step 3 include Cy, melphalan and methotrexate. Cy, for example, is a short acting cytotoxic drug known for its ability to kill lymphocytes, especially cells that proliferate in response to antigenic stimulation (Bach J F, Amsterdam: North-Holland (1975); Aisenberg et al., *Nature*, 213:498 (1967); Paul W E, *Fundamental Immunology*. New York: Raven, (1984)). Cy can also facilitate activation of antigen-specific T cell suppressors responsible for maintenance of the tolerant state. Chernyakhovskaya et al., *Transplantation*, 38:267 (1984); Maeda et al., *Transplantation*, 57:461 (1994). Other agents known to eliminate proliferating T cells in response to donor antigenic stimulation may also be used, including monoclonal antibodies against activation markers of T lymphocytes such as anti-CD25, anti-DC69 and anti-Ia/DR antibodies. Alloreactive host T cells may be tolerized, rather than killed, by using agents that block co-stimulation in conjunction with activation, since T cell engagement with antigen without a second signal provided by co-stimulation results in tolerance. Such tolerizing agents include without limitation CTLA4-Ig, anti-B7.1 or anti-B7.2, anti-CD28, and antibodies against adhesion molecules such as anti-LFA1, anti-CD44, anti-CD40 ligand (CD40L) and similar agents. If tolerizing agents are used, steps 2 and 3 can be performed simultaneously.

(iv) Step 4

In order to ensure an acceptable state of stable, mixed chimerism with relatively high numbers of circulating donor cells, donor hematopoietic stem cells are administered to the host following performance of Step 3. This infusion of donor stem cells (Step 4) is derived from the same donor, or from a donor genetically identical to that providing the antigens for Step 2. Hematopoietic stem cells from bone marrow, from mobilized peripheral blood populations, or other stem cell preparations as described above (e.g., cord blood stem cells), may be used. The number of stem cells administered in Step 4 can vary depending on the T cell content of the stem cell preparation. If the preparation is not T cell-depleted, then relatively small numbers of stem cells generally are administered. If the stem cell preparation is T cell-depleted, then larger numbers of stem cells can be administered since there is no risk of GVHD.

The donor hematopoietic stem cells of the second infusion may or may not be T cell depleted, depending on the immunologic disparity between the donor and recipient, the intensity of immunosuppression given in Step 1 and the degree of chimerism desirable in view of the immunogenicity of the graft. When higher fractions of sTLI (4–12), or other immunosuppressive agents providing equivalent immunosuppression, are used in the immunosuppressive regimen of Step 1, the second infusion comprising donor hematopoietic stem cells typically is T cell depleted to control for GVHD. When Step 1 involves little immunosuppression (for example, 1–3 fractions of sTLI), or when Step 1 is eliminated altogether, the infusion of donor hematopoietic stem cells in Step 4 typically is not T cell depleted. If not T cell depleted, the donor stem cells provided in Step 4 can be infused in graded increments over a period of weeks or several months, while monitoring for signs of GVHD.

In mouse experiments reported below, the mice received sTLI of 0–6 fractions of 200 cGy/fraction (Step 1). The donor-reactive T cells of the host were activated (Step 2) by injecting non-T cell depleted donor BMC ($3 \times 10^7$ cells). The activated host T cells were subsequently eliminated (Step 3) by a non-myeloablative dose (200 mg/kg or 3 doses of 60 mg/kg) of Cy. Mixed chimeras with low levels (e.g., 7%–20%) of donor cells in the blood were predominant after the Cy treatment. Induction of higher levels of hematopoietic mixed chimerism (e.g., >20% of donor cells in blood) was achieved by administering (Step 4) a second infusion comprising donor hematopoietic stem cells, allowing life-long survival of donor skin allografts.

In mice treated with 6 doses of TLI, Step 4 was required to achieve a level of tolerance permitting acceptance of full thickness skin allografts. It is well known that full-thickness skin presents the most stringent test for donor-specific tolerance. Skin allograft acceptance can be accomplished only in stable chimeras (Maeda et al., *J. Immunol.*, 150:753 (1993)) and success of skin acceptance may depend on the level of donor-derived cells in the host's blood.

In further experiments reported below, deletion of all host-derived, donor-reactive T lymphocytes following Step 3 permitted rapid engraftment of even low numbers of donor stem cells ($2-3 \times 10^6$/mouse) administered in Step 4, which normally would not be sufficient for induction of stable mixed chimerism. In parallel with this, the full anti-donor unresponsiveness induced following Step 3 also resulted in exquisite sensitivity to donor T lymphocytes, leading to lethal GVHD. Hence, whenever donor-reactive host T cells are effectively depleted, elimination of immunocompetent T lymphocytes from the hematopoietic stem cell preparation administered in Step 4, or use of lifespan-limited lymphocytes (e.g., carrying suicide genes), is crucial for prevention of GVHD. Due to the selective deletion of donor-reactive host lymphocytes, even $2-3 \times 10^6$ BMC (T cell-depleted), administered following Step 3, engrafted and converted host mice into stable mixed chimeras with relatively high levels (20%–50%) of donor-derived hematopoietic cells in the blood.

T cell depletion of donor stem cell preparations has been known to increase the risk of graft rejection. Thus, inoculation with extremely large numbers of donor stem cells has been mandatory for engraftment of T cell depleted BMC, especially in recipients conditioned with previous non-myeloablative protocols. Truitt et al., *Blood* 77, 2515–2523 (1991); Reisner et al., *Immunol. Today* 16, 437–440 (1995); Bachar-Lustig et al., *Nat. Med.* 12, 1268–1273 (1995). The ability to induce engraftment using low numbers of donor hematopoietic stem cells (T lymphocyte depleted) is a significant advantage of the present protocols. This is due to the improved acceptance of donor hematopoietic stem cells on the one hand combined with a reduced risk of GVHD that would otherwise follow from the use of higher stem cell inocula, on the other. Notably, animals non-specifically immunosuppressed by sTLI and Cy (without infusion of donor-antigens prior to Cy) were shown to reject T lymphocyte depleted BMC. Thus, the present data clearly show the advantage of donor-specific tolerogenic conditioning in comparison with non-specific immunosuppression approaches, while avoiding potentially hazardous high doses of TBI. GVHD can also be controlled using the tolerogenic agents described above for use in step 3. In addition, antibodies to CD52, CD40 ligand, CD40, IL-2 receptors (e.g., CD25) can be used to modulate GVHD. It is understood that the term antibody applies both to native antibodies, or as functional fragments of antibodies (e.g., Fab, $F(ab')_2$, or Fv fragments). Furthermore, they can be used as immunotoxins, e.g., conjugated with toxins such as Pseudomonas toxin or diphtheria toxin, ricin, or a radionuclide, e.g., $^{125}I$ or $^{131}I$.

Interestingly, life-long tolerance to full thickness donor-derived skin grafts was also accomplished in recipients who were not subjected to Step 1 and in recipients in which Step 1 involved only a single fraction of TLI (200 cGy). Thus, a balance exists between the intensity of the conditioning of the host and the susceptibility of the host to GVHD induced by the presence of donor-derived T cells: recipients of a single fraction of sTLI could resist GVHD induction by a large inoculum of non-T cell depleted donor BMC whereas the sensitivity of the hosts to GVHD was increased in recipients conditioned with 6 fractions of sTLI. Hence, a second infusion (Step 4) comprising non-T cell depleted donor BMC could be used relatively safely in recipients of 1 dose of sTLI whereas T cell depletion of the second infusion was mandatory in recipients of 6 fractions of sTLI. The sensitivity of the 6×sTLI recipients to develop GVHD was likely due to inability to veto the host-reactive donor cells due to effective depletion of all host T cells.

Tolerant mixed hematopoietic chimeras generated by the tolerogenic treatment described herein remain immunocompetent to third party grafts. In experiments described below, all tolerant B6→BALB/c chimeras that accepted B6 skin allografts rejected non-relevant CBA skin grafts within 16–20 days (n=11). Thus, tolerance induction neither eliminated nor impaired normal reactivity by the host immune system retained in the mixed chimera. This is an important advantage of the method, since recipients are not immunocompromised due to transient loss of all host-derived immune cells, which is otherwise unavoidable when chimeras are comprised of 100% donor cells following TBI. A patient who retains a host-derived immune apparatus with memory cells is in a better position to resist primary and secondary infections. This retained resistance to intercurrent infections, particularly to viral agents infecting host target cells, is of crucial importance. This is because the donor hematopoietic cells may be MHC disparate and, therefore, incapable of providing immune protection against virally-infected host tissues.

The above-described tolerogenic treatment may be employed to induce transplantation tolerance across xenogeneic barriers. Xenogeneic skin transplantation may be considered the most stringent test for donor-specific tolerance. As described below, the present inventor has succeeded in inducing permanent tolerance in mouse-to-rat skin grafts. The same donor-specific tolerance induction protocol presented herewith can be applied to xenogeneic transplantation in humans. The xenogeneic graft (e.g., pancreatic islets) may be taken from non-human mammals and transplanted into humans.

A tolerogenic treatment for xenogeneic transplantation may be performed as follows. sTLI (Step 1) is carried out, followed by an infusion (Step 2) of xenogeneic donor antigens, for example, BMC. Subsequently, at least one non-myeloablative dose of lymphocytotoxic or tolerizing agent is administered (Step 3). If necessary, the lymphocytotoxic agent can be administered in multiple low doses over several days. Administration of the lymphocytotoxic agent is followed by a infusion of a preparation comprising T cell-depleted donor hematopoietic stem cells (Step 4). The stem cells may be obtained from the blood or bone marrow of an adult donor. Alternatively, partially immunocompetent cord blood cells may be used, or even fetal stem cells obtained from the liver or yolk sac of embryos. Stem cells that have been expanded in vitro with a mixture of hematopoietic cytokines also may be used. Administration of stem cells in Step 4 leads to engraftment of the xenogeneic donor stem cells and permanent transplantation tolerance of the host to donor derived organs. In an alternative embodiment, xenogeneic transplantation may be performed without administration of a non-myeloablative regimen (Step 1 eliminated) and with the second infusion (Step 4) comprising non T cell depleted donor hematopoietic stem cells.

(v) Short Protocol for Induction of Transplantation Tolerance

In regard to use of the tolerogenic method of the invention in non-syngeneic organ, tissue or cell transplantation, the results of the experiments described in Example 14 are of great importance. In these experiments, it was found that allogeneic grafts (bone marrow stroma or hearts) could be implanted without significant rejection on the same day (day 0) as a single dose of TLI (as step 1) and donor bone marrow (as step 2), followed on day 1 by Cy (as step 3) and on day 2 by a second dose of bone marrow (as step 4). This method was designated the "short protocol" in order to differentiate it from the longer protocols used in some other experiments. Thus, in such longer protocols, heart or skin grafts were, for example, implanted 20 days after cyclophosphamide treatment (step 3) (Example 5) and 19 days after the second bone marrow injection (step 4) (Examples 2, 3, 4, 6, 7, and 9). Furthermore, in another long protocol, sTLI, as step 1, was given over a period of 6 days (e.g., Example 3). It is hypothesized that, in the short protocol, the grafted organ acts together, and possibly in synergy, with the bone marrow given on day 0, as antigen. It is possible, in addition, that the bone marrow given on day 0 may not be necessary for establishment of tolerance. This method of the invention is however not limited by a particular mechanism of action.

The success of the short protocol broadens the applicability of the tolerogenic approach of the invention for human transplantation. For example, in the case of cadaveric transplantation, donor bone marrow (or any other tissue that can be used for step 2) is not normally available significantly in advance of the availability of the relevant organ (e.g., kidney, heart, liver, or lung), tissue (e.g., skin, bone, muscle, or cartilage), or cells (e.g., hepatocytes or pancreatic islet cells). Using the short protocol, bone marrow can be harvested from the donor at the same as the organ and both can be given to the recipient on the same day as non-myeloablative conditioning (e.g., TLI) (day 0). Simultaneously, bone marrow cells can be frozen and stored for use in step 4, either on day 2 and/or on subsequent days. In addition to broadening the applicability of the tolerogenic methodology of the invention for cadaveric allotransplantation, the short protocol can also, for the same reasons, greatly simplify the logistics of living-related donor or xenogeneic donor transplantation.

(vi) Articles of Manufacture

Also included in the invention are articles of manufacture including packaging material (e.g., a cardboard box) containing a biological cell container (e.g., a blood bag such as a semipermeable blood bag that can be used for culturing cells). The biological container can contain a composition that includes hemopoietic stem cells and the packaging material can include a package insert or a label indicating that the composition can be used as the antigen in step 1 and/or as the source of hematopoietic stem cells for step 4 of the tolerogenic protocol.

(vii) Chimeras

In another embodiment, the invention involves a method of making a non-human mammal/human hematopoietic chimera. The method comprises making a non-human mammal tolerant to antigens originating from a human donor, using the non-myeloablative tolerogenic treatment described herein. That is, the non-human mammal functions as the "host mammal" in the protocols described above, and a human being is the "donor." For example, a rodent can be tolerized to human cells, tissues and organs by employing Steps 1–4 of the disclosed tolerogenic protocol to produce a mixed chimera rodent permanently engrafted with human hematopoietic cells. It is known that such hematopoietic engraftment is possible even between disparate species. For example, it has been demonstrated that human hematopoietic cells can engraft in mice. See, for example, Marcus et al., Blood 86: 398–406 (1995). In those cases where survival and functioning of human hematopoietic cells is less than optimal in non-human mammalian hosts, it is possible to provide the host mammal with human hematopoietic cytokines in order to ensure engraftment of the human cells.

There are numerous uses for such chimeric animals. For example, since the host mammals have been tolerized to the human donor, it is possible for human tissues, e.g., tumors or HIV-infected hematopoietic cells, to be transplanted into and accepted by these rodents in order to produce rodent models of human disease. Thus, these non-human mammal/human chimeras may be used to study biological phenomena related to human disease, including testing of new drugs.

Production of non-human mammal/human hematopoietic mixed chimeras is of even greater significance for those non-human mammalian species targeted as potential sources of cells, tissues and organs for transplantation into human patients. For example, it is widely recognized that pigs are a potential useful source of tissues and organs for transplantation into humans. Such porcine materials are subject to an immediate, "hyperacute" rejection response when transplanted into human patients, as well as to longer-term immune-mediated rejection by the human host. Pigs are being genetically engineered or otherwise treated to protect tissues and organs of such pigs from being hyperacutely rejected when transplanted into a human patient. This can be accomplished, for example, by providing the pigs human genes encoding human complement regulatory proteins, or by "knocking out" the genes responsible for production of pig antigens recognized by preformed xenoantibodies present in all humans. See, for example, PCT/US96/15255 and PCT/IB95/00088.

A "two-way" variation of the present tolerogenic protocols can be applied to such genetically engineered pigs as well as to other donor mammals to allow for ready transplantation of xenogeneic donor cells, tissues and organs into humans. For example, in a preliminary tolerization procedure, a human patient can function as an initial "donor" to provide antigens and hematopoietic stem cells to a "host" pig in the 4-Step protocol described above. As a result, the pig is transformed into a pig/human hematopoietic mixed chimera, with the pig's hematopoietic cells being tolerized to the human patient's cells, tissues and organs. Following this, the roles of the human patient and pig are reversed, with the pig becoming the donor and the human patient becoming the host in the 4-Step protocol. That is, the pig's hematopoietic cells, with T cells tolerant of the human patient, may be used in the 4-Step protocol for transformation of the human patient into a human/pig hematopoietic mixed chimera. The human patient is then able to accept cells, tissues and organs from the pig, for the reasons discussed above. The crucial advantage is that all of this can be accomplished while avoiding the risk of xenogeneic GVHD engendered by immunocompetent T cells of the pig, since the pig's T cells were made tolerant to the patient in the preliminary tolerization procedure. Thus, assuming the hyperacute rejection response can be overcome in other ways (e.g., genetic engineering of the animal providing the transplanted material), the present invention allows for xenogeneic transplantation of cells, tissues and organs into humans without the need for long-term immunosuppression. As an alternative to tolerizing the pig to the human patient's antigens, the pig's cells can be isolated and the tolerization can be performed in vitro, using standard tissue culture techniques familiar to those in the art. The human antigens can be cellular or non-cellular, as in step 2. They can be, for example, any of the hematopoietic cells described herein. Furthermore, the procedure, whether in vivo or in vitro, can be carried out using allogeneic host/donor mammalian (e.g., human, non-human primate, pig, rat, mouse, rabbit, or guinea pig) combinations as well as xenogeneic combinations.

In addition, tolerization of donor cells need not be antigen-specific. It can involve depletion of, for example, substantially all T cells in the bone marrow to be used in step 4, with the retention of stem cells and, optionally, other functional cell subsets (e.g., NK cells) that can have therapeutic benefit for a host subject suffering from a relevant disease (e.g., cancer). Methods for non-specifically depleting T cells from a hematopoietic cell sample include those described above for steps 1 and steps 3 of the tolerization protocol or those described below for steps A and C of the protocol used to deplete cells to be used for cell therapy. Experiments using such a non-specific in vitro depleting protocol are described in Example 15.

(viii) Cell Compositions

Another aspect of the invention is a hematopoietic cell composition derived from a host treated with the donor-specific tolerogenic treatment described above. The cell composition comprises host-originating lymphocytes and donor-originating lymphocytes. The proportion of donor-originating lymphocytes may vary. Preferably, the donor-originating lymphocytes comprise about 5% to about 50% of the lymphocyte composition. Most preferably, the donor-originating lymphocytes comprise about 20% to about 50% of the lymphocyte composition. The hematopoietic cell composition is specifically depleted of donor-specific, host-originating lymphocytes. "Depleted" in this context refers to reduction in numbers of T lymphocytes or reduction in T lymphocyte function sufficient to eliminate or significantly reduce anti-donor responses in the host and thus to reduce the risk of GVHD if the composition is administered to the donor. In a related aspect, the invention involves a method of making the above described hematopoietic cell composition. The method includes subjecting a host mammal to the tolerogenic treatment described above using an allogeneic or xenogeneic donor. After tolerogenic treatment, the method involves isolating a composition of hematopoietic cells from the host. This cell composition contains host and donor-originating hematopoietic cells, but is depleted of donor-specific host-derived T lymphocytes.

B. Cell Therapy Protocols

Completion of the tolerogenic treatment protocols can provide a platform for subsequent allogeneic cell therapy with donor lymphocyte infusions in cancer patients and in other patients with malignant and non-malignant diseases requiring bone marrow transplantation, since donor cells accepted by a tolerant host may induce graft-versus-leukemia (GVL) or graft-versus-tumor (GVT) effects. Such non-malignant diseases include without limitation aplastic anemia, genetic diseases resulting in enzyme deficiencies, and diseases caused by deficiencies in well-defined products of hematopoietic stem cells, such as osteoclast deficiency in infantile osteopetrosis and deficiencies in B cells and T cells in congenital and acquired immune-deficiency syndromes. Donors of cells for use in allogeneic cell therapy can be MHC (e.g., HLA in humans) incompatible or MHC identical with the host. Where MHC incompatible, the donor and host can share no MHC class I or class II alleles. Alternatively, they can share 1 or more (e.g., 2, 3, 4, or 5) MHC class I and/or class II alleles. Where donor and host are MHC identical, they can be incompatible at MiHL. They will thus preferably not be monozygotic twins. Allogeneic cell therapy is described, for example, in PCT publication no's. WO 95/24910 and WO 96/37208.

In allogeneic cell therapy, an anti-tumor or other anti-host hematopoietic cell effect is achieved by administering allogeneic peripheral blood lymphocytes to the host, either alone or in combination with one or more T cell activators. T cell activators (e.g., interleukin (IL)-2, IL-3, IL-4, IL-5, IL-6, IL-7, IL-10, IL-12, IL-13, IL-15, IL-15 interferon (IFN)-γ, or tumor necrosis factor (TNF)-α) can be given together with the cells or separately. Alternatively or additionally, allogeneic peripheral blood lymphocytes are "pre-activated" in vitro by a T cell activator such as IL-2 and then administered either alone or in combination with the same or different T cell activator. Where preactivated cells and non-preactivated cells are given to a subject, the pre-activated cells can be from an individual mammal other than the donor of the non-preactivated cells or from the same donor mammal. Preferably, one or more infusions of about $10^5$ to about $10^9$ cells/kg of allogeneic peripheral blood lymphocytes, including well-defined lymphocyte subsets, are administered. When preceded by the tolerogenic treatment described herein, these infusions of allogeneic lymphocytes are carried out with a much reduced chance of rejection of the anti-cancer effector cells, which need to become engrafted in the host. In addition, the risk of GVHD is reduced or eliminated by residual hematopoietic cells of the host and, if necessary, relatively late infusion of donor lymphocytes.

Allogeneic cell therapy following the tolerogenic treatment protocols described herein can be valuable not only in the context of cancer and other diseases, but also when it is desired to adoptively transfer immunity to infectious agents from the donor to the host. Thus, if a donor used in the tolerogenic protocols described herein is immune to an infectious agent (e.g., hepatitis B; see Ilan et al., *Hepatology* 18: 246–52 (1993)), this immunity can be transferred to a host by infusing lymphocytes from the donor to the host following completion of the tolerogenic protocols. Alternatively, the stem cell preparation infused in Step 4 of the tolerogenic protocols can itself provide the adoptive transfer of immunity, since stem cell preparations may contain immunocompetent lymphocytes.

From the above descriptions of depletion-mediated allogeneic and xenogeneic tolerance induction, particularly the discussion of methods for depleting hemopoietic cells (e.g., pig hemopoietic cells) of host-specific activity prior to their use is step 4 of the tolerizing protocol, it is clear that cell therapy can be performed using cells from individuals that are xenogeneic as well allogeneic to the host (i.e., recipient of cell therapy). In xenogeneic cell therapy, the same compositions of lymphocytes, with or without one or more T cell activators, e.g., IL-2, interferon-γ (IFN-γ), granulocyte-macrophage colony stimulating factor (GM-CSF), or interleukin-12 (IL-12), described above for allogeneic cell therapy, can be used. Moreover, the cells can be pre-activated, either in vitro or in vivo, prior to administration to the host. The cells to be used for cell therapy can be obtained from the blood, spleen, lymph nodes, or any other source of lymphoid cells, or they can obtained from a hematopoietic cell source, e.g. bone marrow or fetal liver.

(i) Depletion of Cells to be Used for Cell Therapy

Cell therapy can be given by administering unselected lymphoid cells. In general, however, prior to administration, the lymphoid cells will be depleted of T cells reactive to the recipients antigens or of responsiveness of T cells to the host's antigens. In the following description, the word "deplete" (or "depletion") refers to decreasing the numbers of T cells with responsiveness to antigens of the second individual and/or decreasing the responsiveness of such T cells. Depletion can be by decreasing the number of responsive lymphocytes or the responsiveness of the lymphocytes by 20%, 30%, 40%, 50%, 80%, 90%, 95%, 98%, 99% or even 100%.

In the above description of depleting donor hemopoietic cells of host-specific activity, the host/donor terminology was reversed. In the following discussion of methods to deplete lymphoid cells to be used for cell therapy, in order to avoid confusion as to the "host" and the "donor", the individual that is the source of the cells to be used for cell therapy will be referred to as the "first individual" and the individual that is to receive the cell therapy (e.g., a human cancer patient) will be referred to as the "second individual". Furthermore, the phrase "non-syngeneic" will be understood to cover both allogeneic and xenogeneic.

Methods of depleting lymphoid cells prior to their use for cell therapy basically involve the use of one or more of steps 1–4 described above for tolerizing a host against antigens of a donor. In order, however, to differentiate the steps used for depleting lymphoid cells to be used for cell therapy from those used for tolerizing a host mammal prior to transplantation, the steps used for depletion of lymphoid cells to be used for cell therapy are designated "steps A–D":

Step A: Expose lymphoid cells of a first individual to a non-myeloablative regimen sufficient to decrease, but not eliminate, the first individual's functional T lymphocytes.

Step B: Contact the lymphoid cells of the first individual with antigens of a non-syngeneic second individual.

Step C: Substantially eliminate deplete T lymphocytes of the first individual that are responsive to the antigens of the second individual by delivering a non-myeloablative dose of a lymphocytotoxic or tolerizing agent to the lymphoid cells.

Step D: Administer a preparation of hemopoietic stem cells obtained from the second individual to the first individual.

Essentially the same methods for performing steps 1–4 described above can be used to carry out steps A–D, except that some or all of the steps can be carried out in vitro using tissue culture methods familiar those in the art. Naturally, step D is always in vivo and can only be included where the entire depleting procedure is performed in vivo.

The lymphoid cells can be depleted using either (i) step A alone, (ii) step B alone, (iii) steps A and B, (iv) steps B and C, (v) steps B, C, and D, (vi) steps A, B, and C, or (vii) steps A, B, C, and D.

A method of depleting lymphoid cells of a first individual of reactivity against a second individual can involve, for example, harvesting lymphoid cells from the first individual and carrying out steps A–C in vitro. Alternatively, after carrying out step A in the first individual, the lymphoid cells can be isolated from the first individual and steps B and C carried out in vitro. In another embodiment, steps A and B can be carried out in the first individual, the lymphoid cells can be isolated from the first individual, and step C carried out in vitro. In addition, all the steps can be carried out in vivo, optionally including step D.

(ii) Step A

Step A decreases the total number of T cells in the cells to be used for therapy and is optionally used. Steps B and C are used to deplete only those cells or that T cell reactivity specific to donor antigens. As indicated by the experiments in Examples 10–13 below, step C, in some cases (e.g., where cancer cells are used as antigens), can be excluded since step B, can be sufficiently tolerogenic.

(iii) Step B

The same sources of antigen used in step 2 can be used in step B and they can be obtained by the same methods. In such methods, one or more (e.g., two, three, four, five, six, seven, eight, nine, or ten) reagents that enhance tolerance induction can be included during the contacting with recipient antigens of the donor cells to be used for therapy. Where this contacting is in vivo, the reagent can be administered to the donor mammal such that the reagent is present in the milieu of the donor lymphoid cells and the recipient antigens. Where the contacting is in vitro, the reagents can be added to cultures containing the donor lymphoid cells and the recipient antigens. Examples of appropriate reagents included CTL4-Ig fusion protein, and antibodies (or functional fragments thereof) specific for CD40L, B7.1, B7.2, CD28, LFA1, CD44, ICAM-1, CD25, CD69, and MHC class II molecules. While some these reagents can interact with appropriate cell surface molecules on the surface of responsive T cells (e.g., antibodies to CD40L, CD28, LFA1, CD25, and CD69), some on cells presenting the relevant antigens to the T cells (e.g., CTLA4-Ig fusion protein and antibodies to B7.1 and B7.2), and some have the potential to interact with molecules on both cell types (e.g., antibodies to ICAM1 and MHC class II molecules). However, it is understood that the invention is not limited by any particular mechanism of action of these reagents.

Cancer cells can be used as a source of recipient antigens for step B. As indicated by the experiments in Examples 10–13 below, lymphoid cells depleted using cancer cells for step B can be particularly useful for non-syngeneic cell therapy of a mammal with cancer, e.g., a human cancer patient. The experiments, which were carried out using mouse strains (X and Y) which differed either at both MHC and Minor Histocompatibility Loci (MiHL) or at MiHL only, indicate that lymphoid cells from a mouse of strain X exposed to cancer cells of strain Y, while being substantially depleted of graft-versus-host activity against antigens of strain Y, have enhanced anti-cancer therapeutic efficacy when transferred together with cancer cells to mice of strain Y. The therapeutic activity of the strain X lymphoid cells exposed to strain Y cancer cells was significantly greater than that of strain X lymphoid cells exposed to strain Y lymphoid cells, which, at least in the case of a MiHL incompatibility alone, was significantly greater than that of normal, unexposed, strain X lymphoid cells. Furthermore, in a mouse combination in which strains X and Y differ at both the MHC and MiHL, while lymphoid cells from normal, unexposed strain X mice displayed lethal GVH activity when transferred to host animals expressing strain Y antigens, lymphoid cells from strain X animals exposed either to cancer cells of strain Y or to lymphoid cells of strain Y were substantially depleted of the GVH activity. On the other hand, in a mouse combination in which strains X and Y differ at the MiHL only, exposure of strain X animals to cancer cells of strain Y depleted the strain X lymphoid cells of strain Y-specific GVH activity relative to lymphoid cells from normal, unexposed strain X animals but exposure of strain X animals to lymphoid cells from strain Y animals did not have an effect on the GVH activity of strain X lymphoid cells.

(iv) Use of Tumor Cells for Step B

The above experiments point to a novel form of non-syngeneic cell therapy of mammalian, and in particular human, cancer, in which the protocol used to deplete the lymphoid cells to be used for therapy of GVHD activity also results in enhanced anti-cancer therapeutic efficacy in the lymphoid cells. It is understood the action of cells used for non-syngeneic cell therapy can be tumoricidal, tumoristatic, or a combination of both. A subject to be given cell therapy with lymphoid cells of another histoincompatible subject could be treated by any or all of steps 1–4 above in order to establish non-reactivity (tolerance) to the antigens of the other subject. Alternatively, the cell therapy could be given without any of these steps. It could be given, for example, to a patient that for unrelated reasons (e.g., HIV AIDS, genetic immunodeficiency, chemotherapy, or radiotherapy) is significantly immunologically depleted (i.e., with a functional T cell population depleted by greater than 80%, 90%, 95%, or 99%). The lymphoid cells used for the therapy could be from an unrelated MHC compatible or incompatible human, a related MHC compatible or MHC incompatible human, or an individual of another species, e.g., a pig or a non-human primate. The lymphoid cells will preferably not be from a syngeneic individual (e.g., a monozygotic twin).

The cancer cells that can be use for step B are preferably of the type present in the subject to be given the cell therapy, e.g., leukemia, lymphoma, breast cancer, lung cancer, gastrointestinal tract cancer, renal cancer, melanoma, or genitourinary cancer, or a neural cell cancer such as brian cancer (e.g., glioblastoma, astrocytoma, or meningioma) and thus will express the same antigens or cross-reactive antigens. However, it remains possible that the enhanced anti-cancer therapeutic efficacy of non-syngeneic lymphoid cells depleted by exposure to tumor cells is not antigen specific and that cells depleted by exposure to a wide variety of tumors, will be have anti-tumor effects against the tumor harbored by a given subject. Thus step B can also be performed using, as a depleting agent, tumor cells of a type unrelated to that of the subject.

Cancer cells to be used for Step B will preferably express MHC molecules (at least one MHC class I or MHC class I molecule) of the patient. More preferably, they will be derived from the patient. Tumor cells from all subjects, including human patients, will be obtained by standard methods known to those in the art. In the case of non-solid, hematological cancers, the cells can be isolated or enriched from the blood, bone marrow, spleen, lymph nodes or other lymphoid tissue of the subject. In the case of solid malignancies, tumor cell suspensions can be obtained by disruption of solid tumor tissue removed by surgical excision of either the primary tumor or metastases. Where tumor cells of the patient are not available or are not available in sufficient quantity, it is possible that established tumor cell lines can be used. Such tumor cell lines can endogenously express the MHC molecules of the patient or they can have been stably transfected with and express genes encoding such molecules. If necessary, a plurality of such transfected lines, each expressing, either endogenously or due to stable transfection, the MHC molecules of the patient. Subcellular fractions or extracts (e.g., cell lysates, homogenates, or membrane fractions) of any of the above tumor cell preparations can also be used as antigen for step B. Furthermore, subcellular fractions, or isolated tumor antigens can be presented to donor T cells in association with antigen presenting cells (e.g., dendritic cells, macrophages, monocytes, or B lymphocytes), which can be freshly prepared or precultured. The antigen presenting cells can express MHC molecules of the patient, and preferably will be derived from the patient. Such antigen presenting cells can, for example, be pulsed with tumor cell extracts or peptides derived from tumor-associated polypeptide antigens prior to their use in step B. Alternatively, the antigen presenting cells can be transduced or stably transfected with expression vectors encoding full-length tumor-associated polypeptide antigens or peptides corresponding to subregions of such antigens. In addition, cell hybrids formed by fusion of tumor cells and antigen presenting cells can be used as the activating antigen for step B of the method.

It is envisaged that, where the second individual (i.e., the recipient of cell therapy) is a human patient and step B is to be carried out in vivo, the first individual (i.e., the source of the non-syngeneic cells) will likely either be a relative of the patient or an individual of another species. However, whether in vivo, in vitro, in a relative, or in an individual of another species, proliferation of the tumor cells used as antigen can be substantially eliminated by prior exposure of the tumor cells to a sufficient dose of an anti-proliferative agent, e.g., ionizing radiation or mitomycin-C. Alternatively, the above-mentioned subcellular fractions can be used.

It is understood that donor cells to be used for cell therapy can be exposed to tumor cells or tumor cell extracts with the principle purpose of enhancing tumoricidal or tumoristatic activity in the donor cells. While it is anticipated that donor cells treated in this way will generally be depleted of recipient-specific responsiveness, it is not always required that the donor cells exposed to tumor cells or tumor cell extracts be so depleted.

(v) Non-antigen-specific Methods of Depleting Cells

Protocols for non-specifically depleting hematopoeitic cells of responsive T cells can involve the use of any of the methods described above for step A without any of steps B–D. In addition, any of a wide variety of methods known in the art (e.g., use of magnetic beads, lytic complement, or flurorescence activated cell sorting) employing single or combinations of antibodies (monoclonal or polyclonal) that bind to T cells (or cells other than T cells) can be used to remove T cells. Such protocols can employ single or multiple (e.g., 2,3,4,5,6,8,10 or 12) treatments and one or more of the methods can be used. Furthermore, they can be performed either in vivo or in vitro. Such protocols will result in elimination of substantially all (e.g., greater than 80%, preferably greater than 90%, more preferably greater than 95%, and most preferably greater than 99%) of the T cells in the hematopoietic cell population. It is noted, as described above, that such protocols can also be used to deplete donor cells of reactivity to the host prior to use in step 4 of the tolerization method of the invention. An example of such protocol is provided in Example 15.

(vi) Cell Compositions

The instant invention also encompasses cell compositions containing lymphocytes obtained from a first individual that have been depleted of reactivity to the antigens of a second individual. The depletion will preferably have been performed by one of the methods described above involving the indicated possible combinations of steps A–D. Such methods include the use of both cellular and non-cellular antigens for step B and the optional use of step D (i.e., administering bone marrow cells derived from the second individual to the first individual). Thus the compositions can contain 20%–100%, 30%–100%, 50%–100%, 70%–100%, or 90–100% of cells derived from (i.e., endogenous to) the first individual. The cells of the compositions will be suspended in a physiological solution, e.g., a saline solution, and provided in an appropriate container, e.g. a blood bag, a semipermeable blood bag, a tissue culture receptacle such as a tissue culture flask, or a bioreactor. The lymphocyte source (e.g., blood, bone marrow, spleen, or lymph nodes) can be obtained from the first individual, at the appropriate stage of depletion, and purified or enriched by methods familiar to those in the art.

It is envisaged that "batches" of such cell compositions can be made and stored by a supplier using lymphocytes from appropriate human or non-human (e.g., pigs and non-human primates) donors. The lymphocytes can be depleted, using as step B, for example, single or combinations of tumor cell lines stably transfected with and expressing combinations of all known MHC genes. In this way, batches of lymphocytes would be derived, each being tolerant to a different set of HLA antigens. These custom pretolerized batches of lymphocytes can then be supplied to a practitioner (e.g., an oncologist) whose patient is in need of the therapy after communication of the patient's HLA haplotype to the supplier.

If it is proposed to carry out the tolerogenic method of the invention prior to non-syngeneic cell therapy, the practitioner can be supplied with a source of antigenic material (e.g., hemopoietic cells) for use in step 2 of the tolerogenic protocol. This antigenic material can be derived from the individual from which the lymphocytes used for cell therapy were obtained, or from an individual syngeneic with the individual. Alternatively, either cells (e.g., non-malignant hemopoietic cells) stably transfected with appropriate HLA genes or cell extracts of either malignant or non-malignant cells similarly transfected can be used.

(vii) Methods of Cell Therapy

Also within the scope of the invention are methods of treatment that include administration of the above cell compositions to a subject, preferably a human patient. As indicated above, such subjects may optionally have been subjected to one of the described tolerogenic regimes. Patients to which the treatment can be given include cancer patients (e.g., those with the above-listed tumors), patients suffering from infectious diseases such as HIV AIDS or hepatitis B or C, genetic diseases associated with protein (e.g., hemoglobin or an enzyme) deficiencies or abnormalities, aplastic anemia, congenital immunodeficiencies, and autoimmune diseases such as rheumatoid arthritis, multiple sclerosis, insulin-dependent diabetes mellitus, lupus erythematosus, and myasthenia gravis.

Where cells depleted of responsiveness (and/or with enhanced tumoricidal or tumoristatic activity) are used for cell therapy, one or more other populations of cells can be given to the recipient at the same time or at a different time (i.e., before or after administration of the "depleted" cells). The other cell populations can be given, for example, about 1–12 hours, about one day, about two days, about three days, about four days, about five days, about a week, about two weeks, about three weeks, about a month, or about two months before or after the depleted cells. Other cells that can be administered include cell populations containing lymphocytes activated by any of the T cell activators referred to herein or unactivated cell populations containing lymphocytes that have not been depleted by any of the regimens described above. Where more than one cell population is administered to the recipient, the different populations can be derived from different individual donor mammals or the same donor mammal.

Non-syngeneic therapy can be augmented by the administration to the host mammal of a preparation containing one or more (e.g., two, three, four, five, six, seven, eight, or ten) antibodies that bind to molecules on host cells (e.g., tumor cells or lymphoid cells that are involved in autoimmune diseases) that are the targets of effector cells in the donor populations used for the therapy. While the invention is not limited by any particular mechanism of action, such antibodies could exert the effect by facilitating antibody-dependent cellular cytolyis (ADCC), complement-mediated lysis, opsinization and enhanced cytolysis or phagocytosis by phagocytic cells such as monocytes or macrophages, or a combination of two or all three mechanisms. Appropriate antibodies include, without limitation, those specific for CD20 (useful, for example, in treating non-Hodgkin's lymphoma and B cell malignancies), Her2/neu (useful, for example, in treating Her2/neu expresing breast cancer), carcino-embryonic antigen (CEA) (useful, for example, in treating CEA expressing tumors of the gastrointestinal tract, mucin 1 (MUC1) (useful, for example, in treating MUC 1 expressing tumors such as lung cancer).

In addition, prior to, or during non-syngeneic cell therapy, recipient target cells (e.g., tumor cells) can be rendered more susceptible to the effector mechanisms employed by the effector cells in the cell populations used for the therapy by administering to the recipient one or more agents that increase expression of antigenic molecules (e.g., MHC class I and/or MHC class II molecules) expressed on the surface of the target cells. Appropriate agents include, without limitation, IFN-α and IFN-γ.

(viii) Articles of Manufacture

Also encompassed by the invention are articles of manufacture including packaging material (e.g., a cardboard box) containing a biological cell container such as those listed above. The biological container contains any of the cell compositions described above and the packaging material can include a package insert or a label indicating that the composition is to be used in a method of treatment comprising administering of the composition to a mammal in need of the composition (e.g., patients with any of the diseases listed above).

The invention will be further understood with reference to the following illustrative embodiments, which are purely exemplary, and should not be taken as limiting the true scope of the present invention as described in the claims.

EXAMPLE 1

Materials and Methods

Animals

Inbred BALB/c (H-$2^d$), C57BL/6 (B6) (H-$2^b$), DBA/2 (H-$2^d$, CBA (H-$2^k$), B10.D2 (H-$2^d$), SJL (H-$2^s$), and (BALB/c×C57BL/6)F$_1$ (F1) (H-$2^{d/b}$) mice and Lewis rats were purchased from the Hebrew University Hadassah Medical School Animal Facility in Jerusalem, Israel, with breeding pairs originating from Harlan-Olack, Bicester, UK. Two to three month-old mice were used for the study. Mice were kept under standard conditions with food and water provided ad lib. Most of the experiments were carried out in B6→BALB/c strain combination.

Total Lymphoid Irradiation (TLI)

Mice were anesthetized and then positioned in an apparatus designed to expose the major lymph nodes, thymus, and spleen to ionizing irradiation, while shielding most of the skull, ribs, lungs, hind limbs and tail with lead, as previously described. Slavin et al., *J. Exp. Med.*, 146:34 (1977). Radiation was delivered by a Phillips X-ray unit (250 kv, 20 mA) at a rate of 70 cGy/min, using a Cu 0.2-mm filter. The source-to-skin distance was 40 cm.

Tolerogenic Treatment

The basic protocol for conditioning prior to transplantation included sTLI (1–6 daily exposures of 200 cGy) to a total dose of up to 1,200 cGy, followed by intravenous inoculation with 3×10$^7$ BMC on the day after the last TLI dose. Some mice (see Example 9) were not administered any sTLI. One day after BMC infusion, experimental mice were injected with 200 mg/kg Cy (Taro, Israel) intraperitoneally. Cy was freshly dissolved in sterile phosphate-buffered saline prior to injection. Modifications of the Cy protocol to induce tolerance to xenografts are described in Example 8. A second infusion of donor BMC, after Cy, was also administered in some of the mice.

Preparation of Bone Marrow and Spleen Cells

Single cell suspensions of BMC and spleen cells were prepared in PBS or RPMI 1640 medium supplemented with 100 µg/ml streptomycin and 100 U/ml penicillin (Biological Industries, Beit Haemek, Israel). BMC were infused into the lateral tail vein in a total volume of 0.5 ml.

Preparation of Blood Cells for Infusion

Pooled fresh blood was collected into heparin-containing tubes (preservative-free). Each recipient was infused with 0.5 ml into the lateral tail vein.

T cell Depletion of BMC With Monoclonal Antibodies

Monoclonal rat anti-mouse Thy1 antibodies (YTS 148.3, IgM and YTS 154.7, IgG2b) were obtained from Dr. H. Waldmann (Oxford University, UK). BMC (10$^7$/ml) were incubated with YTS 148.3 antibody at a final dilution of 1:200 for 40 min, washed and incubated with Low-Tox rabbit complement (Cedarlane, Canada) at a final dilution of 1:10 for an additional 60 min at 37° C., washed and injected intravenously into recipients. YTS 154.7 antibody was used for depletion of T cells from BMC in vivo; BMC (3×10$^6$/ml) were incubated with 750 µg, 150 µg or 30 µg of the antibody for 60 min at 4° C. and the mixture was injected intravenously into recipients.

Skin Grafting

Skin grafting was carried out 20 days after completion of the tolerogenic treatment. A full-thickness skin graft measuring 1 cm×1 cm was adjusted to the graft bed by 4 Thomas surgery clips (Thomas Scientific, USA). The panniculus carnosus was kept intact in the graft bed. The graft was considered to be accepted when hair of donor color grew on the soft flexible underlying skin, and rejected when donor epithelium was lost.

Implantation of Bone Marrow Plugs

The femora of B6 mice were freed of muscle and irradiated with 400 cGy in vitro to eliminate most of the hematopoietic cells. Marrow plugs were mechanically pressed out of the femur canal with a mandrin and 2 plugs were implanted under the left kidney capsule of each recipient, as described in Chertkov et al., *Rad. Res.* 79, 177–186 (1979).

Heterotopic Heart Grafting

Hearts of 1–2 day old B6 mice were transplanted into the ear skin pocket 20 days after tolerogenic treatment, according to the methods of Chernyakhovskaya et al., *Transplantation*, 29:409 (1980). An ECG was first recorded two weeks after grafting and thereafter at weekly intervals.

Polymerase Chain Reaction (PCR)

PCR was carried out on material derived from blood samples as described previously. Pugatsch et al., *Leukemia Res.* 17, 999–1002 (1993). Briefly, blood samples were lysed in distilled water and centrifuged at 12,000 x g. Supernatants were discarded and 50 µl of 0.05 M NaOH were added to the cell pellets. Samples were boiled for 10 min., then 6 µl of 1 M Tris (pH 7.2) were added. Samples were then centrifuged at 12,000×g and supernatants were used for assay. The 5'-αnd 3'-oligonucleotide primers chosen for amplification and the PCR reaction conditions are described in Pugatsch et al. Reaction products were visualized on 1.6% agarose gels (Sigma, USA) containing 0.05 µg/ml ethidium bromide.

Murine BCL1

BCL1, a B-cell leukemia/lymphoma of BALB/c origin (Slavin, S. and Strober, S. *Nature*, 272:624 (1978); Slavin, S. et al. *Cancer Res.*, 41:4162 (1981)), was maintained in vivo by serial passage in BALB/c mice. Inoculation of 10 to 100 BCL1 cells in BALB/c mice results in typical B-cell leukemia/lymphoma characterized by splenomegaly, extreme peripheral blood lymphocytosis (up to 500,000 lymphocytes/ml) and death of 100% of recipients. BCL1 also causes leukemia in F1 recipients, but development takes longer than in BALB/c recipients (Slavin et al. (1981), supra).

Immunization of Donor Mice

Donor C57BL/6 (H2-$^b$) mice were immunized against alloantigens of both he MHC and Minor Histocompatibility Loci (MiHL) by injection with either spleen cells obtained from BCLL -bearing BALB/c (H-2$^d$) mice (30×10$^6$ cells per mouse per immunization) or spleen cells obtained from normal BALB/c mice (30×10$^6$ per mouse). Donor B 10.D2 (H-2$^d$) mice were immunized against MiHL alloantigens only by injection with the same cell populations used for immunization of the C57BL/6 mice. Immunizations were by intraperitoneal injection on days −20 and −10 prior to sacrifice, harvesting of spleens, and transfer of isolated spleen cells to F1 or BALB/c host animals.

Total body irradiation (TBI)

Mice were conditioned by TBI with a single dose of 400 cGy delivered by linear accelerator (Varian Climac 6 X) at a source to skin distance of 80 cm, at a dose rate of 170 cGy/min.

Transplantation of spleen cells for immunotherapy of BCL1

Spleens from C57BL/6 or B10.D2 donors immunized using the protocols described above were teased into single cell suspensions using nylon meshes, washed twice with 10% bovine calf serum in RPMI 1640 medium (Biological Industries, Beit Haemek, Israel), and injected intravenously.

GVL Effects Against BCL1

Assays for assessing induction of GVL were performed as follows. For testing GVL across an incompatibility involving both MHC and MiHL alloantigens, total of 10$^4$ fresh BCL1 cells and 30×10$^6$ spleen cells obtained from the immunized or control unimmunized C57BL/6 donors were infused into F1 recipients 24 h after TBI. For testing GVL across an incompatibility involving only MiHL alloantigens, a total of 2×10$^3$ BCL1 and 30×10$^6$ spleen cells obtained from immunized or control unimmunized B10.D2 donors were infused into BALB/c recipients 24 h after TBI. Administration of a known tumor cell number allowed quantitative measurement of GVL effects.

Assay for chimerism

Chimerization of BALB/c or F1 recipients by C57BL/6 spleen cells was measured by testing the percentage of host or donor-type cells in spleen or blood samples using an in vitro complement-dependent microcytotoxicity assay with specific alloantisera and rabbit complement. Morecki et al. *J. Exp. Med.*, 165:1468 (1987). Specific alloantisera ("BALB/c anti-C57BL/6" and "C57BL/6 anti-BALB/c") were prepared by cross-immunization of the relevant mice with full-thickness skin allografts followed by 6 intraperitoneal injections of 30×10$^6$ donor spleen cells at intervals of 1–2 weeks. Mice were bled and sera stored at −70° C.

Spleen or peripheral blood cells from the BALB/c or F1 recipients were incubated with both alloantisera and rabbit complement. Host BALB/c cells were lysed with anti-BALB/c and not anti-C57BL/6 antisera, host F1 cells were lysed with both anti-BALB/c and anti-C57BL/6 antisera, and cells in the BALB/c F1 mice derived from the C57BL/6 donor mice were lysed by only anti-C57BL/6 antiserum. Chimerism was expressed as % donor type (C57BL/6) cells which was calculated as follows: % donor type (C57BL/6) cells=% cells lysed with anti-C57BL/6 antiserum-% cells lysed with anti-BALB/c antiserum-% cells lysed with complement alone.

Serial PBL counts for Monitoring Development of BCL1-leukemia

Peripheral blood samples (20 μl) were obtained by weekly venipuncture using heparinized glass capillaries. Peripheral blood leukocyte (PBL) counts were determined using a hemocytometer after lysis of red blood cells in 2% acetic acid.

Detection of residual BCL1 cells by adoptive transfer

An in vivo assay was used for detection of residual BCL1 cells in treated experimental mice. Aliquots of 10$^5$ lymphocytes obtained from a pool of spleen cells from treated mice with no evidence of disease were adoptively transferred to normal secondary BALB/c recipients (10 mice per group). The development of leukemia was determined by weekly peripheral blood lymphocyte (PBL) counts, monitoring spleen enlargement, and survival.

Monitoring of GVHD

Recipients were monitored for survival and clinical signs of GVHD such as ruffled fur, diarrhea, and measurable weight loss. At the time of adoptive transfer, samples of liver and lung sections were obtained form each mouse to test for histological evidence of GVHD. Histological preparations were analyzed by an independent pathologist on a double blind basis.

Cytokine assays

The levels of interferon-γ (IFN-γ), tumor necrosis factor-α (TNF-α), interleukin-2 (IL-2), interleukin-4 (IL-4) and interleukin-10 (IL-10) were measured in supernatants of donor (C57BL/6) spleen cells at the time of harvesting for transplantation to host (recipient) animals. Recipient (F1) spleen cell supernatant cytokine levels were measured at 3 weeks after transplantation of donor C57BL/6 spleen cells. Cytokines were measured by "sandwich" ELISAs using murine cytokine-specific monoclonal antibodies for capture using standard methods familiar to those in the art. Antibodies that bind to cytokine determinants that do not overlap with determinants that bind the capture antibodies and alkaline phosphatase conjugated anti-Ig antibodies were used for detection. Standard curves were generated with standard samples of each cytokine and the concentrations of the cytokines in unknown samples were determined from the standard curves.

In vitro T Cell Proliferation Essays

Mitogen-induced T cell proliferative responses were measured by culturing spleen cells in the presence of the T cell mitogens concanavalin A (ConA, 10 μg/ml) or phytohemagglutinin (PHA, 1 μg/ml) for three days. [$^3$H]-thymidine was added to the cultures for the last 6 hours of culture and T cell proliferation was measured in terms of counts per minute (cpm) of [$^3$H]-thymidine incorporated into the DNA of the cells using cell harvesting and radioactivity techniques known to those in the art.

In vitro Cell-mediated Lysis Assays

Human peripheral blood mononuclear cell (PBMC) and murine spleen or bone marrow populations were tested for their ability to lyse NK-sensitive target cells (human K562 and murine YAC-1 cells) and NK-resistant, activated NK-sensitive target cells (human Daudi and murine P815 cells) using standard $^{51}$Cr-release assays. Briefly, $^{51}$Cr-labeled target cells were incubated at 37° C. with PBMC effector cells at various target cell to effector cell ratios for 4 hours. At the end of the incubation, the cells were pelleted by centrifugation and equal aliquots of supernatant were removed from each assay culture well and counted for radioactivity. Percent lysis was calculated by the following formula:

$$\text{Percent lysis} = \frac{\text{cpm (exp.)} - \text{cpm (cont.)}}{\text{cpm (max.)} - \text{cpm (cont.)}} \times 100$$

Statistical Analyses

The statistical significance of the results comparing treated and control mice was calculated by the independent t-test.

EXAMPLE 2

Nonspecific Immunosuppression of Mice Treated with sTLI Alone or with sTLI and Cy In the first set of experiments (Table 1), BALB/c mice were given 6, 8 or 12 (experimental groups) or 17 (control groups) fractions of TLI at 200 cGy/fraction. After TLI, $3 \times 10^7$ BMC from B6 donors were administered one day after the last TLI. Skin allografts from B6 donors were transplanted 20 days after transfer of the BMC.

In a second set of experiments (Table 2), 5 groups of BALB/c recipients were administered sTLI of 6 fractions of 200 cGy/day, followed a day later with 200 mg/kg Cy intraperitoneally. After the above conditioning, the five groups were treated as described below. Group 1 received $3 \times 10^7$ BMC, whereas group 2 received $3 \times 10^7$ BMC and $5 \times 10^6$ spleen cells. Group 3 received 0.3 ml of whole blood. Group 4 received $3 \times 10^6$ BMC, whereas group 5 received $3 \times 10^6$ T cell depleted BMC. T cell depletion was performed in vitro with monoclonal antibody Thy 1 and rabbit complement, as described in Example 1. For all of the above five groups, cells and whole blood were from B6 donors and were infused intravenously. Skin allografts were transplanted 20 days after BMC or blood transfer.

RESULTS

A short course of TLI (sTLI), in contrast to a long course of TLI (17 fractions, 200 cGy each), was insufficient for acceptance of stem cells from allogeneic BMC or blood. Table 1 shows that none of the BALB/c mice receiving $3 \times 10^7$ fully mismatched BMC from B6 donors became hematopoietic cell chimeras after 6 fractions of TLI, while consistent acceptance of allogeneic BMC was obtained after 17 fractions of TLI. As shown in Table 1, after treatment with sTLI and allogeneic BMC or allogeneic blood cells, BALB/c recipients stayed alive, none developed GVHD and all rejected B6 skin allografts. Thus, after sTLI alone, sufficient numbers of immunocompetent cells remain in the host to reject a donor allograft.

TABLE 1

Incidence of allogeneic BMC and skin graft acceptance after fractioned total lymphoid irradiation.

| No of TLI Fractions | % of donor cells in blood 100 days after cell transfer[a] | Skin allograft survival >100 days[c] |
|---|---|---|
| 6 | 0 (10)[b] | 0/10 |
| 8 | 0 (3), 56 (1) | 1/4 |
| 12 | 0 (3), 50, 90 | 2/5 |
| 17 | 82, 85, 90 (2), 93 | 5/5 |

[a]BMC ($3 \times 10^7$) from B6 donors were given to BALB/c recipients one day after the last TLI.
[b]Number of mice with the same level of chimerism is given in parentheses.
[c]Skin allografts from B6 donor were transplanted 20 days after cell transfer.

TABLE 2

Skin allograft survival and GVHD related death after transplantation of allogeneic cells and skin graft following sTLI in combination with a single injection of Cy.

| No | Donor Cells[a] day 0 | GVHD related death | Mice survival mean ± SD days | Skin graft survival[c] >100 days |
|---|---|---|---|---|
| 1 | BM $3 \times 10^7$ | 22/24 | 39 ± 8 | 2/2 |
| 2 | BM $3 \times 10^7$ and spleen - $5 \times 10^6$ | 14/14 | 10 ± 3 | NT |
| 3 | Blood 0.3 ml | 7/7 | 30 ± 12 | NT |
| 4 | BM $3 \times 10^6$ | 14/15 | 40 ± 7 | 1/1 |
| 5 | BM $3 \times 10^6$ T cell depleted[b] | 0/7 | >100 | 1/7 |

[a]Cells or whole blood from B6 donors were transferred intravenously to BALB/c recipients after sTLI and Cy.
[b]T cell depletion was performed in vitro with mAb anti Thy 1 and rabbit complement.
[c]Donor skin allografts were transplanted 20 days after cell transfer. NT - not tested.

In sharp contrast, a single injection of Cy (200 mg/kg) given one day after the last fraction of sTLI (6 fractions, 200 cGy each), increased the non-specific immunosuppression and allowed the hosts to accept BMC, spleen and blood cells. However, all recipients developed typical acute GVHD which was lethal in most cases (Table 2). The survival time of the recipients with GVHD appeared to be a function of the number of mature immunocompetent T cells present in the inoculum. Mean survival time of mice inoculated with $3 \times 10^7$ BMC was four times longer as compared with recipients of an equal number of BMC mixed with $5 \times 10^6$ B6 spleen cells (Table 2, groups 1 & 2). Transfer of fewer BMC ($3 \times 10^6$ instead of $3 \times 10^7$) did not prolong survival significantly (Table 2, groups 1 & 4).

GVHD was successfully prevented in the mice of group 5 (Table 2), who received T cell depleted BMC after sTLI and Cy. Although none of these experimental mice developed GVHD and all of them remained alive, all but one rejected donor BMC. Accordingly, prolonged skin allograft survival was observed in only 1/7 recipients.

EXAMPLE 3

Antigen-Specific Elimination of Residual Donor-Alloreactive Host Immunocompetent T Cells Three groups of BALB/c recipient mice were administered sTLI in 6 fractions of 200 cGy/day. Non T cell depleted BMC (day 0) from B6 donors were transferred intravenously to the BALB/c recipients in all three groups. The next day all of the recipients were administered 200 mg/kg of Cy. One group (Table 3, Group 1) received a skin graft from B6 donors at day 20. The second group (Table 3, Group 2) received $3 \times 10^7$ non T cell depleted BMC from B6 donors on day 2 followed by a skin graft at day 20. The third group (Table 3, Group 3) received $3 \times 10^6$ non T cell depleted BMC from B6 donors on day 2 followed by a skin graft at day 20.

Levels of donor cells in blood were assayed in all surviving mice at day 100 according to the protocol of Example 1.

TABLE 3

BM and skin allograft acceptance in experimental mice.
Treatment of Mice after TLIx6

| No | Donor BMC[a] $3 \times 10^7$ day 0 | Cy 200 mg/kg day 1 | Donor BMC day 2 | Skin Grafting day 20 | Donor Cells in Blood day 100 | GVHD Related Death days means ± SD[e] | Skin Survival in Mice Without GVHD day > 100 |
|---|---|---|---|---|---|---|---|
| 1 | + | + | — | + | <20%(8)[d,] 20%, 37% | 2/10 75, 85 | 2/8 |
| 2 | + | + | $3 \times 10^7$ | + | NT | 15/15 35 ± 5 | — |
| 3 | + | + | $3 \times 10^6$ | + | NT | 20/22 67 ± 12 | 2/2 >130, >280 |
| 4 | + | + | $3 \times 10^6$ T Cell Depleted in Vitro[b] | + | 20–50% | 0/6 | 616 132, >270(5) |
| 5 | + | + | $3 \times 10^6$ T Cell Depleted in Vivo[c] | + | 20%–50% | 10/20 48 ± 10 | 10/10 >230(10) |

[a]BM cells from B6 donors were transferred intravenously to BALB/c recipients.
[b]T cell depletion was performed in vitro with mAb YTS 148.3 and rabbit complement. A dose of $2 \times 10^6$ cells/recipient resulted in similar tolerance (data not shown).
[c]T cell depletion was performed in vivo with mAb YTS 154.7.
[d]Number of mice is given in parentheses.
[e]Mean ± SD survival time of mice. NT — not tested.

Results

Most of the mice converted to mixed chimeras with a relatively low number (7%–20%) of donor hematopoietic cells in the blood (Table 3, group 1). Donor non T cell depleted BMC transplanted one day after the Cy engrafted successfully but induced GVHD (Table 3, groups 2, 3).

EXAMPLE 4

Establishment of Stable GVHD-Free Mixed Chimeras by Transfer of Low Dose T Cell Depleted Donor BMC Two groups of BALB/c recipient mice were treated as described in Example 3 except that T cell depleted BMC were administered on day 2 instead of non T cell depleted BMC. One group (Table 3, Group 4) was administered $3 \times 10^6$ of in vitro T cell depleted BMC from B6 donors. A total of $2 \times 10^6$ T cell-depleted BMC was sufficient, as demonstrated in one additional experiment (data not shown). The other group (Table 3, Group 5) was administered $3 \times 10^6$ of in vivo T cell depleted BMC from B6 donors. T cell depletion was performed as described in Example 1.

Results

Elimination of immunocompetent T cells from allogeneic donor BMC was crucial for prevention of GVHD (FIG. 1). In mildly immunosuppressed recipients, after in vitro depletion of T cells from donor BMC, all treated mice converted to stable mixed chimeras with 20%–50% of donor cells in the blood. The stable mixed chimeric mice accepted full-thickness B6 skin allografts and survived for 152–290 days without clinical signs of GVHD (Table 3, group 4). Similar results were obtained using an identical protocol for BALB/c→B6 chimeras with permanent (>150 days) survival of BALB/c skin allografts (data not shown).

Depletion of T cells in vivo from donor BMC was less successful than T cell depletion in vitro (Table 3, group 5). Of the mice that received in vivo T cell depleted BMC, only half remained free of GVHD and survived for >250 days (Table 3, group 5). These animals were all confirmed to be stable mixed chimeras and all accepted donor skin allografts.

EXAMPLE 5

Tolerance to Allografts of Donor BM Stroma and Neonatal Heart

Five groups of BALB/c recipient mice were conditioned with sTLI by administration of 6 fractions of 200 cGy/day. All of these groups then received $3 \times 10^7$ non T cell depleted BMC of B6 donors intravenously one day after the last TLI fraction. A dose of Cy (200 mg/kg) was given one day after the BMC transfer but before allograft transplantation. Twenty-four hours after the Cy, Group 1 (Table 4) was transplanted with non T cell depleted BMC whereas Group 2 (Table 4) was transplanted with in vitro T cell depleted BMC. Group 3 (Table 4) was transplanted with BMC stroma one day after Cy, Group 4 (Table 4) with heart 20 days after Cy and Group 5 with skin 20 days after Cy. All of the allografts were from B6 donors.

TABLE 4

Acceptance of various cell and tissue allografts in hosts conditioned with sTLI, donor-derived bone marrow cells and Cytoxan.

| Group Number[a] | % Donor Cells in Blood Before Allograft Transplantation | Type of Allograft | Allograft Acceptance | Graft Survival Time in days[h] |
|---|---|---|---|---|
| 1 | <20 | BMC | 22/22[g] | 17–25 (20)[h] >150 (2) |
| 2 | <20 | BMC, T Cell depleted | 6/6 | 152, >290 (5) |
| 3 | <20 | BM Stroma[c] | 8/8[e] | >220 (8) |
| 4 | <20 | Heart[d] | 5/6[f] | 80, >155 (4) |

TABLE 4-continued

Acceptance of various cell and tissue allografts in hosts conditioned with sTLI, donor-derived bone marrow cells and Cytoxan.

| Group Number[a] | % Donor Cells in Blood Before Allograft Transplantation | Type of Allograft | Allograft Acceptance | Graft Survival Time in days[h] |
|---|---|---|---|---|
| 5 | <20 | Skin[d] | 0/13 | |
| 6 In vitro T cell depleted BMC[b] 1 day after Cy | 20–50 | Skin[d] | 13/14 | >270 (13) |

[a]Recipients in groups 1–5 were conditioned prior to transplantation with sTLI (6 daily exposures of 200 cGy), 3 × 10$^7$ BMC intravenously one day after the last TLI fraction and 200 mg/kg Cy intraperitoneally one day after cell transfer.
[b]One group of recipients (group 6) were inoculated with a second graft consisting of 3 × 10$^6$ T cell depleted (in vitro) BMC from B6 donors given one day after Cy.
[c]BM plugs were grafted on day after Cy.
[d]Heart muscle or skin allografts were grafted 20 days after Cy.
[e]Ectopic bone formation under the kidney capsule was confirmed by X-ray analysis.
[f]Viability and regular pulsatile activity of heart muscle allografts was confirmed by ECG.
[g]Twenty recipients in group 1 died from GVHD 37–45 days after cell transfer.
[h]Number of mice surviving with allografts is indicated in parentheses.

Results

Mice that were given a second infusion of unmanipulated donor BMC had graft acceptance but 20 of the 22 mice died from GVHD 37–45 days after cell transfer. Mice transplanted with T cell depleted BMC in the second infusion had graft acceptance and much higher graft survival.

Implantation of two femoral plugs from B6 donors under the kidney capsule of BALB/c recipients one day after Cy without a second inoculum of T cell depleted donor BMC resulted in formation of fully developed ectopic bone confirmed by X-ray analysis and subsequently by autopsy. This bone supported both donor and recipient hematopoiesis (Table 4, Group 3). Fragments of the ectopic osteohematopoietic site, when retransplanted under the kidney capsule of normal mice, formed bones and ectopic hematopoietic sites in secondary recipients of donor origin (9/9 successful allografts in B6 recipients) but not in BALB/c mice (0/9). These data indicate that ectopic osteohematopoietic sites in these mice were of donor origin.

The same treatment was also sufficient for acceptance of heterotopically transplanted neonatal heart grafts obtained from 1–2 day old B6 donors. Results show that the heart muscle transplanted into an ear skin pocket of BALB/c recipients 20 days after the tolerogenic treatment were ECG positive for >80 days (Table 4, Group 4). In all mice that accepted donor-derived neonatal heart grafts, contractions of the heart muscle could also be detected visually. Mice that received only sTLI and Cy rejected both femoral plugs and neonatal heart grafts from B6 donors within 30 days (Data not shown).

Most of the recipients that received sTLI, BMC and Cy accepted donor BMC, BM stromal precursor cells and neonatal heart allografts. However, the conditioning was not sufficient to ensure survival of skin allografts obtained from the same donor (Tables 3 & 4).

EXAMPLE 6

Conditions Required for Stable Donor Skin Allograft Acceptance in Mice

A group of mice were administered sTLI, BMC and Cy as described in Example 5. This group (Table 4, Group 6) also received a second inoculation of 3×10$^6$ of B6 in vitro T cell depleted B6 donor BMC one day after Cy but prior to skin allograft.

Results

Mixed hematopoietic cell chimerism was documented among all experimental animals tested, those that accepted as well as those that rejected donor-type skin allograft. However, the level of chimerism was clearly higher in the mice that, after administration of Cy, received donor BMC in suspension or within a BM femoral plug (20%–50% donor cells) as compared with mice that received no second infusion with BMC (<20% donor cells). These data indicate that skin allograft acceptance, which is a strong immunogen, is dependent on the level of hematopoietic cell chimerism in recipients.

Mixed chimeras with 20% or more donor cells in their blood accepted donor skin allografts for >270 days without any additional treatment (Table 4, group 6). Most of the mice that did not receive the second inoculum of donor BMC had less than 20% donor cells in the blood and rejected donor skin allografts (Table 4, group 5). This same group of mice nonetheless accepted other donor-derived tissues. These data demonstrate that although a relatively low number of donor cells in the blood (e.g., less than about 20%) may be sufficient for successful engraftment of marrow-derived stromal cells and heart grafts, consistent acceptance of skin allografts derived from the same donor across strong MHC barriers requires a higher level of hematopoietic cell chimerism.

EXAMPLE 7

Specificity of Transplantation Tolerance Induced by the Tolerogenic Treatment

Tolerant BALB/c recipients with intact B6 skin allografts for 150 days rejected (11/11), within 18–20 days, a second skin allograft obtained from a third party (CBA) donor while keeping intact the original B6 skin allograft. This indicates that donor-type specific transplantation tolerance was induced and maintained in recipients apable of generating normal immune responses with full expression of alloreactivity to on-relevant transplantation antigens.

Acceptance of donor skin allografts was observed in all strain ombinations investigated including, DBA→BALB/c (n=10), B6→CBA (n=3), B6→BALB/c (n=21) and BALB/c→B6 (n=9).

EXAMPLE 8

Application of Tolerogenic Treatment for Induction of Transplantation Tolerance to Skin Xenografts in Rat→Mouse Combination Two groups of mice were administered sTLI of 6 fractions of 200 cGy/day. After sTLI conditioning, both groups were administered 30×10$^6$ non-T cell depleted Lewis rat BMC intravenously. The first group was given a single dose of 200 mg/kg Cy the next day. Another 3×10$^7$ non T cell depleted rat BMC were administered the following day. In the second group, a dose of 60 mg/kg Cy was given daily for 3 days in contrast to the single 200 mg/kg dose given the first group. The first dose of Cy was given 10 hours after the first rat BMC inoculation, the second dose at 24 hours and the third dose at 48 hours (see below). After administration of three doses of 60 mg/kg Cy, a second inoculation of 3×10$^7$ non T cell depleted rat BMC were administered.

Results

The first group of mice treated as described above (Table 5, group 1) accepted the second inoculum of $3 \times 10^7$ non T cell depleted BMC from Lewis rats. Lethal GVHD was induced, however, in most of the recipients, suggesting fast engraftment of donor cells despite the relatively mild and non-myeloablative immunosuppressive conditioning (Table 5, group 1). Interestingly, mice that developed GVHD, indicating acceptance of donor cells, were still capable of rejecting donor-derived skin grafts prior to succumbing to the disease. These results confirm the observation that residual donor-reactive host T cells mediating host vs graft reaction may survive the immunosuppressive/tolerogenic treatment and cause rejection of highly immunogenic donor-derived skin xenografts.

TABLE 5

Tolerance in mice to Lewis rat bone marrow cells and skin xenografts. Treatment of Mice After sTLI Conditioning

| | Day 0 | Day 1 | Day 2 | Day 3 | Skin Graft Acceptance | Skin Xenograft Survival Time in days[d] |
|---|---|---|---|---|---|---|
| Rat BMC[a] | | Cy 200 mg/kg | Rat BMC[c] | | 0/6 | <20 (6) |
| Rat BMC[a] | Cy[b] 60 mg/kg | Cy 60 mg/kg | Cy 60 mg/kg | Rat BMC[c] | 15/20 | >176 (2), 123, >95 (5) >67 (3), 39 (2), 24 (2)[e] |

[a]$3 \times 10^7$ Lewis BMC intravenously.
[b]1st injection with Cy 10 h after the 1st rat BMC inoculation.
[c]$3 \times 10^7$ Lewis BMC intravenously.
[d]In parentheses number of mice keeping rat skin graft for indicated period.
[e]5/8 mice died from GVHD with rat skin xenograft accepted. Seven of 15 mice with intact skin allografts developed no acute GVHD.

The results improved, in the second group, when Cy was divided into three equal doses of 60 mg/kg and injected 10 h, 24 h and 48 h after the first infusion of non-T cell depleted rat BMC. Under these conditions, 15 of 20 B6 recipients accepted full thickness Lewis rat skin xenografts (Table 2, group 2). By modifying the Cy administration protocol, host xenoreactive cells may have been more effectively controlled. Normal donor hair growth was observed in all 15 recipients, 5 of which developed lethal GVHD. The surviving mice did not develop clinical signs of GVHD although they were transplanted with non T cell depleted xenogeneic BMC suggesting that residual host-type hematopoietic cells may down-regulate donor-derived immunocompetent T cells through a veto effect.

EXAMPLE 9

Effect of Varying Doses of TLI on GVHD-Free and Donor-Type Skin Allograft Survival BALB/c mice were treated with 0 to 6 doses of sTLI, with each dose being 200 cGy. After administration of sTLI, one group of mice received Cy (200 mg/kg), followed, one day later, by $3 \times 10^7$ or $3 \times 10^6$ BMC (non-T cell-depleted) obtained from B6 donors. A second group of mice received, one day after sTLI, $3 \times 10^7$ BMC (non-T cell-depleted) from B6 donors. These mice, 24 hours later, were administered Cy (200 mg/kg). One day after the Cy, these mice again received $3 \times 10^7$ or $3 \times 10^6$ non-T cell-depleted BMC also obtained from B6 donors. A third group of mice received, after sTLI, 0.3 ml of blood from B6 donors and, 24 hours later, Cy (200 mg/g). Once again, one day after Cy, $3 \times 10^7$ or $3 \times 10^6$ non-T cell-depleted BMC, obtained from B6 donors, were administered to these mice. Twenty days later, donor B6 skin was grafted into surviving mice of all the groups.

Another set of experiments was conducted to correlate donor cell levels and skin allograft acceptance. The tolerogenic treatment included varying numbers of sTLI doses, followed, a day later, by $3 \times 10^7$ BMC and, 24 hours later, Cy (200 mg/kg). A day after administration of Cy, a second infusion of $3 \times 10^7$ BMC was administered. Donor skin was grafted 20 days later. Percentages of donor blood cells in host mice were evaluated at 100–130 days after skin grafting.

In another set of experiments, sTLI-treated BALB/c mice were tolerized as indicated in Table 6 followed, 20 days later, with donor skin allografts. At either day 100 or day 120, donor cell chimerism was assayed and mixed lymphocyte reaction (MLR) tests were performed. The T cells were then enriched by lysing red blood cells with ammonium chloride, followed by passage through a nylon wool column and reconstituting in RPMI medium supplemented with 10% of AB Human serum, 0.09 mM nonessential amino acids, 1 mM sodium pyruvate, 2 mM glutamine, 100 μg/ml streptomycin and 100 U/ml penicillin (Biological Industries, Beit Haemek, Israel) and 0.05 mM 3-mercaptoethanol (Sigma, USA). $10^5$ responding T cells were incubated with $10^6$ stimulating T cells (3000 cGy irradiated) in flat bottom microplates (Costar, USA) at 37° C., 5% $CO_2$ for 3 days. The cells were pulsed on the third day with 1 μCi [$^3$H] thymidine and harvested on the fourth day.

TABLE 6

MLR reactivity of BALB/c mice that accepted or rejected donor-type skin allografts.

| Mice | Treatment of Mice Tested in MLR[a] | Time After Treatment (Days) | Acceptance of B6 Skin Allograft[b] | Donor Cells in Blood[c] | Responders | MLR with Stimulators Irradiated 3000 cGy (cpm × 10⁻³) | | |
|---|---|---|---|---|---|---|---|---|
| | | | | | | Autologous | B6 | BALB/c |
| 1 | BMC, Cy, $3 \times 10^7$ BMC | 100 | + | 65% | 1 | 2.24 | 1.93 | 2.00 |
| 2 | BMC, Cy, $3 \times 10^7$ BMC | 100 | + | 73%, | 2 | 1.72 | 1.56 | 2.89 |
| 3 | BMC, Cy, $3 \times 10^7$ BMC | 100 | + | 56% | 3 | 1.36 | 2.45 | 3.29 |
| 4 | BMC, Cy, $3 \times 10^6$ BMC | 120 | − | 7% | 4 | 5.80 | 35.45 | 6.56 |

TABLE 6-continued

MLR reactivity of BALB/c mice that accepted or rejected donor-type skin allografts.

| Mice | Treatment of Mice Tested in MLR[a] | Time After Treatment (Days) | Acceptance of B6 Skin Allograft[b] | Donor Cells in Blood[c] | Responders | MLR with Stimulators Irradiated 3000 cGy (cpm × 10$^{-3}$) | | |
|---|---|---|---|---|---|---|---|---|
| | | | | | | Autologous | B6 | BALB/c |
| 5 | BMC, Cy, 3 × 10$^6$ BMC | 120 | – | 12% | 5 | 11.98 | 58.08 | 16.07 |
| 6 | BMC, Cy, 3 × 10$^6$ BMC | 120 | – | 7% | 6 | 14.64 | 28.34 | 11.94 |
| 7 | BMC, Cy, 3 × 10$^6$ BMC | 120 | – | 7% | 7 | 21.15 | 66.17 | 29.66 |

[a]BALB/c mice that received 3 × 10$^7$ BMC from B6 donors and 24 h later, 200 mg/kg Cy were reconstituted with 3 × 10$^7$ BMC (mice 1–3) or with 3 × 10$^6$ BMC (mice 4–7) from B6 donors one day after injection of Cy.
[b]Skin allografts from B6 mice were transplanted 20 days after treatment.
[c]Percentage of donor cell chimerism was assayed on the same day as MLR.

Results

Figure 2:
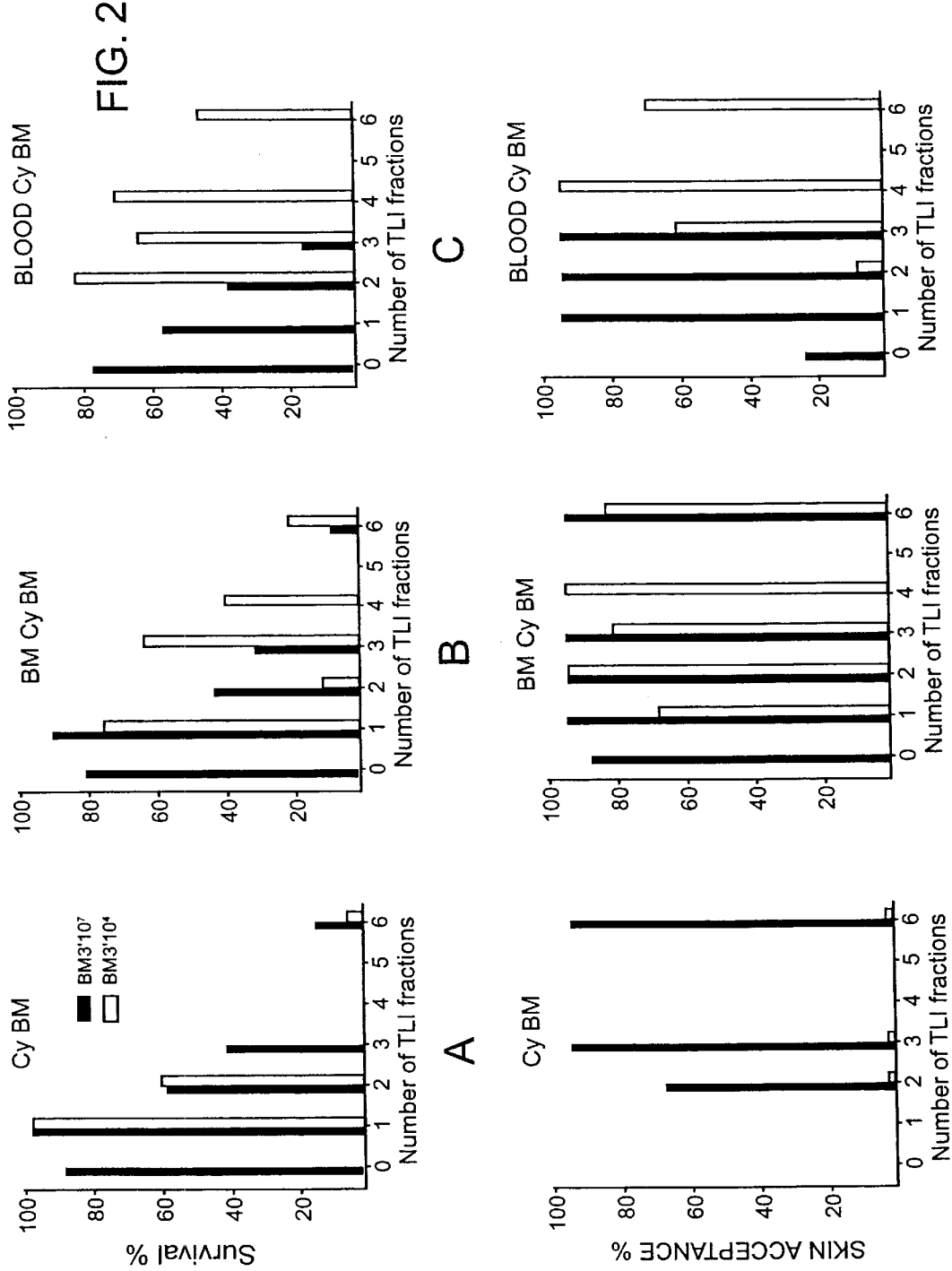
FIGS. 2. (A,B,+C) GVHD-free survival (upper panel) and donor-type skin allograft survival (lower panel) of BALB/c mice irradiated with various number of daily TLI fractions.

In the absence of donor-specific tolerization (FIG. 2A, Group A), 0, 1, or 2 doses of sTLI appeared to be sufficient for a high probability of GVHD-free survival when 3×10$^7$ BMC or 3×10$^6$ BMC were administered subsequent to the Cy treatment. Administration of these low doses of sTLI to a host results in retention of relatively high numbers of host functional T cells. Consequently, the relatively high rate of GVHD-free survival at low sTLI doses may be due to a veto effect in which the levels of host-and donor-derived veto cells are in balanced equilibrium. Donor skin graft acceptance was low at 0 and 1 sTLI dose but increased at 2, 3, and 6 sTLI doses (data not available for 4 and 5 sTLI fractions). However, the GVHD-free survival rate decreased at these doses of sTLI. (FIG. 2A). Thus, in the absence of donor-specific tolerization, none of the regimens led to a high percentage of GVHD-free survival and a high percentage of donor skin graft acceptance.

Donor-specific tolerization in the second group of mice (FIG. 2A, Group B) resulted in high GVHD-free survival at low doses of sTLI, and even with no TLI treatment. The donor-specific tolerization also resulted in a high probability of donor skin allograft acceptance regardless of the number of sTLI doses. Without any sTLI fractions, a second dose of 3×10$^7$ BMC appears to be necessary. The use of higher numbers of sTLI fractions resulted in higher GVHD morbidity, although skin allograft acceptance remained high. With regards to GVHD, the higher numbers of sTLI fractions seem to be more successful with a lower dose (3×10$^6$) of BMC. This may be due to a veto effect in which lower numbers of host veto cells, due to administration of higher numbers of sTLI fractions, are in balanced equilibrium with a lower dose of BMC.

The infusion of 0.3 ml of blood, without any TLI, in the third group of mice (FIG. 2C, group C) resulted in a high probability of GVHD-free survival but low donor skin allograft acceptance. This third group of mice had high GVHD-free survival when 0, 1, or 2 fractions of sTLI were administered and the mice received a large dose of (3×10$^7$) BMC following Cy. However, higher numbers of sTLI fractions were more successful with a smaller dose of (3×10$^6$) BMC following Cy. These results may be due to a veto effect as discussed above for the second group of mice.

Figure 3:
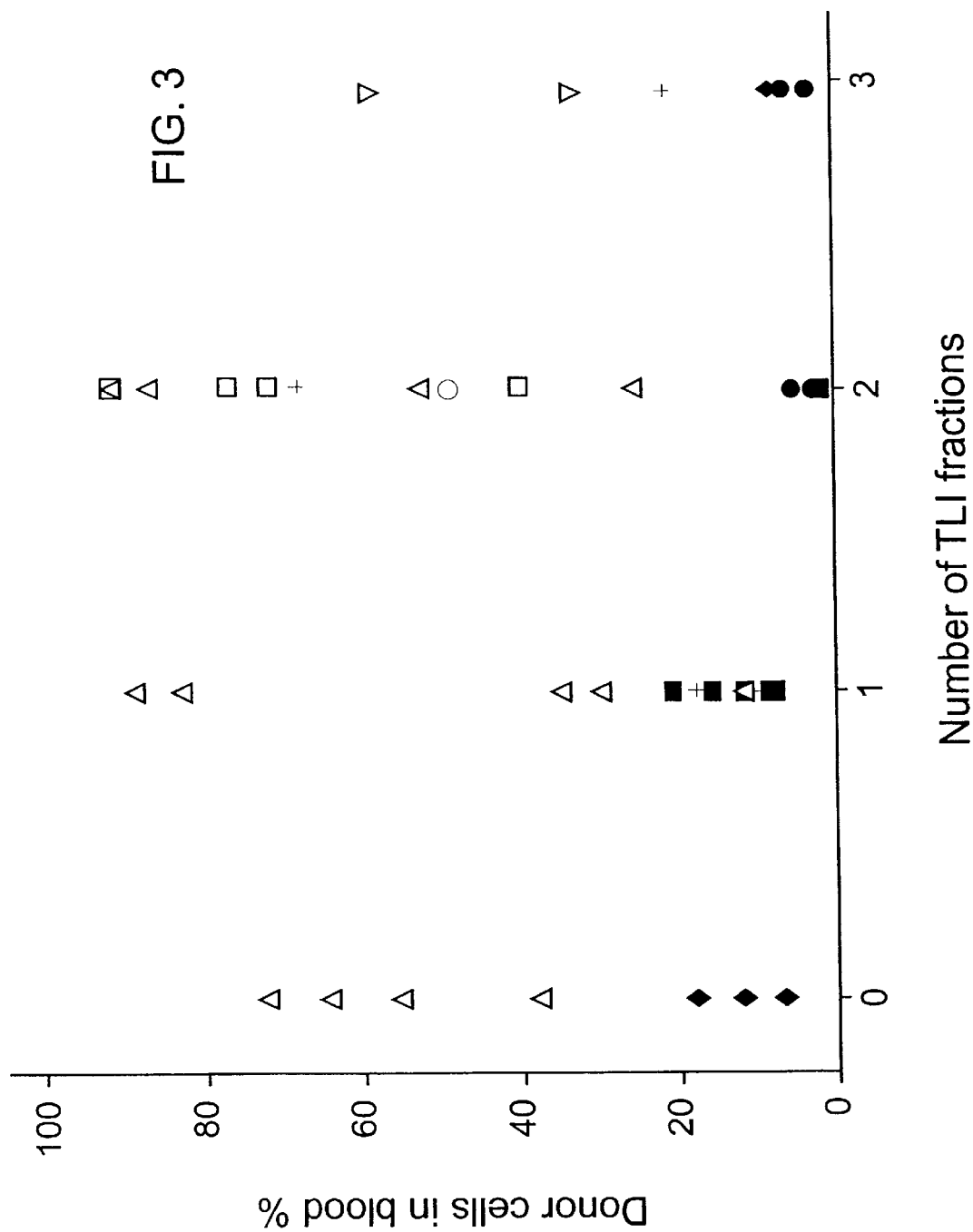
FIG. 3. Xenograft survival of Lewis rat skin in B6 mouse recipients following a non-myeloablative tolerogenic protocol based on the use of sTLI, donor BMC and Cy.

The correlation between the percentages of donor blood cells in a recipient and donor-skin allograft acceptance is illustrated in FIG. 3. These experiments indicated that the percentage of donor blood cells in the recipient was critical for skin allograft acceptance. Recipients with less than 20–25% donor blood cells did not accept donor-skin allografts (solid symbols). In contrast, recipients having greater than 20–25% donor blood cells accepted donor-skin allografts (empty symbols). Furthermore, recipients were able to obtain greater that 20–25% of donor blood cells even when conditioned with 0, 1, 2, or 3 sTLI fractions in the tolerogenic treatment.

MLR reactivity data (Table 6) indicated that mice with low levels of chimerism (mice 4–7) were not completely tolerized. The responder T lymphocytes proliferated in the presence of stimulators from autologous, BALB/c and B6 sources. The response to B6 stimulators was especially high. In contrast, mice with high levels of chimerism (mice 1–3) did not respond to stimulators from any of the sources.

EXAMPLE 10

Immunized Donor Spleen Cells Induce Stronger GVL Effects Across an MHC Barrier than Unimmunized Spleen Cells In order to measure GVL activity across an incompatibility involving both MHC and MiHL alloantigens, F1 mice (pre-conditioned on day 0 with TBI (400cGY)) were injected on day 1 with 10$^4$ BCL1 cells and 30×10$^6$ immunized or normal C57BL/6 spleen cells.

There were 4 test groups with 10 mice in each:
Group 1: F1 recipients given BCL1 cells and spleen cells from C57BL/6 mice immunized with spleen cells from overtly leukemic BCL1-bearing mice.
Group 2: F1 recipients given BCL1 cells and spleen cells from C57BL/6 mice immunized with normal BALB/c spleen cells.
Group 3: F1 recipients given BCL1 cells and normal C57BL/6 spleen cells.
Group 4: Untreated F1 recipients given BCL1 cells only and thereby serving as a control group.

Results

Figure 4:
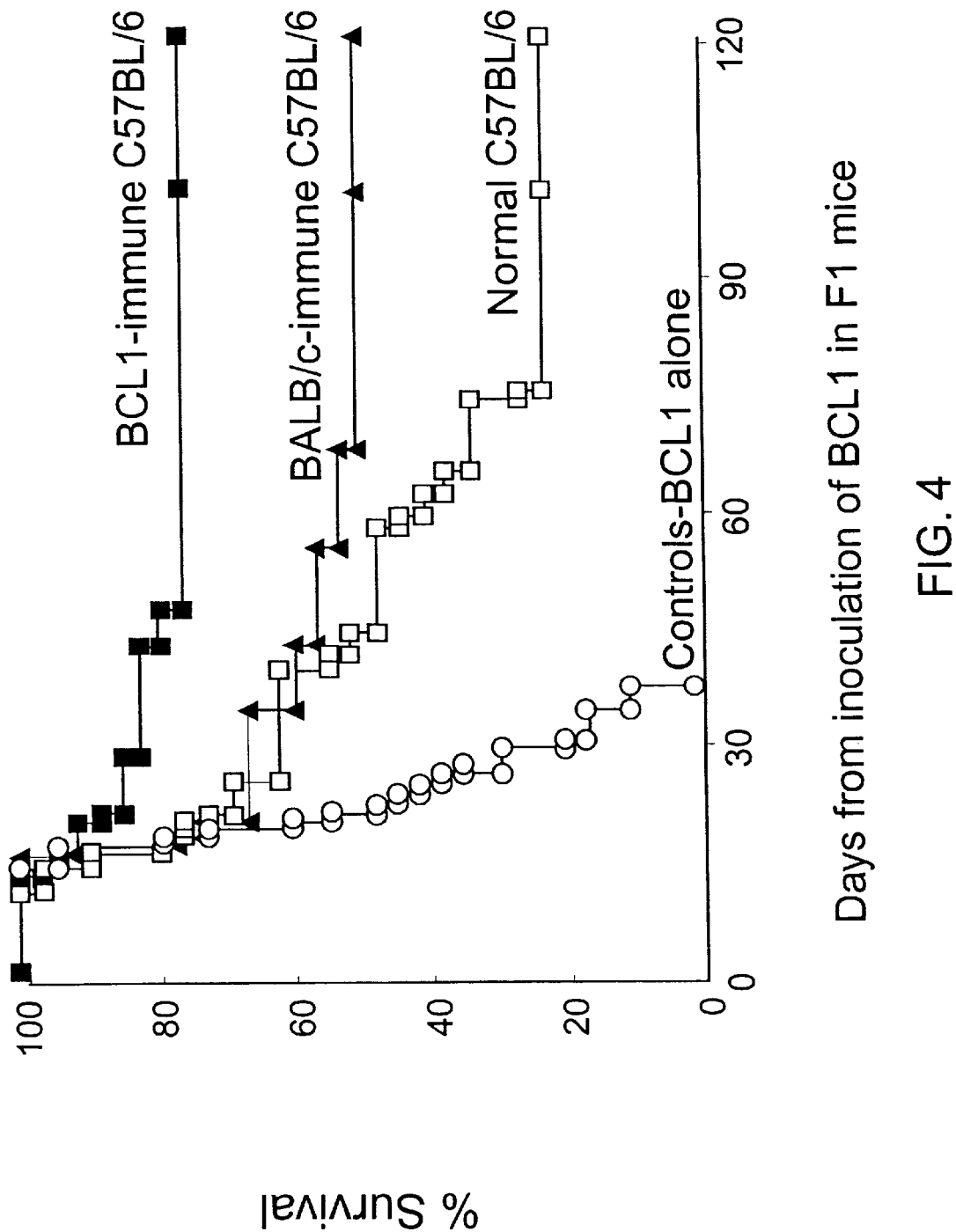
FIG. 4. Survival of host F1 mice after injection of BCL1 tumor cells and lymphoid cells from either immunized or non-immunized B6 donor mice incompatible with the host mice at both the MHC and MiHL.

FIG. 4 shows cumulative data from 4 similar experiments. 75% of the mice in the 1st group and 48% of the mice in the 2nd group were alive after 120 days with no evidence of leukemia. The data described in the following paragraph and shown in FIG. 5 indicate that the 25% of mice in group 1 that died before 120 days, died of GVHD rather than leukemia. In contrast, 79% of the mice in the 3rd group died of GVHD within 75 (median 56) days. All mice in group 4 died of leukemia within 36 (median 24) days. The therapeutic advantage of BCL1-immunized C57BL/6 spleen cells over BALB/c spleen cell-immunized C57BL/6 spleen cells and BCL1-immunized spleen cells over normal, unimmunized C57BL/6 spleen cells was significant (p=0.001 and 0.002 respectively). Although F1 mice given spleen cells from BALB/c spleen cell-immunized C57BL/6 mice apparently had a higher survival rate compared with F1 mice treated with normal, unimmunized C57BL/6 spleen cells (FIG. 4), the advantage was not significant (p=0.083).

Figure 5:
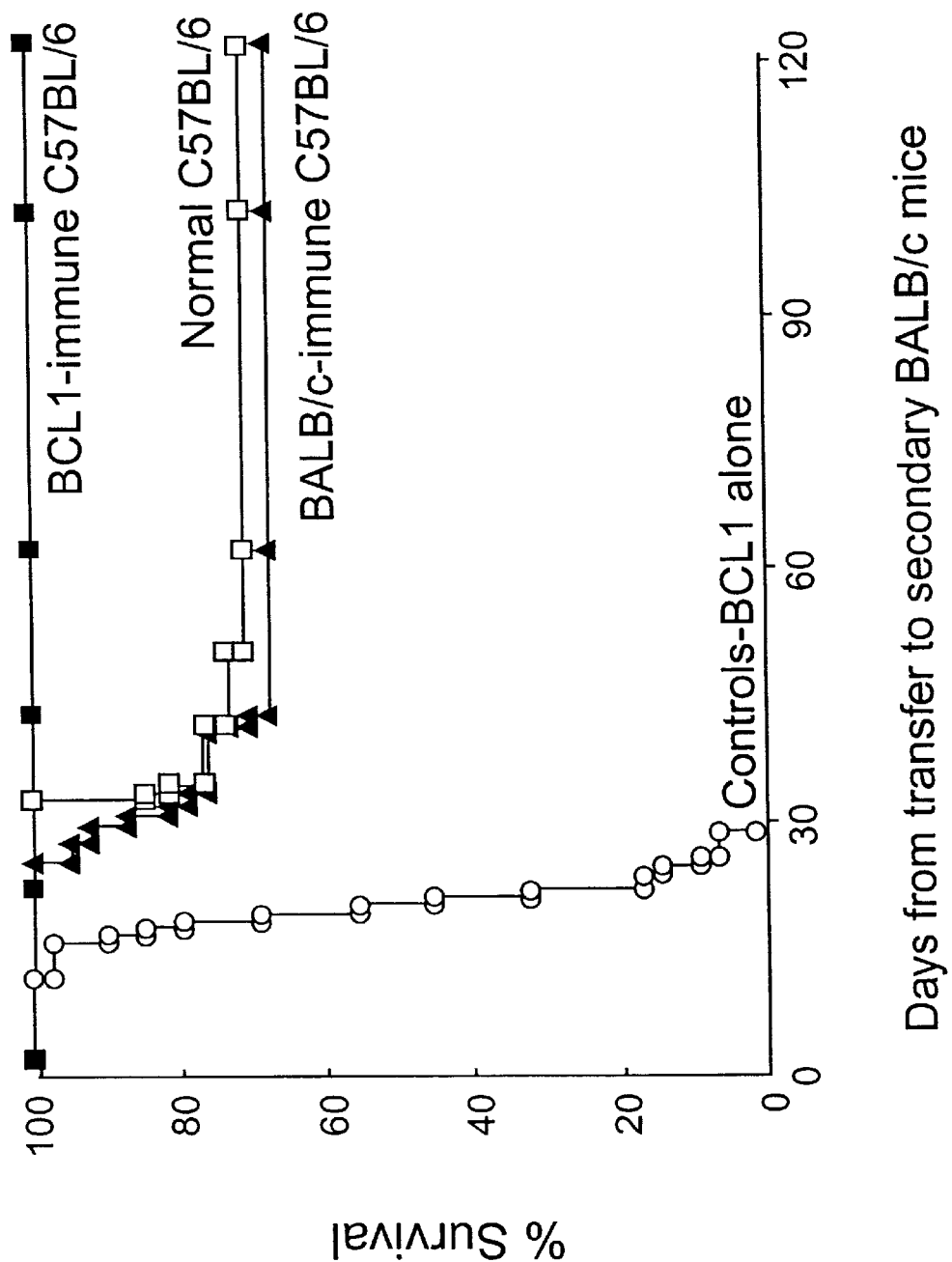
FIG. 5. Survival of secondary BALB/c host mice after transfer of spleen cells from primary F1 host mice injected with BCL1 tumor cells and lymphoid cells from either immunized or non-immunized B6 donor mice incompatible with the host mice at both the MHC and MiHL.

To measure the efficacy of allogeneic cell therapy in eradicating residual BCL1 cells, spleen cells obtained 3 weeks post transplantation were pooled from each experimental group and $10^5$ cells were adoptively transferred to secondary BALB/c recipients (10 mice/group) (FIG. 5). The results were consistent with those obtained in the primary F1 recipient mice. The GVL effect of BCL1-immunized spleen cells was more potent than that of both BALB/c spleen cell-immunized C57BL/6 spleen cells (p=0.001) and normal, unimmunized C57BL/6 spleen cells (p=0.004). The BALB/c spleen cell-immunized C57BL/6 spleen cells showed no greater anti-tumor activity than normal, unimmunized C57BL/6 spleen cells (p=0.5). All the secondary recipients inoculated with spleen cells obtained from the 1st experimental group remained leukemia-free for >120 days. 25 of 40 secondary BALB/c recipients inoculated with spleen cells obtained from the 2nd experimental group remained leukemia-free for >120 days, and 27 of 40 secondary BALB/c recipients inoculated with spleen cells obtained from the 3rd experimental group remained leukemia free for >150 days. In contrast, all 28 secondary BALB/c recipients of spleen cells obtained from the control group died of leukemia within less than 30 days. PBL taken from F1 recipients showed 46–56% donor-type cells, confirming engraftment (Table 7).

TABLE 7

Chimerism in F1 recipients transplanted with C57BL/6 spleen cells.

| F1 Mice Injected with Spleen Cells From: | Donor Type Cells (%) |
|---|---|
| C57BL/6 mice immunized with BCL1 | 50 ± 12 |
| C57BL/6 mice immunized with BALB/c spleen cells | 46 ± 14 |
| Normal C57BL/6 mice | 56 ± 16 |

Figure 6:
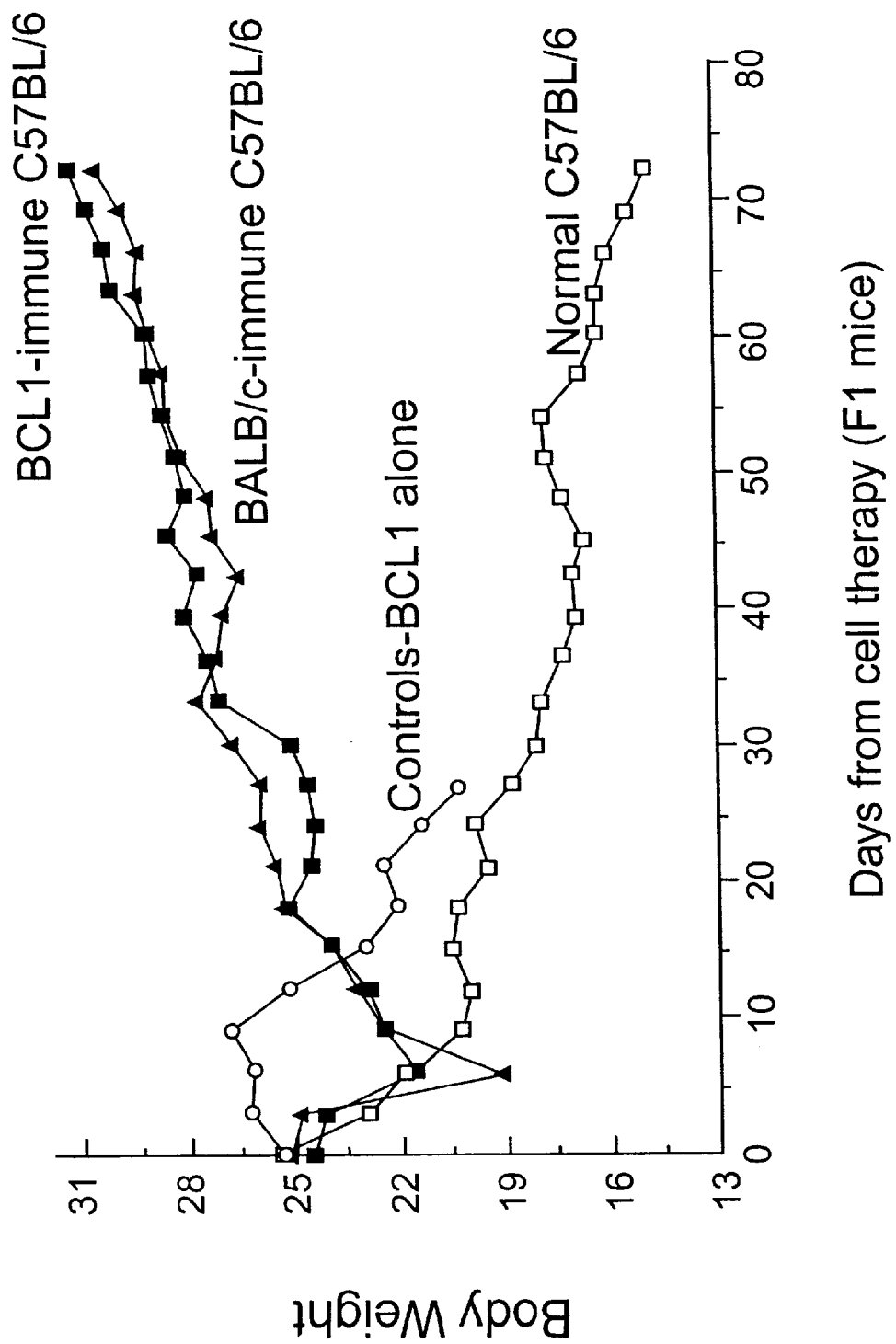
FIG. 6. Body weight changes in F1 host mice after injection of BCL1 tumor cells and lymphoid cells from either immunized or non-immunized B6 donor mice incompatible with the host mice at both the MHC and MiHL.

Body weight studies of the mice in each group, as an objective measure of the degree of GVHD, are shown in FIG. 6. All mice had severe GVHD in the first 2 weeks after transplantation and a proportion of the animals in each group did not survive. However, 75% of the mice in the 1st group and 48% of the 2nd group remained active and well with no evidence of GVHD at 120 days. All animals in the 3rd group died within 75 (median 56) days with typical signs of acute GVHD. F1 mice that were given normal C57BL/6 spleen cells showed typical clinical signs of GVHD manifested by a continuous weight loss, whereas transient reduction in body weight for only one week was observed for F1 mice receiving C57BL/6 spleen cells obtained from donors immunized against either BCL1 or normal BALB/c spleen cells.

EXAMPLE 11

Immunized Donor Spleen Cells Induce Stronger GVL Effects Aacross an MiHL Barrier than Unimmunized Spleen Cells In order to determine the GVL effects across MiHL incompatibility, BALB/c recipients (conditioned on day 0 with TBI (40OcGy)), were injected intravenously on day 1 with $2 \times 10^3$ BCL1 cells and $30 \times 10^6$ spleen cells from either B10.D2 mice pretreated in one of three ways or no B10.D2 spleen cells. There were 4 experimental groups with 10 mice in each:

Group 1: BALB/c recipients given BCL1 cells and spleen cells from B10.D2 immunized with BCL1 cells obtained from BALB/c.

Group 2: BALB/c recipients given BCL1 cells and spleen cells from B10.D2 mice immunized with normal BALB/c spleen cells.

Group 3: BALB/c recipients given BCL1 cells and normal B10.D2 spleen cells.

Group 4: Untreated BALB/c recipients given BCL1 cells only and thereby serving as a control group.

Results

Figure 7:
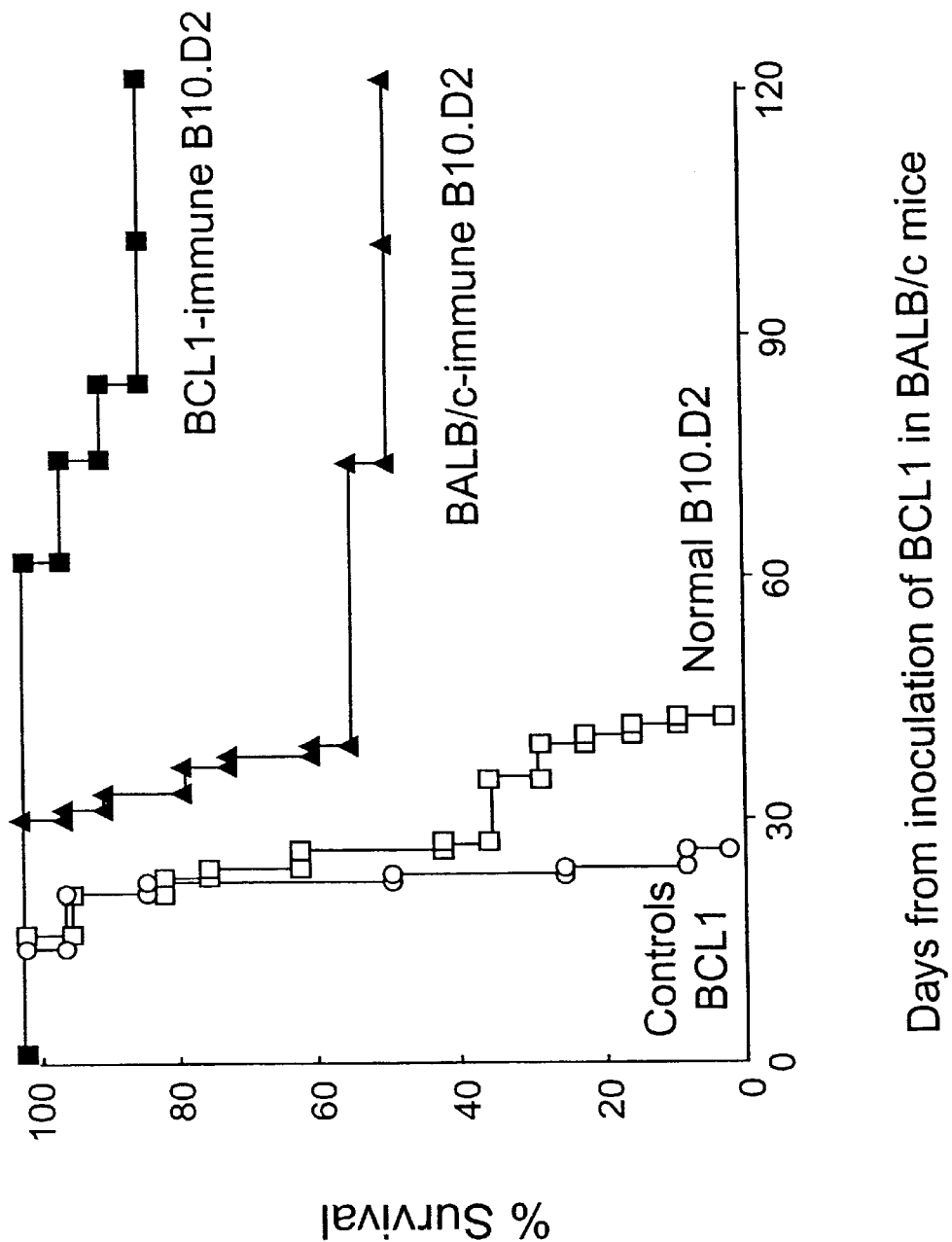
FIG. 7. Survival of host BALB/c mice after injection of BCL1 tumor cells and lymphoid cells from either immunized or non-immunized B10.D2 donor mice incompatible with the host mice at MiHL only.

As summarized in FIG. 7, 84% of the mice in the 1st group were alive with neither signs of clinical GVHD nor leukemia for >120 days. Similarly, 47% of the mice in the 2nd group were alive with no sign of GVHD or leukemia for >120 days, whereas 16 of 30 died of leukemia. All mice in the third and fourth groups died of leukemia. There was a significant therapeutic advantage of treating the recipient BALB/c mice with spleen cells from BCL1-immunized B10.D2 mice over treatment with either spleen cells of BALB/c spleen cell-immunized B10.D2 mice (p=0.03) or spleen cells from naive, unimmunized B10.D2 mice (p<0.002)

(FIG. 7). There was also a significant therapeutic advantage in administering spleen cells from BALB/c spleen cell-immunized B10.D2 animals over administering spleen cells from naive, unimmunized B10.D2 mice (p=0.0001). Spleen cells from BCL1-immunized B10.D2 mice displayed greater GVL-mediated therapeutic efficacy than did those from BALB/c spleen cell-immunized B10.D2 mice.

Figure 8:
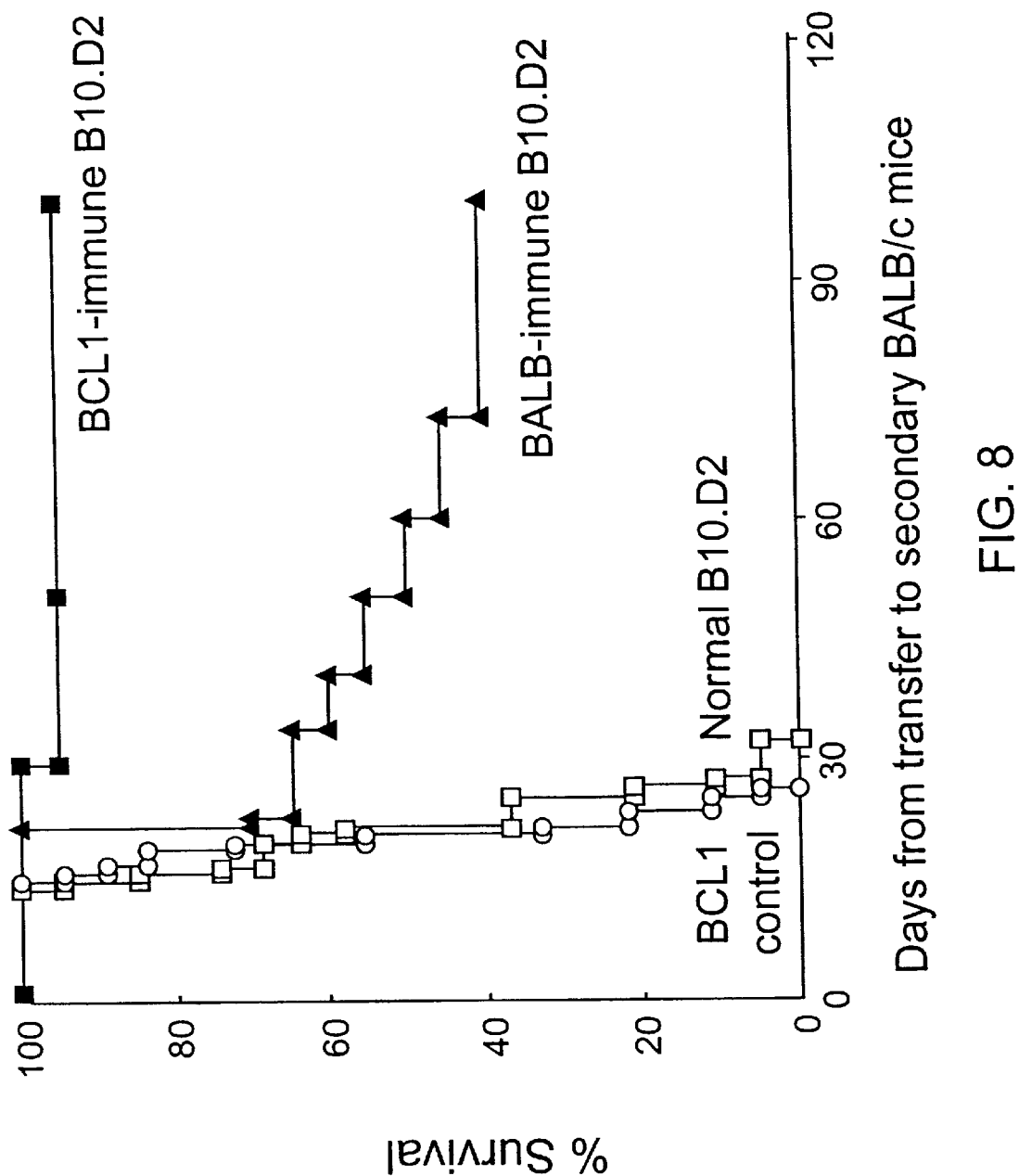
FIG. 8. Survival of secondary BALB/c host mice after transfer of spleen cells from primary BALB/c host mice injected with BCL1 tumor cells and lymphoid cells from either immunized or non-immunized B 10.D2 donor mice incompatible with the primary BALB/c host mice at MiHL only.

The efficiency of MiHL incompatible spleen cells in eradicating residual BCL1 cells was also assayed by adoptive transfer into secondary BALB/c recipients (10 mice in each group) of $10^5$ spleen cells from separate pools of spleen cells made from the animals in each experimental group (at 3 weeks post transplantation) (FIG. 8). Interestingly, 95% of secondary BALB/c recipients inoculated with spleen cells obtained from the 1st group remained leukemia-free for >120 days. In contrast, only 41% of secondary BALB/c recipients inoculated with spleen cells obtained from the 2nd group were alive and leukemia-free for >120 days. All secondary BALB/c recipients of cells obtained from groups 3 and 4 developed leukemia within 45 (median 38) days. The anti-leukemic effects induced with BCL1-immunized B10.D2 spleen cells over both normal, unimmunized B10.D2 spleen cells and BALB/c spleen cell-immunized B10.D2 spleen cells were significant (p<0.001 and p=0.027, respectively). Unlike GVL effects induced across an incompatibility involving the MHC and MiHL, BALB/c spleen cell-immunized B10.D2 spleen cells induced stronger GVL effects compared with normal, unimmunized B10.D2 spleen cells (p<0.0001).

Figure 9:
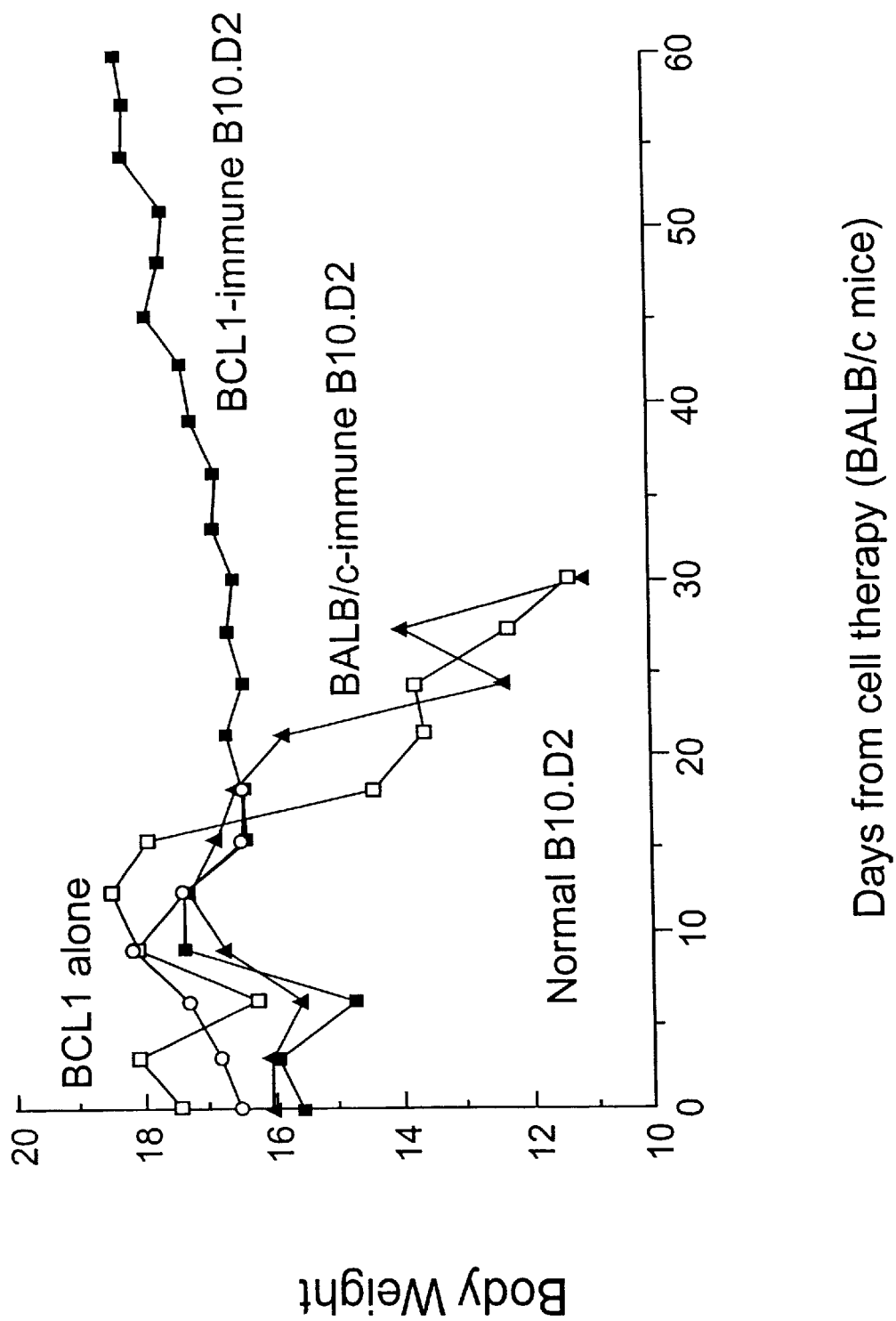
FIG. 9. Body weight changes in BALB/c host mice after injection of BCL1 tumor cells and lymphoid cells from either immunized or non-immunized B10.D2 donor mice incompatible with the host mice at MiHL only.

FIG. 9 shows that BALB/c mice inoculated with MiHL-incompatible, BCL1-immune B10.D2 spleen cells, after a minor bout of GVHD manifested by transient weight loss in the first week post grafting, were fully resistant to GVHD. In contrast, BALB/c mice inoculated with either spleen cells from MiHL-incompatible normal, unimmunized B10.D2 mice or spleen cells from MiHL-incompatible BALB/c spleen cell-immunized mice developed lethal GVHD. Nevertheless, recipients given BALB/c spleen cell-immunized B10.D2 spleen cells survived longer than control animals, indicating that some GVL effects may have been induced but were masked by GVHD.

EXAMPLE 12

Histological Findings in Mice with Induced GVHD/GVL

As indicated above, mice treated with immunized lymphocytes resisted leukemia development more effectively than recipients of non-immunized cells, and yet developed less GVHD across MHC and MiHL and MiHL only barriers. Of 3 mice that received therapy with normal, unimmunized spleen cells, 2 had major histological abnormalities in the liver compatible with acute GVHD. Similar liver lesions were demonstrated in only 1 of 5 mice treated with donor cells from mice immunized with host spleen cells. None of 4 mice treated with spleen cells from BCL1-immunized animals had any histological abnormalities in the liver. No leukemic infiltrates were demonstrable in any of the mice treated across an incompatibility involving both MHC and MiHL. In mice challenged across MiHL barriers only, injection of normal B10.D2 cells did not cause any histological changes consistent with GVHD in the BALB/c recipients, whereas mice injected with B10.D2 spleen cells obtained from BCL1-immunized or BALB/c spleen cells-immunized B10.D2 mice had infiltrations in the lung and in the liver. However, as indicated above, these infiltrations were not associated with increased GVHD. Leukemia cells were found in the lung and liver of BALB/c mice injected with normal, unimmunized donor spleen cells and in BALB/c recipients of spleen cells from BALB/c spleen cell-immunized B10.D2 mice. In contrast, no leukemic infiltrates were found in mice treated with spleen cells obtained from BCL-immunized mice.

EXAMPLE 13

Cytokine Production Correlates with GVHD and GVL Potential

Figure 10:
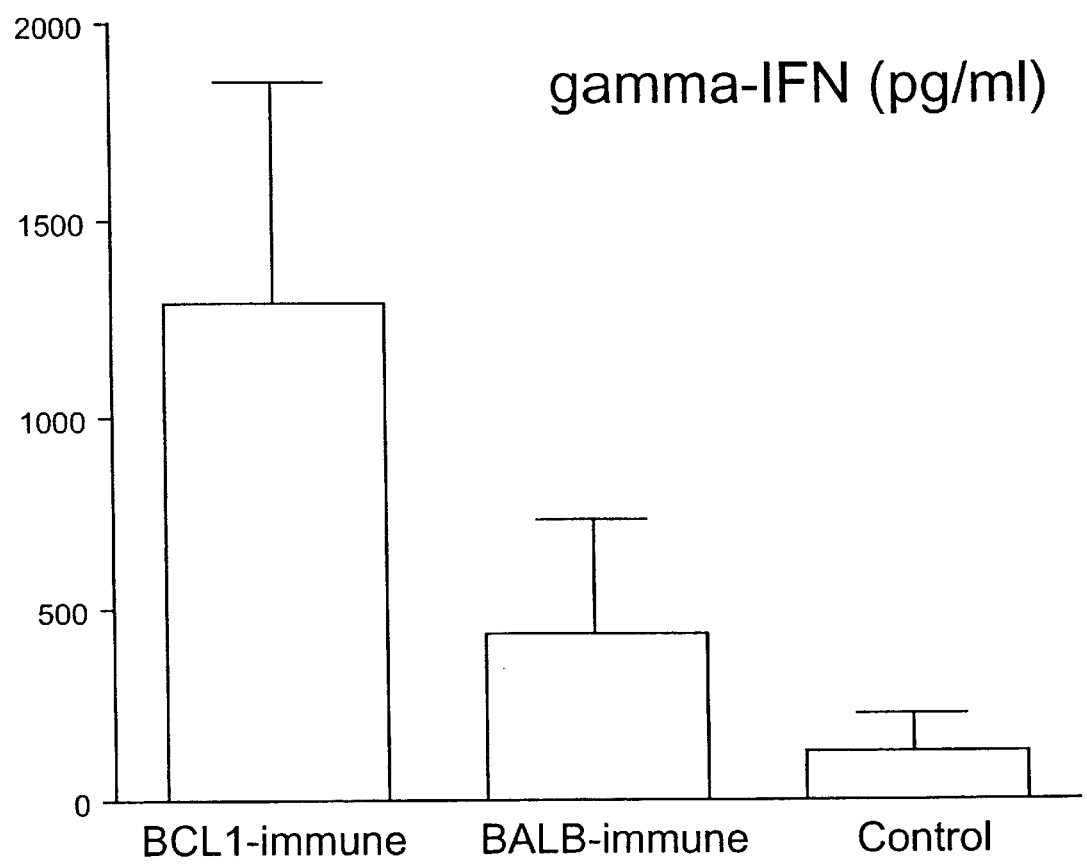
FIG. 10. Production of interferon-γ (IFN-γ) by spleen cells from C57BL/6 mice immunized with either BCL1 tumor cells or BALB/c spleen cells and by spleen cells from unimmunized C57BL/6 mice.
Figure 11:
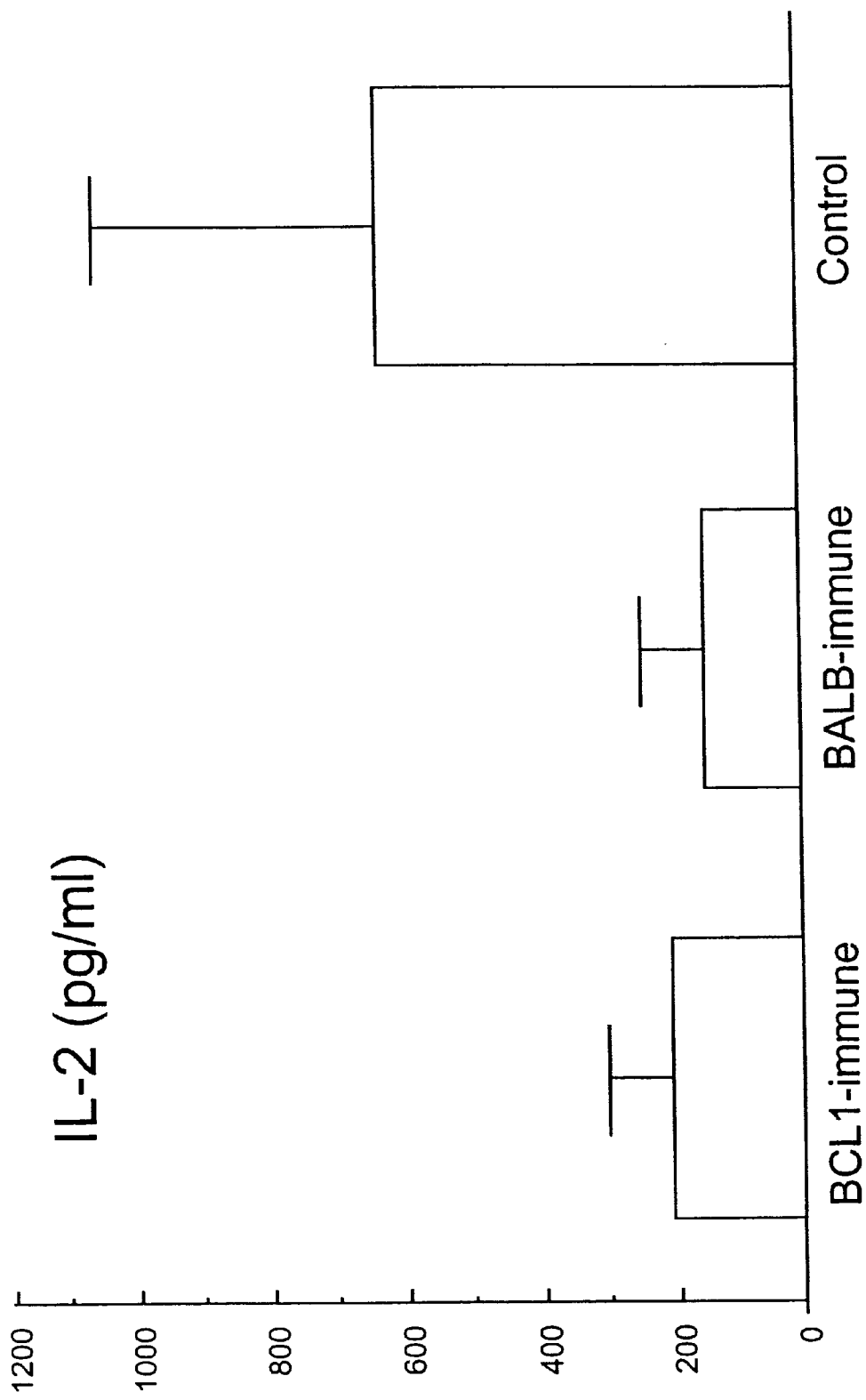
FIG. 11. Production of interleukin-2 (IL-2) by spleen cells from C57BL/6 mice immunized with either BCL1 tumor cells or BALB/c spleen cells and by spleen cells from unimmunized C57BL/6 mice.
Figure 12:
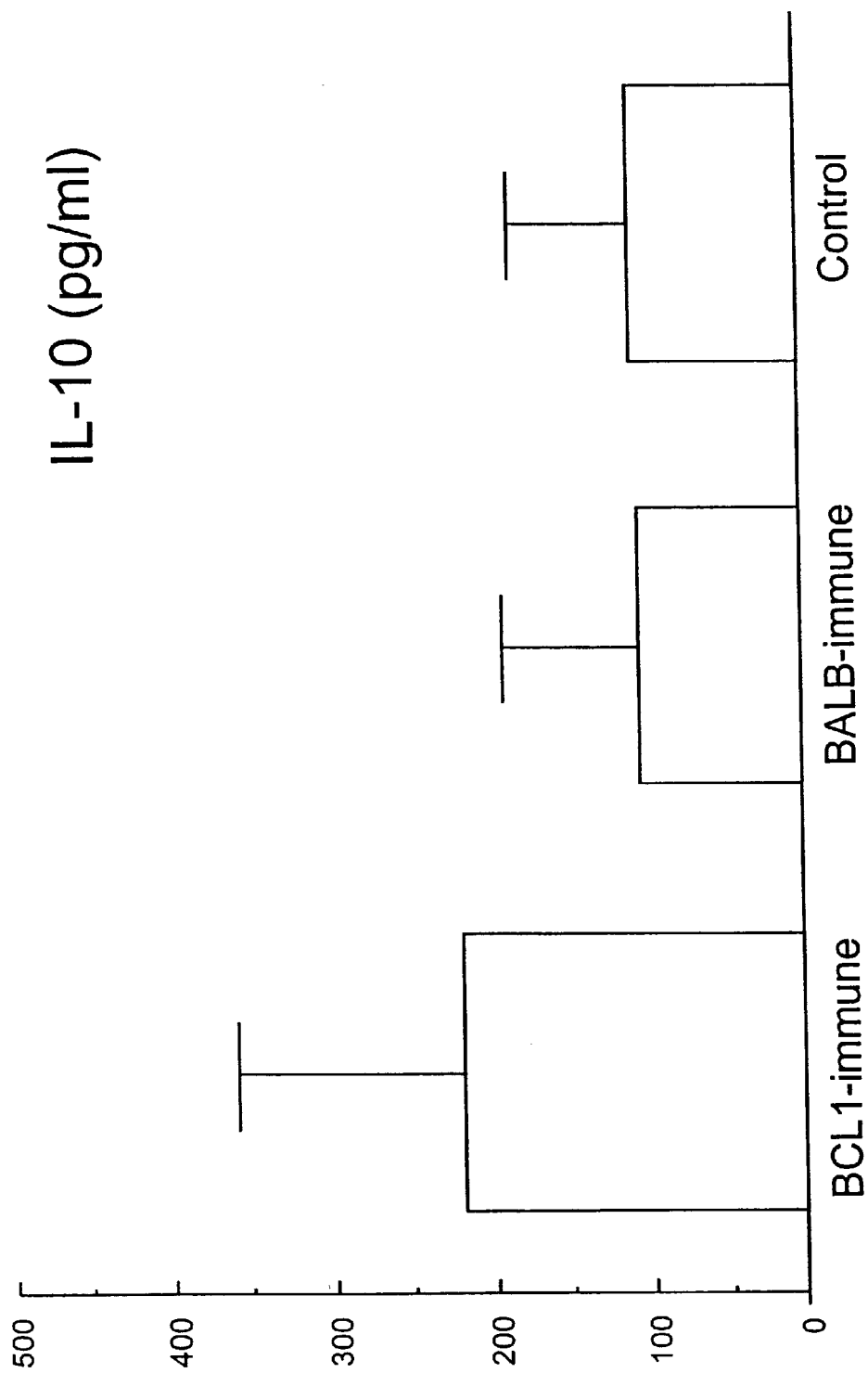
FIG. 12. Production of interleukin-10 (IL-10) by spleen cells from CL57BL/6 mice immunized with either BCL1 tumor cells or BALB/c spleen cells and by spleen cells from unimmunized C57BL/6 mice.

The cytokine profiles of (a) spleen cells from C57BL/6 mice immunized across an incompatibility involving both MHC and MiHL alloantigens by injection of either BCL1 cells or normal BALB/c spleen cells and (b) spleen cells from F1 mice inoculated with BCL1 cells and the spleen cell populations recited in (a), were determined.
Results As shown in FIG. 10, the level of IFN-γ in the supernatant of spleen cells of BCL1-immunized C57BL/6 mice was 3 times higher than that of spleen cells from BALB/c spleen cell-immunized mice and 6 times higher than that in normal, unimmunized spleen cells. The level of IL-2 in the supernatant of spleen cells of normal, unimmunized C57BL/6 mice was 4 to 5 times higher than the level of IL-2 in the supernatant of spleen cells obtained from donors immunized with either BCL1 or with BALB/c spleen cells (FIG. 11). The level of IL-10 in supernatant of spleen cells from C57BL/6 mice immunized with BCL1 cells was 2 times higher than that in the supernatant of spleen cells from C57BL/6 mice immunized with BALB/c spleen cells and of spleen cells from normal, unimmunized C57BL/6 cells (FIG. 12). No differences in the supernatant levels of TNF-α were detected in spleen cells from normal, unimmunized C57BL/6 mice, BCL1-immunized C57BL/6 mice, and BALB/c spleen cell-immunized C57BL/6 mice.

Figure 13:
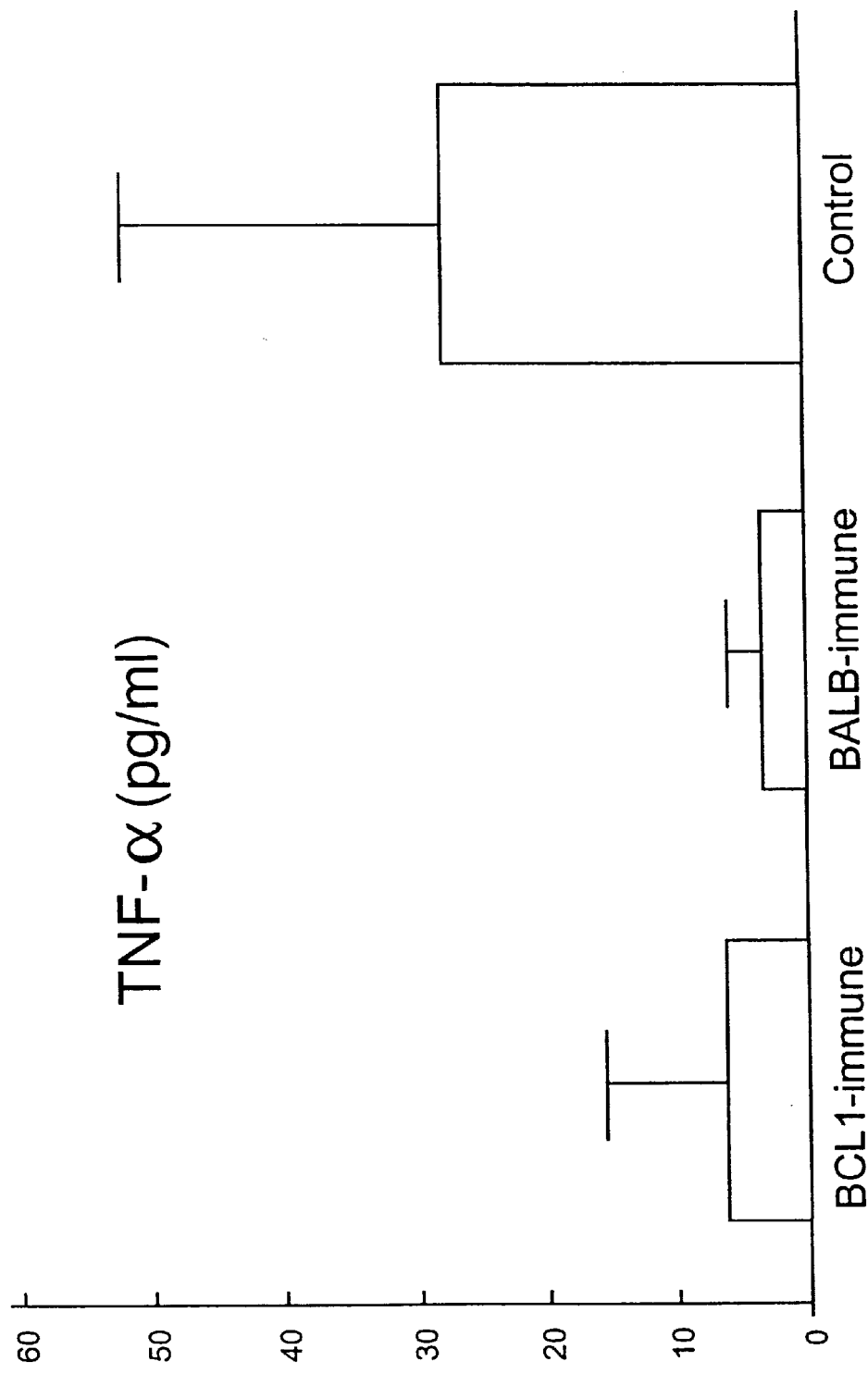
FIG. 13. Production of tumor necrosis factor-α (TNF-α) by spleen cells from F1 mice injected with the three spleen cell populations represented in FIGS. 10–12.
Figure 14:
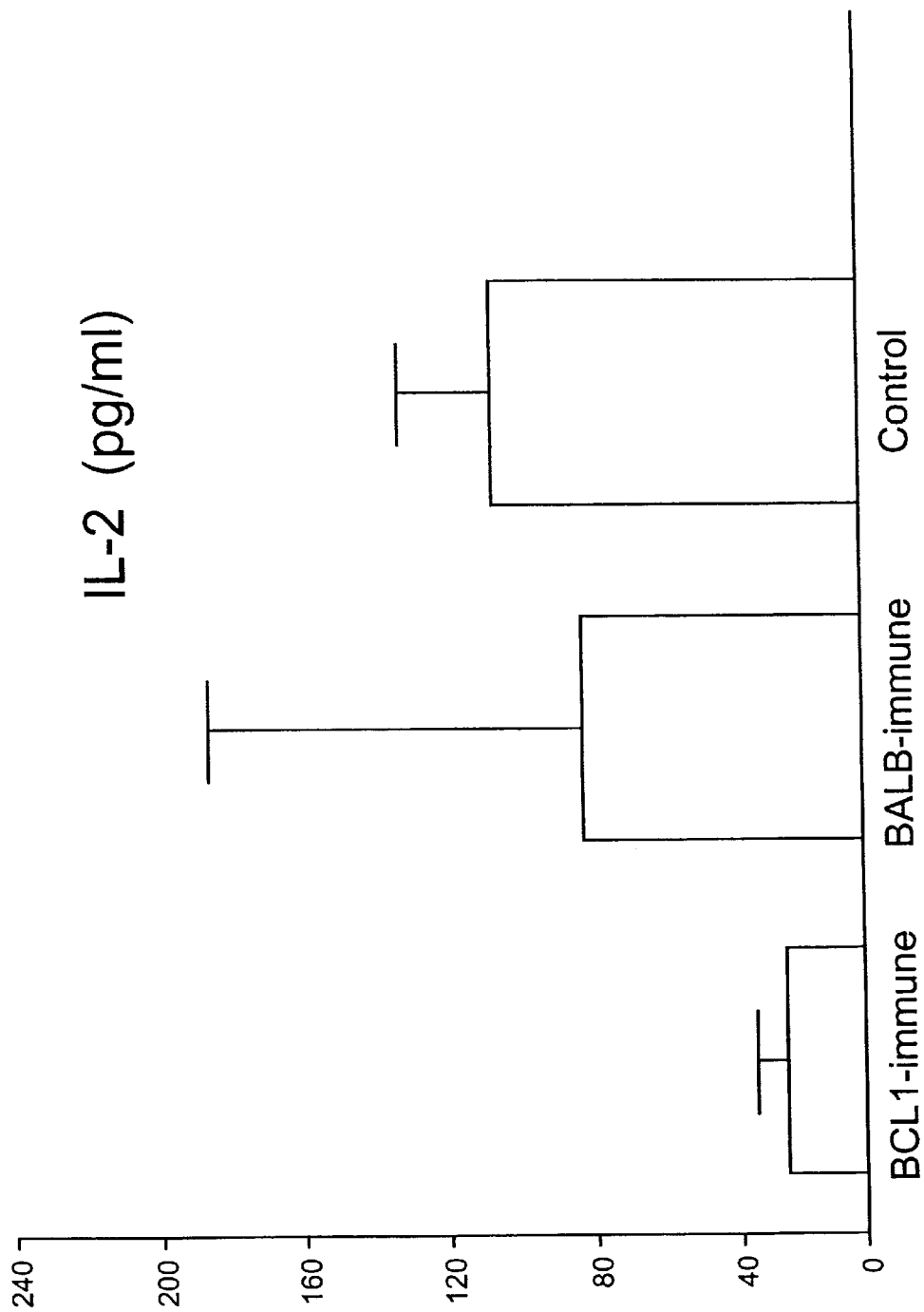
FIG. 14. Production of IL-2 by spleen cells from F1 mice injected with the three spleen cell populations represented in FIGS. 10–12.
Figure 15:
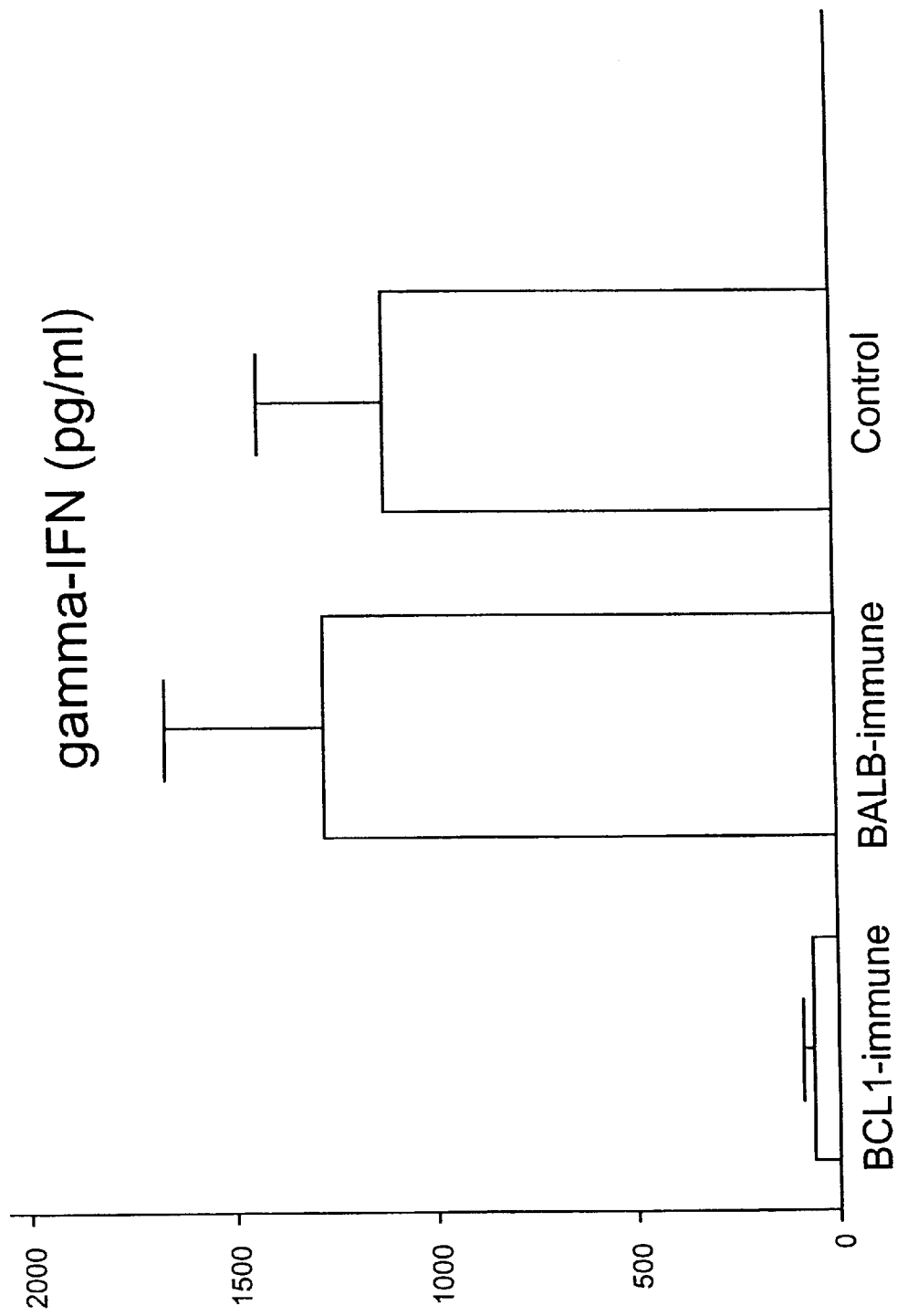
FIG. 15. Production of IFN-ã by spleen cells from F1 mice injected with the three spleen cell populations represented in FIGS. 10–12.
Figure 16:
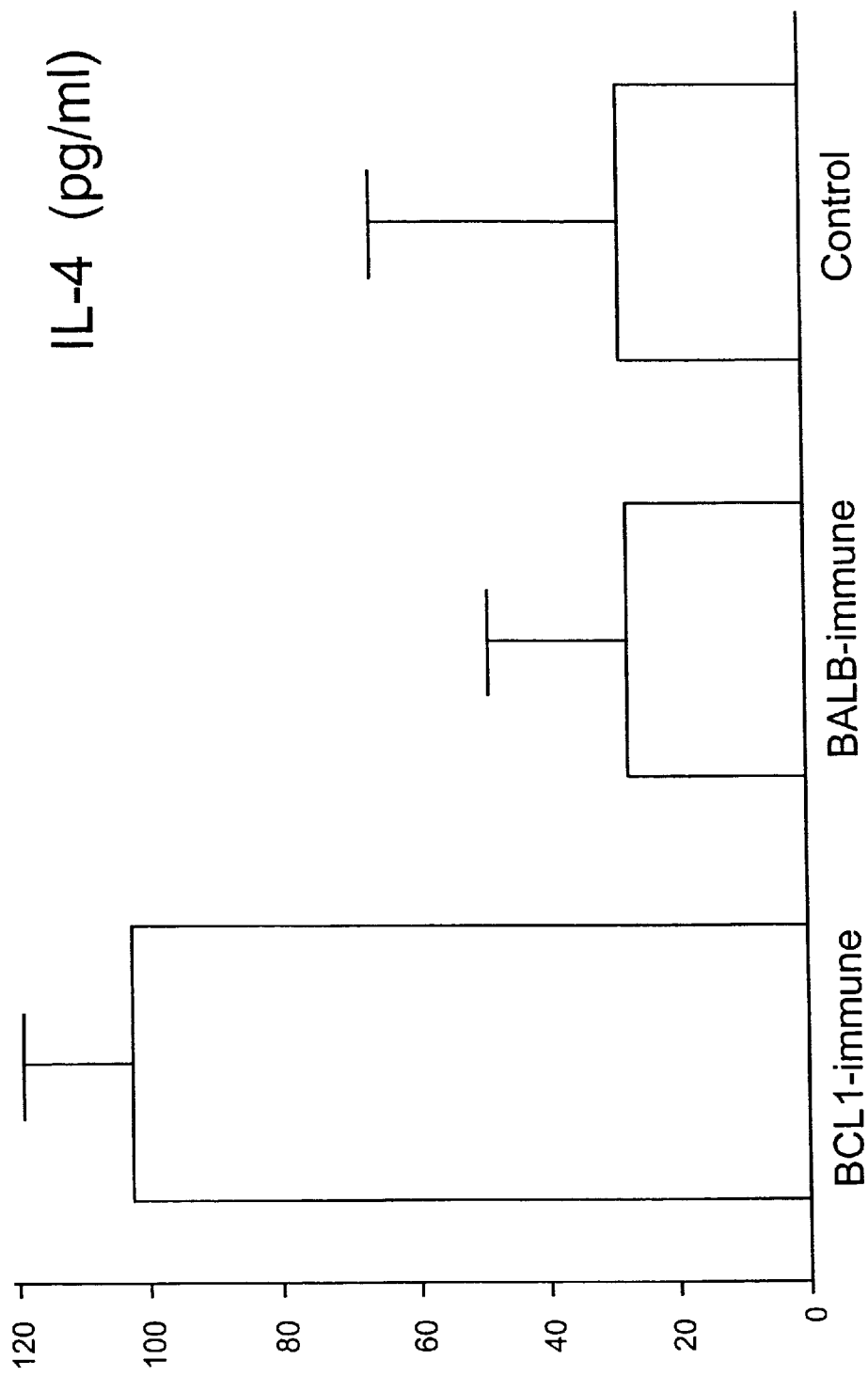
FIG. 16. Production of interleukin-4 (IL-4) by spleen cells from F1 mice injected with the three spleen cell populations represented in FIGS. 10–12.

Cytokine levels were also measured in supernatants of cultures of spleen cells isolated 3 weeks after cell therapy from F1 recipients of the above C57BL/6 spleen cells. TNF-α levels in supernatants of spleen cells from F1 mice treated with normal, unimmunized C57BL/6 spleen cells were 4–10 times higher than in supernatants of spleen cells from F1 mice given spleen cells from BCL1 immunized or BALB/c spleen cell-immunized mice C57BL/6 (FIG. 13). The level of IL-2 in the supernatants of spleen cells of FI mice inoculated with spleen cells from BALB/c spleen cell-immunized C57BL/6 mice or with spleen cells from normal, unimmunized C57BL/6 mice were 3 to 4 times higher than in the supernatant of spleen cells from F1 mice given spleen cells from BCL1-immunized C57BL/6 mice (FIG. 14). The level of IFN-γ in the supernatant of spleen cells from F1 mice given spleen cells from BCL1-immunized C57BL/6 mice was 10 times lower than that in the supernatant of spleen cells of F1 mice that received normal, unimmunized C57BL/6 cells (FIG. 15). No differences were detected in the supernatant levels of IL-10 in spleen cells from F1 mice inoculated with the three types of C57BL/6 cells. The level of IL-4 was about five times higher in the supernatant of spleen cells of F1 recipients of spleen cells from BCL1-immunized C57BL/6 mice than that in the supernatants of spleen cells from F1 mice inoculated with spleen cells from either ALB/c spleen cell-immunized C57BL/6 mice or normal, unimmunized C57BL/6 mice FIG. 16).

The potent allospecific (MHC and MiHL) tolerizing activity of BCL1 tumor cells, and hence the GVHD suppressive effect of immunization with them, could ee due to their presentation of the relevant alloantigens without the participation of co-timulatory molecules (e.g., B7), a mode of antigen presentation known to induce tolerance. In addition, the cytokine profiles observed in the experiments described above suggest a possible basis for the seemingly paradoxical findings of (a) enhanced anti-tumor efficacy and (b) concomitant decreased GVH activity in lymphoid cells from donor mice pre-exposed to host tumor cells compared to lymphoid cells from mice pre-exposed to host hemopoietic (spleen) cells. It is possible that the Th1/Th2 balance, both in the lymphoid cells of the immunized donor animals and in those of the host animals to which the immunized lymphoid cells are transferred, is differentially affected by the type of immunization given to the donor animal. Thus, for example, production of IL-10 (a prototypical Th2 cytokine) was up-regulated whereas production of IL-2 (a prototypical Th1 cytokine) was decreased in C57BL/6 spleen cells obtained from mice immunized across an MHC barrier with tumor cells compared to spleen cells from C57BL/6 mice immunized across the same MHC barrier, but with normal spleen cells (FIGS. 11 and 12). In addition, an increased level of IL-4 (another prototypical Th2 cytokine) (FIG. 16) accompanied by reduced IL-2 (FIG. 14), TNF-α (FIG. 13) and IFN-γ (FIG. 15) (all prototypical Th1 cytokines) levels in supernatants of spleen cells from F1 host mice injected with BCL1-immunized C57BL/6 spleen cells, relative to the levels in supernatants of spleen cells from F1 host mice injected with spleen cells from BALB/c spleen cell-immunized C57BL/6 donor mice, suggest that the Th2 shifted C57BL/6 donor cells transferred the Th2 bias (i.e., higher level of Th2 effects compared to Th1 effects) to the F1 hosts. Furthermore, it is known that Th1-type cytokines are generally associated with cellular immune and delayed-type hypersensitivity responses, while Th2 cytokines are generally associated with humoral (antibody) responses and that GVHD is largely due to cell-mediated immunological effects. Thus, in summary, immunization of the donor mice with tumor cells could result in a bias towards Th2 cytokine production and hence diminished GVHD disease potential in the T cells of the donor mice.

It is also possible that, while the Th1 cytokine levels are decreased sufficiently to minimize GVHD, there may be adequate levels for an effective cellular anti-tumor (GVL) response. Alternatively, the mechanism of the anti-tumor response could differ in some aspects from the GVHD response and, as such, could be facilitated by Th2 cytokines rather than by Th1 cytokines. In addition, not only are Th2 cytokines generally considered not to be "helper" cytokines for cellular immune responses, they have been shown to actively suppress cellular immune responses. Thus, the Th2 bias transferred to the F1 host mice by cells from BCL1 tumor-immunized donor mice may actually act to actively suppress GVHD.

The above-described discordancy in GVL and GVHD activity in donor cells from animals immunized with tumor cells versus normal spleen cells could also be due to one or a combination of the following effects:

(a) tumor antigen specific effector T cells being relatively resistant to tolerance induction compared to alloantigen (MHC or MiHL) specific T cells;

(b) the anti-tumor activity being at least partially mediated by non-T cells (e.g., NK cells) that are activated rather than tolerized by tumor immunization and/or Th2 cytokines;

(c) tumor cells being relatively more sensitive to allo-specific effector cells; and (d) tumor cells being relatively poor inducers of activation induced apoptosis in allospecific and/or tumor specific effector cells.

While any one or a combination of the above-mechanisms may explain the above-described dissociation between GVL and GVHD activity, the invention is not limited by any particular mechanism of action.

EXAMPLE 14

Steps 1–3 of the Tolerization Protocol Can Be Performed on The Same Day as Transplantation ("Short Protocol")

Figure 17:
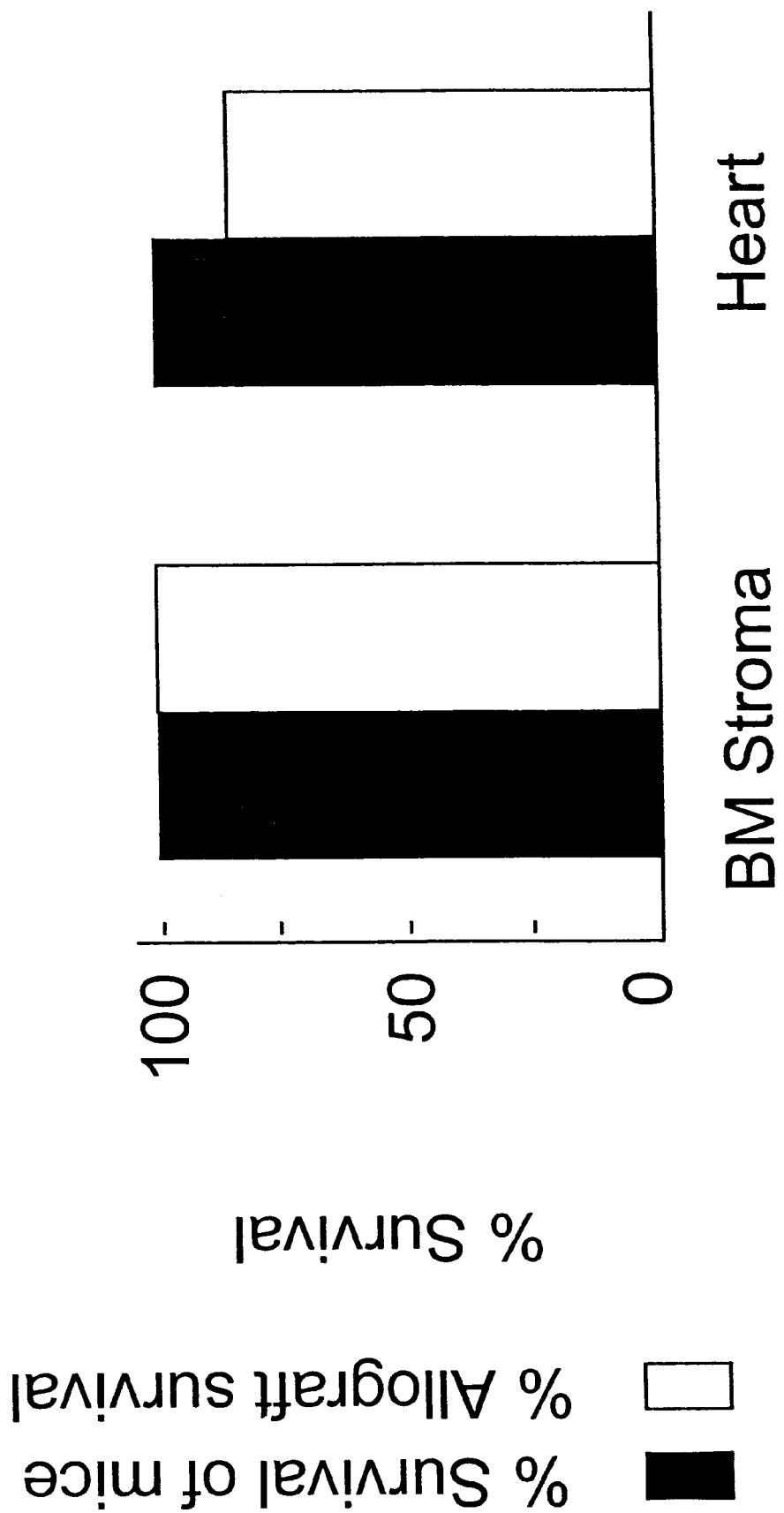
FIG. 17. Survival of BALB/c recipient mice and allografts (bone marrow stroma or hearts) from B6 mice after tolerization and transplantation using a protocol in which the sTLI, the first B6 bone marrow infusion, and allograft implantation were all performed on day 0.

BALB/c recipient mice were administered a single dose of sTLI (200 cGy) and an injection of non T cell depleted BMC from B6 donors on day 0. One group of BALB/c mice treated in this way received B6 BM stromal grafts and a second group received B6 heart grafts. All grafts were also performed on day 0. All mice received an injection of Cy (200 mg/kg) on day 1 and a second injection of B6 BMC on day 2. In light of the survival of 100% of the mice in both groups (FIG. 17), GVHD was prevented by the described protocols. In addition, 100% of the BM stromal grafts and approximately 80% of the heart grafts survived.

This experiment indicated that it is possible to successfully transplant an allograft into a subject at the same time as initiating the tolerogenic method of the invention. It is expected that by simply altering doses of, for example, the TLI, BM and/or Cy, as well as the frequency of subsequent administrations of these agents, it will also be possible to apply such a "short" protocol to xenogeneic recipient-donor combinations.

EXAMPLE 15

In Vitro Non-specific Depletion of GVHD Activity

The ability of the drug mafosphamide (ASTA-Z), which is identical to 4-hydroxyperoxycyclophosphamide (4HC), to deplete BALB/c mouse spleen cells of T cell responsiveness was tested under in vitro conditions known to result in preservation of hemopoeitic stem cell activity after treatment of hemopoietic cells from humans as well experimental animals (e.g., mice). BALB/c spleen cells were cultured for 30 minutes at 37° C. in tissue culture medium containing 100 μg/ml of ASTA-Z and then tested for in vitro T cell responses. The exposure to ASTA-Z resulted in the elimination of in vitro proliferative responses to the T cell mitogens concanavalin A (ConA) and phytohemagglutinin (PHA) (Table 8). Moreover, addition of IL-2 (1,000 IU/ml) to the cultures of spleen cells and ASTA-Z did not overcome inhibition of responsiveness to the mitogens by the ASTA-Z.

TABLE 8

Treatment of murine spleen cells with ASTA-Z results in elimination of responsiveness to T cell mitogens.

| | Cell Proliferation[a] | | |
|---|---|---|---|
| Treatment | No Mitogens | Con-A | PHA |
| Untreated | 702 | 107,277 | 63,604 |
| ASTA-Z | 219 | 2,980 | 5,118 |
| rIL-2 | 31,090 | 52,287 | 39,390 |
| ASTA-Z + rIL-2 | 624 | 4,767 | 9,453 |

[a]Cell proliferation was measured as counts per minute (cpm) of [$^3$H]-thymidine incorporated into the cells.

Figure 18:
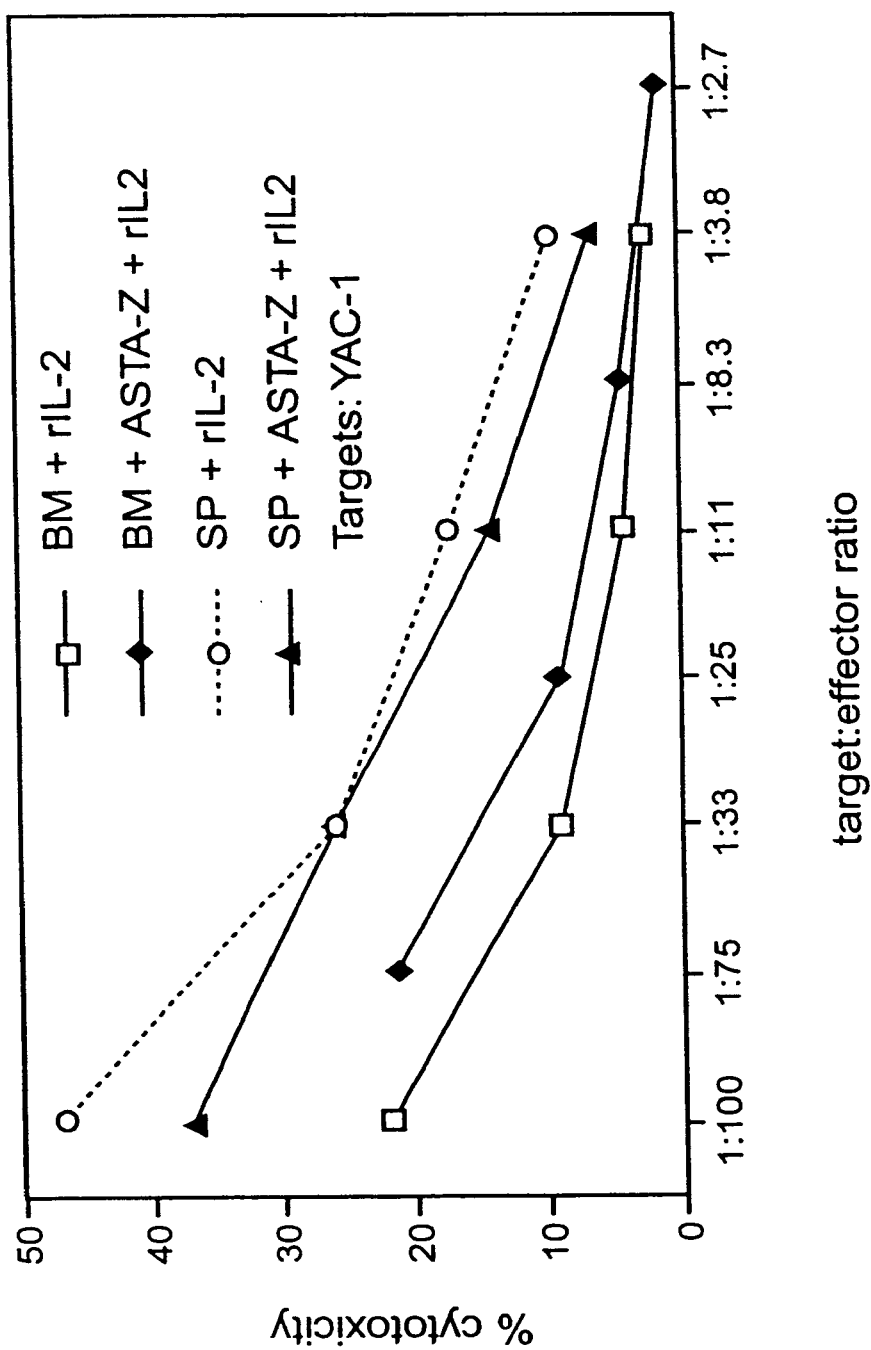
FIG. 18. Lysis of murine YAC-1 tumor targets by killer cells generated by in vitro activation with IL-2 of BALBIc bone marrow (BM) or spleen (SP) cells after either no treatment or treatment with ASTA-Z and subsequent culture with IL-2.
Figure 19:
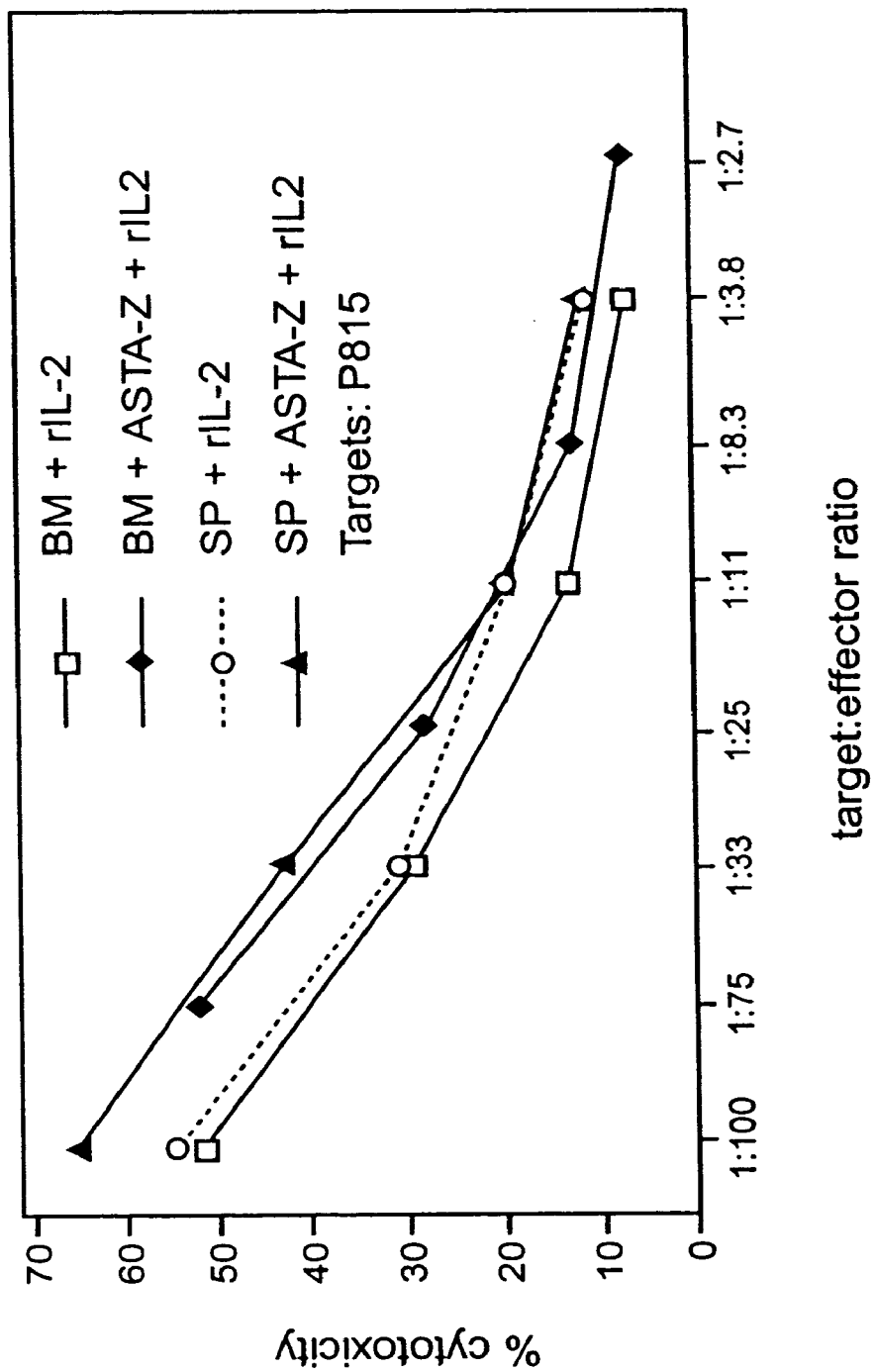
FIG. 19. Lysis of murine P815 tumor target cells by killer cells generated by in vitro activation with IL-2 of BALB/c bone marrow (BM) or spleen (SP) cells after either no treatment or treatment with ASTA-Z and subsequent culture with IL-2.

On the other hand, ASTA-Z treatment of BALB/c spleen cells (SP) or bone marrow (BM) cells did not decrease the generation of killer cells capable of killing murine YAC-1 and P815 tumor target cells by culturing of the SP and BM cells in IL-2 (FIGS. 18 and 19). After treatment of the SP or BM cells with ASTA-Z, as described above, excess ASTA-Z was removed and the cells were cultured with human rIL-2 (6,000 IU/ml) for 4 days. They were then harvested and tested for cytolytic activity in standard $^{51}$Cr-release assays. While YAC-1 cells are sensitive to lysis by both NK and activated NK cells, P815 cells are not sensitive to lysis by NK cells but are sensitive to activated NK cells. Thus it appears that the cytolytic activity detected in the assays was, largely at least, due to the action of activated NK cells. Furthermore, the same treatment of human PBMC with ASTA-Z did not decrease the generation of killer cells capable of killing human Daudi and K562 tumor target cells by culturing of the PBMC with human rIL-2 under the same conditions described above (Table 9). While K562 cells are sensitive to lysis by both NK and activated NK cells, Daudi cells are not sensitive to NK cells but are sensitive to activated NK cells. Thus, as in the murine system described above, the cytotoxic activity was probably due, largely at least, to NK cells activated by IL-2.

TABLE 9

Treatment of human PBMC with ASTA-Z does not decrease NK cell activity

| | Lysis of Target Cells[a] | | | |
|---|---|---|---|---|
| | Daudi target cells[b] | | K562 target cells[b] | |
| Experiment | Untreated PBMC | ASTA-Z treated PBMC | Untreated PBMC | ASTA-Z treated PBMC |
| 1 | 39 | 71 | 35 | 48 |
| 2 | 40 | 42 | 44 | 52 |

[a]Lysis of target cells was measured as the percentage of $^{51}$Cr released from $^{51}$Cr-labeled target cells after incubation with effector cells (at a target cell to effector cell ratio of 1:100) obtained from cultures containing IL-2 (6,000 IU/ml) and either untreated or ASTA-Z treated PBMC.

TABLE 9-continued

Treatment of human PBMC with ASTA-Z
does not decrease NK cell activity
Lysis of Target Cells[a]

| | Daudi target cells[b] | | K562 target cells[b] | |
|---|---|---|---|---|
| Experiment | Untreated PBMC | ASTA-Z treated PBMC | Untreated PBMC | ASTA-Z treated PBMC |

[b]K562 cells are sensitive to lysis by both activated and unactivated NK cells and Daudi cells are sensitive to lysis by activated but not unactivated NK cells.

Figure 20:
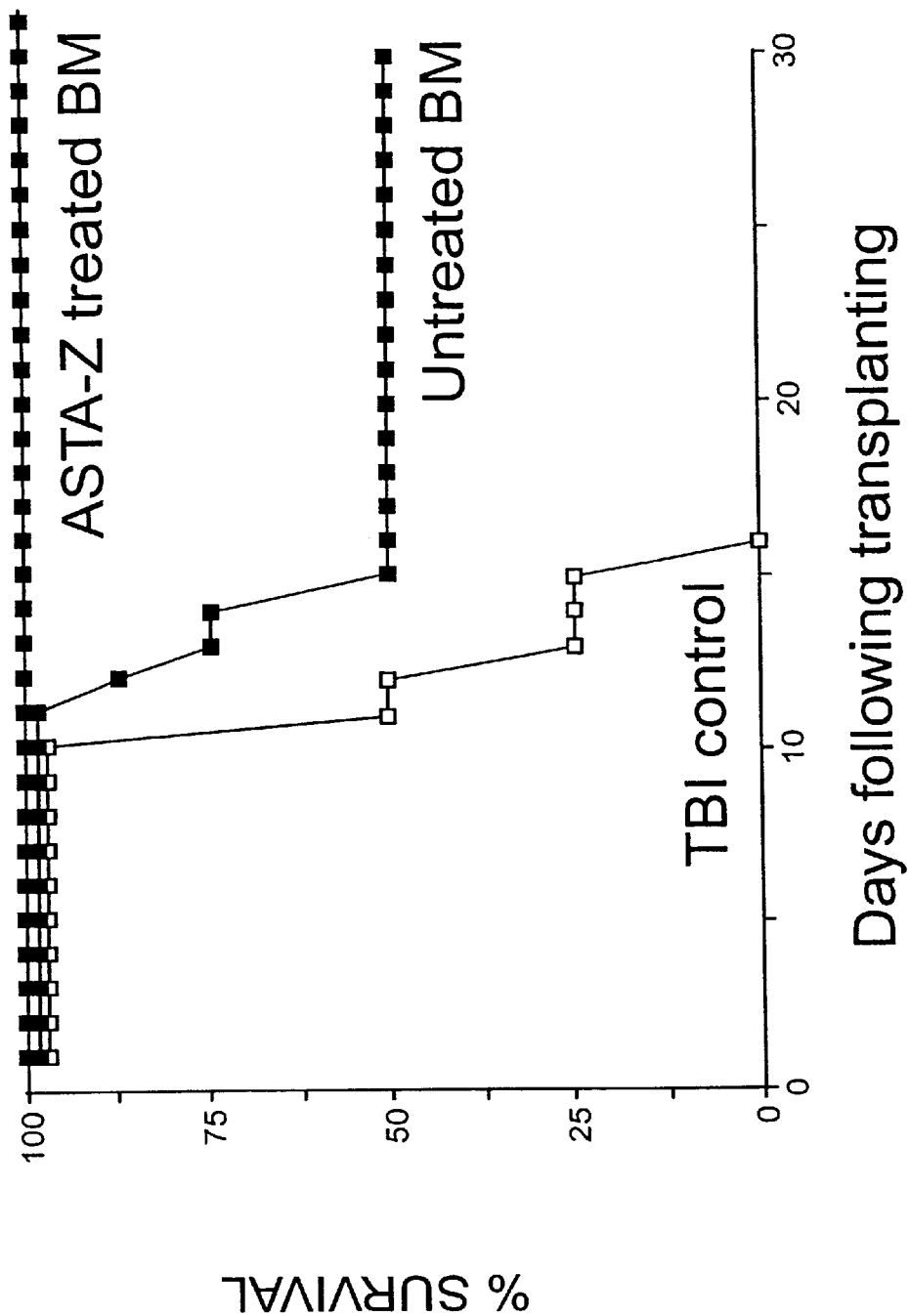
FIG. 20. Survival of lethally irradiated SJL/J mice after infusion of either untreated or ASTA-Z treated bone marrow cells from B6 mice. Survival data obtained with control lethally irradiated, unreconstituted SJL/J mice are also shown.

In parallel murine experiments, culture of B6 bone marrow for 30 minutes with ASTA-Z (100 μg/ml) prior to injection (25×10$^6$ per mouse) into lethally irradiated (1,100 cGy of TBI) SJL/J mice reduced the capacity of the bone marrow cells to induce GVHD (FIG. 20). Similarly, culture of B6 spleen cells for 30 minutes with ASTA-Z (100 μg/ml) prior to injection (25×10$^6$ per mouse) into sublethally irradiated BALB/c mice (600 cGy) reduced the capacity of the spleen cells to induce GVHD (FIG. 21).

Thus, ASTA-Z can be used to deplete hemopoietic cells to be used for either bone marrow transplantation (e.g., for step 4 of the tolerance protocol described herein). It can also be used to deplete cells to be used for cell therapy of the allospecific (or xenospecific) T cell reactivity that leads to GVHD while retaining or even being enriched for graft-versus-tumor (e.g., leukemia) activity which could, at least in part, be due to the action of NK cells.

EXAMPLE 16

Non-Myeloablative, Donor-Specific Tolerogenic Treatment in a Human Patient

Patient No. 1

Prior to non-myeloablative conditioning, donor-specific tolerance induction, and allogeneic bone marrow transplantation (ABMT), this male patient underwent autologous stem cell transplantation (ASCT) almost 38 months after diagnosis of Hodgkin's Disease stage III B. The patient had failed MOPP/ABVD alternative treatment (8 cycles), radiation therapy, subsequent treatments with velban, adriamycin, bleomycin and DTIC, and repeated cycles of additional chemotherapy including, following his first overt relapse 2 years after diagnosis, MOPP (4 cycles) and VP16, cisplatin, ifosfamide, and uromitexan (5 cycles). Relapse was noted again 2 months after ASCT and the clinical picture of fever without obvious infectious etiology suggested persistence of the Hodgkin's Disease.

Allogeneic bone marrow transplantation (ABMT), following non-myeloablative conditioning and donor-specific tolerization was offered to the patient as a possible method of treatment. It was considered that this treatment could overcome long-lasting hypoplasia and could antagonize the persisting Hodgkin's Disease by inducing graft vs. Hodgkin's Disease tumor cell responses, Tissue typing data revealed a phenotypic mismatch in HLA class I (serological testing) between the patient and the available donor, his father:

| Patient: | A28 | A19 | B41 | B5 |
|---|---|---|---|---|
| Donor (father): | A28 | A30 | B41 | B51 |

Typing of HLA class II revealed:
Patient: DRB1*1104 DRB1*0404 DQB1*0301 DQB*0402
Donor (father) DRB1*1101 DRB1*0404 DQB1*0301 DQB*0402

Starting on day 0, the patient was conditioned non-myeloablatively wiht Fludarabine (30 mg/kg/day) for 3 consecutive days. One day later, the patient received an infusion of G-CSF mobilized peripheral blood cells ("first allograft") collected form his father (2.98×10$^8$ nucleated cells/kg) as a source of donor-specific antigens, followed by 3 daily non-myeloablative period doses of cytoxan 60 mg/kg (4,500 mg daily) to eliminate donor-specific alloreactive T cells. An infusion of unselected paternal bone marrow cells (9.6×10$^8$ nucleated cells/kg) was carried out ("second allograft") one day after termination of the last dose of cytoxan. It was decided to use unmodified bone marrow cells with no further T cell depletion for the second allograft in order to maximize the chance of stem cell engraftment on the one hand as well as GVT effects on the other.

Fever up to almost 40° C. developed in the first week after the second allograft and the patient required frequent single donor platelet infusions for prevention of bleeding. The patient also received antibiotic therapy with amikacin, tazocin, preventive therapy against fungal infection with diflucan and acyclovir therapy against cytomegalovirus infection. Since fever did not respond completely to antibiotic therapy, amphotericin B (1 mg/kg) was given every other day. Fever persisted throughout hospitalization. The patient's white blood cell count (WBC) rose to $1.0 \times 10^9$/L on day +14 and his absolute neutrophil count (ANC) reached $\geq 0.5 \times 10^9$/L on day +14 and $\geq 1.0 \times 10^9$/L on day +28. The WBC rose gradually to a maximal level of $5.1 \times 10^9$/L with 75% granulocytes. However, thrombocytopenia persisted. Engraftment was confirmed by rising counts and by detection of donor DNA by the Variable Number of Tandem Repeats—Polymerase Chain Reaction (VNTR-PCR), a technique known to those in the art.

On day +10, the patient experienced a grand mal seizure which responded to valium infusion. No focal neurologic findings were found except that the Babinski's sign was positive bilaterally. Cyclosporine A was administered as a prophylactic treatment for GVHD. Overt skin rash typical of GVHD appeared on day +12. Liver manifestations developed subsequently. Despite combination therapy with solumedrol (2 mg/kg) daily and cyclosporine, with continuation of the antibiotic and anti-fungal therapy, the patient's condition deteriorated gradually, with diarrhea up to 12 times a day, starting on day +16, a symptom indicative of stage IV GVHD. Despite intensive treatment of both GVHD and potential infections, spikes of fever continued with dyspnea that developed in parallel with pulmonary bleeding and bilateral interstitial infiltration in the lungs on day +28. The patient was intubated on day +29. Large volumes of secretion were aspirated through the tube. The secretions included blood but lavage did not reveal any infectious agent. Despite intensive therapy including dopamine drip and careful maintenance of pulmonary system, the blood pressure dropped gradually and the patient expired on day +29.

In conclusion, the successful engraftment of the patient by his father's bone marrow used for the second allograft indicated that HLA mismatched stem cells can be accepted following selective depletion of host cells with the capacity to reject donor alloantigenic tissue and without myeloablative conditioning. Developments in the patient suggest that, due to pancytopenia following ASCT and the failure to establish a high level of protective mixed chimerism, he may have been more susceptible to GVHD. Non T cell depleted bone marrow was used for the second allograft and this unfortunately resulted in GVHD. Nevertheless, the above-described findings demonstrated that HLA mismatched cells can be accepted and engrafted without myeloablative conditioning using the described tolerogenic protocol.

These data considered in light of murine experiments indicate that it will be possible to obtain engraftment in human patients without GVHD if the donor bone marrow used for the second is allograft is either (a) depleted of T-cells prior to infusion or (b) is used undepleted but a transient stage of mixed chimerism in the recipient is achieved. Furthermore, the combined findings of this clinical study and the murine experiments indicate that, in human patients, it will be possible to prevent rejection of allografts if the recipient is depleted of donor-specific T cells prior to the allograft.

EXAMPLE 17

Effective Treatment of Human Chronic Myelogenous Leukemia (CML) with Allogeneic Lymphocytes Pre-Exposed to Alloantigens of the Patient Allogeneic cell therapy using donor lymphocytes pre-exposed to alloantigens of the patient was given to a female patient with Philadelphia chromosome-positive (Ph+) CML who had relapsed 9 months after allogeneic bone marrow transplantation. The bone marrow cells used for the transplant were from a HLA—A, —B, —C and —DR identical 6-month old brother (the "donor"). The patient had failed to respond to several rounds of allogeneic cell therapy (given subsequent to the bone marrow transplant) using donor PBMC that, in some of the treatments, were activated with IL-2. The patient's bone marrow contained approximately 95% Ph+cells prior to this allogeneic cell therapy which consisted of the following sequential procedures.

(a) $10^7$ donor PBMC per kg were administered i.v. 24 hours after a low dose of Cy (500 mg/M$^2$). No remission was obtained.

(b) $10^7$ donor PBMC (activated in vitro with IL-2) per kg were administered i.v. Beginning on the day of cell infusion, rIL-2 ($6\times10^6$ IU/m$^2$/day) was administered subcutaneously for 3 days. The whole procedure was performed twice, approximately one month apart, and resulted in a transient decrease to about 67% in the proportion of Ph+cells in the patient's bone marrow.

(c) $6\times10^6$ paternal PBMC (activated in vitro with IL-2) were administered i.v., resulting in a transient decrease to about 60% in the proportion of Ph+cells in the patient's bone marrow. This decrease was followed by a gradual increase to 94% Ph+bone marrow cells.

At this time it was decided to treat the patient with donor PBMC activated in vitro against alloantigens of the patient. The patient was infused with donor PBMC that had been exposed twice in vitro for 1 day to irradiated (3,000 cGy) PBMC from both parents of the patient (and donor). The donor PBMC were thus activated to parental MHC antigens not expressed by the patient and MiHL antigens expressed by the patient but not the donor, the patient and donor being HLA identical children of the parents. The patient was then given rIL-2 ($6\times10^6$ IU/m$^2$/day) for 3 days, starting on the day of cell infusion. The whole procedure was carried out twice, approximately one month apart. Interferon-α ($1.5\times 10^6$) was administered 3 times a week for 4 years. The patient has now been in remission for greater than five years. She has no detectable leukemia cells (both by karyotype analysis and RT-PCR to detect mRNA transcripts derived from a bcr/abl hybrid DNA sequence produced by the Philadelphia t(9;22)(q34;q11) chromosomal translocation), 100% of both her blood and her bone marrow cells are donor-derived, and she has no clinical signs of GVHD.

This study indicates that the efficacy of allogeneic cell therapy of human cancer can be enhanced by pre-exposure of the donor cells to be used for therapy to alloantigens expressed by the patient. In light of the above-described experiments in mice, such pre-exposed donor cells are also likely to display decreased GVH activity compared to unexposed cells.

EXAMPLE 18

Adoptive Allogeneic Cell Therapy With Mismatched Naïve Lymphocytes Activated With rIL-2 Or Immune Lymphocytes Reactive Against Normal Host-Specific Alloantigens Or Host-Derived Tumor Cells In the absence of a fully matched donor available, we have decided to use haploidentically mismatched related lymphocytes for induction of transient anti-tumor effects. Donor-derived anti-cancer effector lymphocytes consisted of rIL-2 activated cells (four days activation with rIL-26,000 IU/ml) or using donor lymphocytes activated in vitro against irradiated tumor cells or host alloantigens in one way mixed lymphocyte tumor reaction or using donor lymphocytes pre-cultured with irradiated parental or other family member expressing either one of the patient's haplotypes in one way mixed lymphocyte cultures (in order to induce effector cells against inherited paternal or maternal haplotypes, to maximize anti-host alloreactivity to be used as adoptive allogeneic cell therapy (alloCT). In order to maximize anti-cancer effects, patients can be immunosuppressed with Fludarabine 25 mg/m$^2$×5 days. In order to maximize tumor cell kill, cell surface antigens of tumor cells can be up-regulated with two injections of alpha interferon $3\times10^6$ two days prior to cell infusion. Following cell infusion, patients receive subcutaneously rIL-2 $6\times10^6$ IU/m$^2$ in an attempt to continue to activate in vivo donor anti-tumor reactive lymphocytes. Two weeks post cell therapy, patient may receive injections of alpha interferon $3\times10^6$ IU every other day subcutaneously as anti-proliferative and mostly as anti-angiogenic effects to minimize or jeopardize tumor cell growth from residual tumor cells escaping alloCT.

Patients treated thus far with our protocols include the following case reports:

1. ADOPTIVE ALLOGENEIC CELL THERAPY WITH MISMATCHED LYMPHOCYTES USING rIL-2 ACTIVATED KILLER LYMPHOCYTES

Patient Number 1: JE 43 year old female

Diagnosis: metastatic breast cancer

This patient was diagnosed as grade III metastatic breast cancer her2/NEU negative. Patient underwent partial mastectomy and axillary lymph nodes were not involved. The patient was treated with 6 courses of CMF (cytoxan, methotrexate and 5-FU) and subsequently with involved field irradiation 50 Gy. Three years later, recurrent disease was diagnosed with infiltration of breast cancer cells in the bones (sternum and supraclavicular) and biopsy proven involvement of three supraclavicular lymph nodes. The patient was treated with Adriamycin and taxol and was subsequently admitted approximately a year-and-a-half for high dose myeloablative chemotherapy supported by autologous stem cell transplantation. Involved field radiation was administered one month after admission. Subsequently, the patient was placed on Tamoxifen 20 mg daily. Her treating physician considered her a very high-risk case and therefore she came to Hadassah to consider additional immunotherapy in an attempt to control her disease.

The patient was treated with an alloCT protocol, including Fludarabine 25 mg/m$^2$×5 days to delay rejection of rIL-2 activated donor lymphocytes. In order to maximize tumor cell kill we have attempted to up-regulate cell surface expression of alloantigens and possibly tumor antigens with two injections of alpha interferon 3×1$^{60}$ given two days prior to cell infusion. Following cell infusion, patients received subcutaneously rIL-2 6×10$^6$ IU/m$^2$ in an attempt to continue to activate in vivo donor anti-tumor alloreactive lymphocytes. Peripheral blood mononuclear cells were isolated using Baxter CS3000 from her haploidentically mismatched son. Cells were cultured in vitro in RPMI 1640 medium supplemented with 6,000 IU/ml for 4 days in 7% heat-inactivated AB human serum for 4 days at 37° C. in 5% $CO_2$ in air incubator. A total of 3×10$^7$ lymphokine activated killer (LAK) cells/kg were infused with no side effects. Following cell infusion, the patient was treated with rIL-2. Following cell infusion, three days after discontinuation of rIL-2, diffuse maculopapular urticaria-like skin rash developed all over her skin with no jaundice and no diarrhea. The rash appeared typical for subcutaneous rIL-2 reaction rather than typical GVHD. However, liver function tests, were somewhat disturbed with AST 70 IU; ALT 227 IU; LDH 884 IU and G-GTP 350IU. The rash disappeared without any further treatment within the next few days spontaneously. To date, the patient is fully active, with a Karnofsky score of 100% with no evidence of disease.

Patient Number 2: EG 36 year old male
Diagnosis: Carcinoma esophagus with regional and hepatic metastases.

Diagnosis of gastroesophageal cancer was made by endoscopy. Subsequently, he received chemotherapy with a combination of 5 FU, CisPlatin and Taxol. One year later he received 35 fractions of local radiation therapy followed by additional chemotherapy. In Three months later, a laparotomy revealed the presence of tumor around and near the aorta with additional and lymph node infiltration which were considered irresectable. Taxol was given once in three weeks for three months. Five months later two new lymph nodes were discovered near the base of the esophagus and the patient was treated again with Taxol for four months. The nodes did not disappear and subsequently, he developed anemia and required blood transfusions. Although, his physicians considered him to have accomplished a partial response, a review of CT scans done a year after the laparotomy revealed an epigastric mass 3.5×2.8 cm. In addition, two small peripheral hypodense lesions were noticed in the right lobe of the liver, approximately 0.5 cm in diameter each.

One month later, the patient entered an alloCT protocol rIL-2 activated (LAK) cells from his haploidentically-mismatched (haploidentically mismatched means there is mismatch at HLA-A, B, C and DR on one chromosome and matched with the other) brother were given twice, 17×10$^7$ and 2.2×10$^7$ nucleated cells/kg, respectively. rIL-2 treatment resulted in nausea, malaise, and fever and weight loss, which improved after discontinuation of treatment. No signs of GVHD were observed. The patient died from disease approximately nine months after the alloCT protocol began.
Patient Number 3: JS 24 year old male Diagnosis: Malignant melanoma This patient noticed changing color and size of a cutaneous nervous over the left scapular area. Wide surgical excision revealed malignant melanoma, stage III B. The tumor was 15 mm with a vertical growth of 2.5 mm Breslow's thickness, Clark level 4 with lymphocytic infiltration. Eight months later, an enlarged lymph node was noted in the left inguinal area. Left inguinal lymph nodes were excised, and one, 15 mm in diameter was proven positive, with capsular invasion of melanoma infiltrate. A DTIC adjuvant treatment was given as for stage III B, with three courses of DTIC C 850 mg/m$^2$ every three weeks. Subsequently, alpha-interferon 3×10$^6$ IU was given daily subcutaneously for three weeks.

Considering the high-risk disease, the patient was referred to Hadassah with the goal in mind to consider additional immunotherapy. In the absence of siblings, stem cell transplantation to induce host vs graft tolerance could not be considered and therefore the patient was offered allogeneic cell therapy three months later, the patient was treated on an outpatient basis, with no complications. A total of 2×10$^7$ LAK cells/kg were infused on day A from his haploidentically mismatched mother.

In response to treatment with rIL-2 the patient developed malaise, fever, vomiting and diarrhea which subsided following discontinuation of treatment. The patient is back home in Bulgaria with no evidence of disease, completely asymptomatic, with a Karnofsky score of 100%. The patient is alive and well with no evidence of disease.

2. ADOPTIVE ALLOGENEIC CELL THERAPY WITH MISMATCHED LYMPHOCYTES ACTIVATED AGAINST HOST-SPECIFIC ALLOANTIGENS

Patient Number 1: NL 9 years old girl
Diagnosis: CML adult type, early hematologic relapse following allogeneic bone marrow transplantation NL was diagnosed as having Philadelphia positive CML in chronic phase at the age of 7 years. She presented with fever, pain in her left leg and a spleen palpable 5-cm below the left costal margin. Her leukocyte count revealed leucocytosis in the range of 250×10$^9$/L, mostly mature granulocytes, with a few myelocytes and occasional blasts. Thrombocyte counts reached 1,600×10$^9$/L, and the level of LDH 1,150 U. Bone marrow morphology was typical of CML and cytogenetic analysis of spontaneous metaphases revealed typical Philadelphia chromosome translocation, with 46xx t(9;22)(q34;q11) in all cells analyzed. CSF examination was negative for malignancy. Initial cytoreduction was achieved with busulfan 2 mg/day and twice, at monthly interval, cytosar 80 mg twice daily. Because of insufficient response she was switched after 2 months to hydroxyurea 1 g/day, with return of blood counts to normal levels.

Allogeneic BMT from an HLA-A, B, C and DR identical 6 month older brother was performed at the Fred Hutchinson Center in Seattle, after conditioning with busulfan 4 mg/kg×4 days, cytoxan 60 mg/kg×2 days and one intrathecal injection of methotrexate. She received a total of 3.7×10$^9$ nucleated bone marrow cells (1.9×10$^8$ cells/kg). Anti-GVHD prophylaxis consisted of a combination of methotrexate and cyclosporin A (CSA) for nearly 6 months. She had signs of engraftment on day +11 and an ANC >0.5×10$^9$/L by day +18. The post-transplant course was uneventful except for mild signs of VOD, a persistent bacteremia (Acinetobacter anitratus) and increased creatinine levels with mild hypertension, which were attributed to treatment with CSA. There was no evidence of clinical acute or chronic GVHD at any stage.

The patient continued to do clinically well, but 9 months after the transplant, an increase in the leukocyte and platelet counts was noticed. Bone marrow aspiration revealed typical Philadelphia chromosome translocation in 19/20 46XX cells (95%) with only one (5%) normal 46XY cell. The Ph-positive translocation was also recognized by RT-PCR. The patient was treated with small doses of hydroxyurea with a good hematologic response, followed by an attempt of immunotherapy with donor cells. At the time of initiation of DLI patient was immunologically reconstituted, with CD3 43% (normal 68±2); CD4 23% (normal 46±2%); CD8 15% (normal 24±1%); DR 30% (normal 19±3%); CD16 22% (normal 9±2); CD19 26% (normal 9±2). The proliferative response to phytohemagglutinin was normal (stimulation index of 192 as compared with 185±12) with elevated spontaneous cytotoxic activity against chromium labeled K562 target cells (37 lytic units as compared with 5±1 in normal controls). The patient developed avascular necrosis of the left hip but other than that no further complications were observed.

Collection of donor lymphocytes was inadequate and problematic, because of the small size of the minor donor, and we could not give more than approximately $10^7$ cells/kg isolated from 50–100 ml of whole blood. In an attempt to increase the efficacy of adoptive allogeneic cell therapy we gave small doses of cytoxan (500 mg/m$^2$ with forced hydration) 24 hours prior to administration of the first DLI dose. No signs or symptoms of GVHD developed. Due to lack of response to DLI and lack of GVHD, patient was infused for the $2^{nd}$ time with $10^7$ donor lymphocytes/kg activated in vitro with rIL-2 (allogeneic "LAK cells") with subcutaneous rIL-2 ($6 \times 10^6$ IU/m$^2$/day) for 3 days, starting with the cell infusion on two months later, and again for the third time one month later, as previously described in details, in an attempt to activate the LAK cells in vivo continuously. Consequently, the proportion of Ph-positive cells in the marrow dropped transiently to 67%, and to 60% after a $4^{th}$ infusion of $6 \times 10^6$ father "LAK cells"/kg, however, the proportion of Ph-positive cells rose gradually to 94%. All these attempts to induce GVL and/or GVHD were ineffective and did not result in a significant durable decrease in the percentage of Ph-positive cells. In an attempt to escalate anti-host reactivity, patient received donor cells activated in vitro with a mixture of maternal and paternal blood lymphocytes, in an attempt to maximize the alloreactive responses against shared paternal and maternal MHC. A total of $9 \times 10^7$ and $2.3 \times 10^7$ viable nucleated cells/kg were infused four and five months after LAK cell infusion, respectively, one day after conditioning with cytoxan (500 mg/m$^2$ with forced hydration). Together with administration of in vitro alloactivated donor lymphocytes patients received home treatment with rIL-2, as before for three days ($6 \times 10^6$ IU/m$^2$/day), starting on the day of cell infusion. Treatment was followed by administration of $1.5 \times 10^6$ units of αIFN (Roferon A) three times weekly, with the goal in mind to upregulate cell surface antigens to render Ph-positive cells more antigenic. The level of Ph-positive cells dropped for the first time to 18%, then Ph-positive cells were no longer detectable and RT-PCR for bcr/abl remained consistently negative for >6 years. Since it was impossible to exclude the role of Roferon A in maintaining negative 46 XX t(9:22) cells and RT-PCR, the parents insisted to continue this treatment for four years. The patient has now remained in good health on no medications, off Roferon A, with a Karnofsky score of 100%, and is in complete molecular remission. The patient is fully reconstituted with donor male cells with no evidence of any residual female cells in the peripheral blood and in the bone marrow, with no clinical signs of chronic GVHD.

Immunotherapy with DLI and rIL-2. DLI was initiated by infusion with graded increments of donor PBL as previously described. Donor PBL and subsequently donor lymphocytes activated in vitro with rIL-2 were combined with in vivo administration of rIL-2, as previously described in details. Briefly, donor PBLs were precultured for 4 days with rIL-2 (Chiron) at 6,000 IU/ml for four days in a humidified 5% $CO_2$ incubator at 37° C. and activated in vivo by administration of rIL-2 ($6 \times 10^6$ U/m$^2$/day subcutaneously, starting on the day of cell infusion) on an outpatient basis. Donor PBL was obtained by apheresis, using a Baxter CS-3000+ cell separator (Baxter, Deerfield, Ill.). Activation of cells following rIL-2 treatment in vivo and in vitro was previously confirmed by in vitro microcytotoxic activity using chromium-labeled NK sensitive (K562) and NK-resistant (Daudi) target cells lines as previously described.

Activation of donor PBL against a mixture of parental PBL. Donor heparinized buffy coat cells (plasma+ interphase) were separated following centrifugation at 1,400 rpm for 15'. Cells were incubated in a semipermeable life-cell bag (Baxter) at a responder/stimulator ratio of 10:1, at final concentrations of $1.5 \times 10^6$ nucleated cells/ml cultured in phosphate buffered saline enriched with 10% donor plasma, Gentamicin 0.025% and penicillin 0.02%. Donor cells were cultured with a mixture of ficoll hypaque purified maternal and paternal blood lymphocytes, inactivated by ionizing irradiation (3,000 cGy). Cell culture was incubated for one day at a 37° C. incubator in 10% $CO_2$ in air, in an attempt to maximize the alloreactive responses against shared paternal and maternal MHC haplotype, presented by mismatched parental class II.

Assessment of response to cell therapy. The effect of cell therapy on relapse was assessed by hematologic evaluation of disease-specific parameters, including blood and bone marrow morphology, t(9:22) translocation by standard cytogenetic analysis and using RT-PCR.

Molecular analysis of minimal residual disease. Engraftment was confirmed by detection of male cells by PCR using the amelogenine gene located on both the X-chromosome with its shorter copy on the Y-chromosome, as described previously.

Patient Number 2: MS, a 12 year old child.
Diagnosis: CALLA-positive ALL.

This child with CALLA-positive ALL in $2^{nd}$ CR was following recurrent central nervous system relapses. The patient showed no evidence of GVHD following transplantation. The patient developed recurrent isolated recurrent central nervous system (CNS) relapse but was in excellent general condition with Karnofsky 100%. Due to the fact that relapses could not be prevented despite continuous systemic and intrathecal donor lymphocyte infusion (DLI) using the same donor (in this case a matched sibling), including DLI with rIL-2, since no GVHD could be induced, nor relapse of CNS prevented, it was decided to attempt to apply adoptive alloCT by activation of donor lymphocytes with parental alloantigens in an attempt to amplify tumor responses against parental alloantigens present on tumor cells of host origin.

Two different sets of cell cultures were considered the first involving donor cells as responders (such cells were not expected to be rejected since hosts reconstituted with donor cells were per definition tolerant of donor alloantigens. The second set of lymphocyte cultures were installed to induce additional responses against host alloantigens, induced by alloreactive half-matched maternal and paternal lymphocytes acting as responders, realizing that such alloreactive cells would only result in short-acting one-hit against host alloantigens, possibly tumor cells as well, since they were expected to be rejected by the patient. The donor cells were stimulated against both lymphocytes obtained from the father and from the mother to obtain reactivity against antigens present in the father and mother, respectively, in order to induce alloreactivity against antigens shared by the more and the father on the child's tumor cells.

As to allogeneic cell therapy with donor cells (expected durable immunotherapy since donor cells are not expected to be rejected) peripheral blood lymphocytes were obtained from his HLA matched sibling as well as both parents. Patient was treated by sibling (donor) blood lymphocytes reacting in one way mixed lymphocyte culture (MLC) against irradiated maternal or paternal alloantigens, in two separate sets of cultures (one culture was donor against the mother and the other culture was donor against the mother's cells) for approximately six days, in an attempt to induce alloreactivity against shared maternal and paternal alloantigens represented on the cell surface of the patient's tumor cells.

As far as alloCT with haploidentically mismatched parental lymphocytes (expected short duration "one hit" only), the patient received maternal and paternal peripheral blood lymphocytes activated in one way MLC against irradiated donor lymphocytes (sharing MHC with the patient), in an attempt to induce proliferative responses against maternal and paternal alloantigens represented by patient's tumor cells. The second sets of cell infusions were given following an attempt to upregulate cell surface MHC expression of patient's tumor cells by in vivo administration of two daily injections of alpha-interferon (Roferon-A) $3\times10^6$ units subcutaneously. The number of cells infused were $2.6\times10^7$ nucleated cells/kg. Three months later the number of cells infused were $4.7\times10^7$ nucleated cells/kg (both infusions were uneventful). The patient is in excellent general condition with a Karnofsky score of 100%, with no evidence of systemic or CNS disease. No signs of GVHD developed. The patient is currently alive and well with no macroscopic evidence of disease and is still under observation.

3. ADOPTIVE ALLOGENEIC CELL THERAPY WITH MISMATCHED LYMPHOCYTES ACTIVATED AGAINST HOST-SPECIFIC TUMOR CELLS

Patient Number 1: DB, 72 year old male
Diagnosis: Glioblastoma of brain.

Diagnosis was made due to headaches, changes in personality and sense of instability in space. The patient underwent surgical excision of a 5 cm brain tumor with local administration of BCNU (also known as carmustine). One month later field radiation was administered for the next two months (5,000 cGy involved field irradiation). Treatment was given under cover of Dexamethasone and anticonvulsive therapy (Dilantin 500 mg daily). Due to suspected deep vein thrombosis the patient received low molecular weight heparin subcutaneously daily. Due to marked external fluid accumulation at the surgical site with bulging of the skull over the surgical wound, a shunt was placed to drain CNS fluid. Copy of brain MRI film brought with the patient upon arrival to Israel, completed one day before departure, revealed post surgical evidence of ependymal spread, especially in the lateral chambers. By comparison with earlier MRI scans done in the United States, a suspicion was raised of tumor progression at the borders of the surgical cut with possible progression caudally. Considering the poor prognosis of this disease presented as such a large mass, after discussing the case with an experienced neurosurgeon of the Division of Neurology at the Evanston Hospital in Chicago and considering the lack of any previous success with patients at his age with this disease, it was decided to proceed with an experimental allogeneic cell therapy program despite the lack of previous experience in treating glioblastoma.

Peripheral blood mononuclear cells were obtained from his haploidentically-mismatched daughter. A total of $1.5\times10^7$/nucleated cells/kg LAK cells were infused, together with daughter's spontaneous lymphocytes precultured in vitro with irradiated tumor cell suspension. Mixed lymphocyte tumor cultures were carried out using tumor material cryopreserved during surgery. Tumor cell suspension was irradiated 24,000 cGy prior to culturing for total inactivation of tumor cells. A total of $2.6\times10^7$/kg additional peripheral blood mononuclear cells were infused on the same day to maximize the number of anti-cancer effector cells to be subsequently activated in vivo with rIL-2. Overall, treatment was uneventful. Concomitantly with administration of rIL-2, patient complained of fatigue and fever which did Tylenol control. Lower doses of were considered subsequently ($3\times10^6$ IU daily) to avoid possible central nervous system toxicity. No signs of GVHD developed.

The patient is currently receiving Temodal (alkylating agent in an attempt to further control minimal residual disease. The patient is in excellent general condition with a Kamofsky score of 100%, asymptomatic, and back home in the United States. He is alive and well, back to work and will receive additional treatment from matched unrelated donors.

Patient Number 2: AE a 14 Year Old Male

This patient with resistant relapsed ALL originally underwent allogeneic bone marrow transplantation from his fully matched HLA-A,B,C and DRB1 mother. The alloBMT procedure was uneventful but the patient developed no GVHD. He relapsed repeatedly following alloBMT and failed to respond to DLI but responded to conventional doses of chemotherapy.

Considering the fact that his mother was HLA identical with the patient and would not be expected to respond well in vitro against his HLA matched tumor cells, we have treated the patient with a 4-way alloCT protocol:

First, it was important to maximize "tumor specific" responses by allogeneic lymphocytes using a mixed lymphocyte-tumor culture system. In order to activate killer cells against tumor-specific or tumor associated antigens in the context of patient's MHC, to maximize their potential anti-tumor effects, paternal peripheral blood lymphocytes were alloactivated against patient's blast tumor cells (inactivated by 24,000 cGy). A similar mixed lymphocyte-tumor cell culture was set against patient's blasts as stimulators, using sibling's peripheral blood lymphocytes, thus expressing immunogenic maternal haplotype, as responders.

Two additional cell culture systems were set to induce allogeneic responses against paternal and maternal alloantigens expressed on patient's tumor cells (the two separate cultures were injected separately to avoid any possible reactivity):

1) Maternal peripheral blood lymphocyte alloactivated against irradiated paternal lymphocytes to elicit alloreactivity against paternal alloantigens expressed by patient's tumor cells. Two separate cultures were cultured for approximately six days.

2) Maternal peripheral blood lymphocytes alloactivated against irradiated brother lymphocytes in order to elicit proliferative responses against stimulatory maternal alloantigens expressed by patient's tumor cells. Cell infusion was totally uneventful.

Cell infusion was uneventful. No signs of GVHD developed. This patient recently died from relapse before the patient was given another chance for additional cell therapy.

3. IMMUNOTHERAPY WITH MISMATCHED rIL-2 ACTIVATED LYMPHOCYTES TARGETED TO METASTACTIC SOLID TUMORS BY HUMANIZED TUMOR-SPECIFIC ANTIBODIES FOR INDUCTION OF ANTIBODY DEPENDENT CELL-MEDIATED CYTOTOXICITY (ADCC).

3.1 Immunotherapy in Conjunction with anti-HER 2/Neu (Herceptin)

Patient Number 1: NR, 45 Year Old Female
Diagnosis: Metastatic Breast Cancer

Breast cancer was diagnosed. Patient was treated with lumpectomy. Five out of 12 auxiliary lymph nodes were involved and patient was treated with 3 courses of Adriamycin and Taxol. The patient underwent high-dose chemotherapy supported by autologous stem cell transplantation six months after the lumpectomy.

Eight months later recurrence of disease was diagnosed with liver, lungs and bone metastases. The patient was treated with 5-FU and subsequently Taxol in combination with anti her2/Neu antibodies. Serological markers included Ca 15–3 223 U/ml (Ca 15-3 is an antigen that can be detected in primary or metastatic breast cancer patients; when the Ca 15-3 level is high, this usually means that the cancer recurred or the patient underwent relapse); and carcino embryonic antigen (CEA) 2.6 mg/ml. Patient did not respond to chemotherapy and her general condition was worsening, with consistent anemia and thrombocytopenia and the patient became blood transfusion dependent.

This patient was treated with the protocol. The dose of Herceptin infused was 2 mg/Kg (total dose 110 mg). Total number of rIL-2 activated lymphocytes obtained from her haploidentically mismatched sister was $10^7$ nucleated cells/Kg. In parallel, patient received Eprex (recombinant human erythropoietin) and Neupogen (granulocyte-colony stimulating factor or "G-CSF") (not part of the protocol) due to pancytopenia. The procedure was uneventful except for mild fever and tremor which accompanied the cell infusion, but it was transient and discontinued as soon as the infusion was over. No signs of GVHD developed.

Patient received no subsequent chemotherapy. Patient received a second dose of peripheral blood lymphocytes isolated from another haploidentically-mismatched sister $4.73 \times 10^7$/Kg and a similar dose of anti-her2/Neu antibodies. In the interim period, no additional chemotherapy was given. Hemoglobin, white blood cells and platelets increased gradually, and the patient felt better then during the pre-treatment period.

Ten months later, the patient complained of headache and MRI scan done for the first time revealed meningeal spread. It should be noted that Herceptin does not cross the blood brain barrier. Until that point in time, tumor cell markers declined with a minimum level of CA15.3 of 41 U/ml; carcino-embryonic antigen ("CEA") 1.4 mg/ml and TPS 237 u/L (another antigen that can be used as a marker or indicator for the presence of tumor cells). Currently, the patient is deteriorating, due to meningeal spread. Overall, the response rated was evaluated as partial response (however, at this point in time, it was difficult to assess the contribution of prior therapy with Taxol as compared with the net effects of the alloCT program administered later). This patient received no r-IL2 immunosuppression and no interferon due to her poor performing status.

Patient Number 2: GS, 58 year old female
Diagnosis: Metastatic breast cancer

This patient was diagnosed with breast cancer. Histological evaluation of the mass revealed infiltrating ductal carcinoma with 15 of 34 lymph nodes with evidence of disease. Patient was treated with modified radical mastectomy and CAF chemotherapy followed by Tamoxifen hormonal therapy. Patient underwent high-dose chemotherapy supported by autologous stem cell transplantation with uneventful recovery. Pulmonary metastases were noted two years later. Patient received treatment with 5-FU, Taxotere & Novalbin and involved field radiation. Subsequently, to delay metastatic spread, recombinant interleukin 2 and alpha interferon was administered as home treatment. Review of the biopsy revealed positive HER-2/Neu, at which point in time it was decided to offer her alloCT in conjunction with HER-2/Neu. Patient was treated with Taxol and Herceptin nine months later on a weekly basis (total of 5 courses). Under treatment, serological markers deteriorated and patient felt worse. Patient was treated with additional cycles of Herceptin alone (three courses).

The alloCT course was done according to the scheme described. This time Herceptin was given prior to infusions of rIL-2 activated peripheral blood cells obtained from her haploidentically mismatched brother, a total of $2-10^7$ nucleated cells/Kg. A month later, the patient was treated with Herceptin, rIL-2 activated peripheral blood lymphocytes from another haploidentically mismatched brother, to a total of $2.52 \times 10$ nucleated cells/Kg, followed by five days of rIL-2 $6 \times 10^6$ IU/$m^2$.

Cell therapy was uneventful. Following alloCT, patient had transient decrease in serological markers of disease. Patient did not develop any clinical signs of GVHD and there was no evidence of engraftment of donor cells by VNTR-PCR. There appears to be no signs of tumor regression by CT scan, but her clinical condition remains excellent with a Kamofsky score of 100%.

3.2 Immunotherapy in conjunction with anti-CD20 Antibodies (MabThera)

Patient Number 1: FE, 41 year old male
Diagnosis: Non-Hodgkin's lymphoma B type, diffused large cell, stage IV A.

Patient was diagnosed following onset of cervical lymphadenopathy. Non-Hodgkin lymphoma diffused large cell type (B cell type) was diagnosed and the patient was treated with six courses of CHOP for five consecutive months. First remission was accomplished on after this five month treatment. First relapse was observed six months later, again with B symptoms (fever, pruruteus, weight loss, night sweats; in general terms, evidence for systemic manifestations of disease activity). Patient was treated with three courses of ESHAP for three consecutive months. Only partial response was accomplished and patient developed CNS involvement while on therapy. The patient then received high-dose chemotherapy supported with autologous stem cell transplantation due to resistant persistent disease. The post transplant course was uneventful, and following transplantation, there was no evidence of disease. Considering the high-risk status of the patient due to resistant disease, unlikely to be cured by autologous stem cell transplantation alone, it was decided to consider adjuvant immunotherapy with monoclonal anti-CD20 antibodies in conjunction with alloCT, using rIL-2 activated allogeneic lymphocytes. Patient received MabThera 500 mg intravenously followed by $2 \times 10^7$ nucleated cells/Kg obtained from his haploidentically-mismatched sister pre-cultured in vitro for 4 days with rIL-2 6,000 IU/ml. RT-PCR for BCL-2 remains normal. Both cycles of alloCT were followed with SC injections of r-IL2 $6\times10^6$ IU for five days. The alloCT program was uneventful. No signs of GVHD developed. A similar treatment was given again with MabThera 500 mg with $2.7\times10^7$ again with r-IL2 activated "LAK" cells/kg, again using his haploidentically-mismatched daughter. Again, treatment was uneventful and no signs of GVHD developed. Currently, the patient is back to normal life, with a Karnofsky score of 100% and no evidence of disease.

3.3 Immunotherapy in Conjunction with Monoclonal Antibodies Against Epithelial Cell Antigens (anti-17A, Panorex)

Patient Number 1: EC, 63 Year Old Male
Diagnosis: Colon and Renal Cell Cancer, Metastatic Involvement of Liver and Lungs The patient was diagnosed following acute intestinal obstruction. Following laparotomy and a tumor resection, right-sided liver metastases were noted. Characteristic serological markers included elevated CA 19.9 (a tumor marker that can be detected in the serum) and CEA and TPS. Due to 3 cm metastases in the right lobe of the liver, patient underwent right hemihepatectomy on January 1997. Subsequently, he received 5-FU for the next three months. six months later, following increase in serological markers, recurrent metastases were noted in the left lobe of the liver. Revision of CT scan revealed primary renal carcinoma in the right kidney. The patient underwent right heminephrectomy and excision of metastases from the left lobe of the liver one month later. Patient was treated with CPT 11 on a monthly basis for approximately ten months. At that time, under treatment with CPT 11, two new metastatic lesions were observed in the left lobe of the liver, and they were excised surgically with clean margins. The patient was then treated with alloCT in an attempt to control residual disease, with intraportal injection of rIL-2 activated peripheral blood lymphocytes obtained from his haploidentically mismatched son. Lymphocytes of the son were activated in vitro rIL-2 6,000 IU/ml for five days (patient was first treated with fludarabine as described above to delay cell rejection by the host). Following cell infusion, patient was treated with rIL-2 $6\times10^6$ IU/m$^2$ for five days subcutaneously. Patient received a total of $5\times10^7$ "LAK" cells/kg. The patient received 300 mg Panorex (anti-epithelial cell antibodies, anti-17A) followed by infusion of rIL-2 activated lymphocytes from his son. Cross match assay against blood lymphocytes from his son was negative. The treatment in both cases was uneventful and no signs of GVHD were noted. VNTR-PCR 30 days after cell infusion revealed a small degree mixed chimerism but no GVHD was observed. Mixed chimerism was transient, since another test done twenty days later did not reveal any traces of circulating donor DNA.

Two months later, a follow-up CT scan revealed multiple metastases in both lung fields, suggestive of renal cell cancer. Patient underwent bilateral thoracotomy and a total of nine metastases were removed. Histologically, there appeared to be a mixture of both colon and renal metastases with predominance of renal cell metastases. Patient was subsequently treated with 5-FU and combined with interferon and IL-2 on an outpatient basis. Four months later, the patient received Panorex 300 mg with LAK cells from his daughter 237 u/L, a total of $1.25\times10^7$/kg cells in the portal vein and $1.5\times10^7$/kg LAK cells systemically, followed by rIL-2 $6\times10^6$ IU/m$^2$ for five days. Cell infusion was uneventful, however, subsequent to rIL-2 therapy, patient gained weight (4 Kg) with some peripheral edema, which was ascribed to rIL-2. Subsequently, patient was maintained on alpha interferon $3\times10^6$ IU/m2 daily. Presently, the patient is in excellent clinical condition with a Kamofsky score of 100% with no evidence of disease.

3.4 Immunotherapy in Conjunction with Monoclonal anti-CEA Antibodies and rIL-2 Activated Donor Lymphocytes Patient Number 1: SY, 73 Year Old Male
Diagnosis: Metastatic Medullary Thyroid Cancer The patient was diagnosed following massive thyroid enlargement and cervical lymphadenopathy. Two years later, metastases were diagnosed in lungs, bones and liver. Patient was rapidly deteriorating. No chemotherapy was given. The level of anti-CEA was 138,000 ng/ml. Patient received humanized monoclonal anti-CEA antibodies 20 mg and one day later, LAK cells from his haploidentically mismatched son, a total of $3.4\times10^7$ nucleated cells/Kg. Treatment was uneventful. No signs of GVHD developed. Following treatment, patient improved dramatically, with improved general performance status, with better vitality. Edema, which was prominent in both ankles, disappeared. It should be noted that this was a high-risk patient, with active coronary artery disease, hypertension and diabetes mellitus in addition to diffuse metastatic spread of his basic malignancy. The patient remained under observation, and it appeared that progression of the disease stabilized mildly. Recently, the patent died although the treatment relieved his discomfort for as long as he was alive.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of delaying or preventing tumor growth in a host mammal comprising:
   (a) administering non-myeloablative irradiation to said host mammal;
   (b) administering allogeneic donor antigens selected from the group consisting of donor blood cells and donor bone marrow cells to said host mammal;
   (c) administering a non-myeloablative dose of lymphocytotoxic or tolerizing agent to said host mammal to selectively eliminate said host mammal's lymphocytes responding to said donor antigens;
   (d) administering allogeneic donor antigens derived from the same donor mammal as in step (b) selected from the group consisting of donor blood cells and donor bone marrow cells to said host mammal; wherein as a result of the second administration of donor blood cells or bone marrow cells, tumor growth is delayed or prevented.

2. The method of claim 1, wherein said tumor comprises neural cancer cells.

3. The method of claim 2, wherein said neural cancer cells are brain cancer cells.

4. The method of claim 3, wherein said brain cancer cells are glioblastoma cells.

5. The method of claim 1, wherein said tumor comprises cancer cells selected from the group consisting of breast cancer cells, gastrointestinal tract cancer cells, lung cancer cells, melanoma cells, renal cancer cells, genitourinary cancer cells, leukemia cells, and lymphoma cells.

6. The method of claim 1, wherein said non-myeloablative irradiation is selected from the group consisting of total lymphoid irradiation (TLI), and total body irradiation (TBI).

7. The method of claim 1, wherein said lymphocytotoxic agent is cyclophosphamide.

8. The method of claim 1, wherein (a) further comprises the administration of fludarabine.

9. A method of delaying or preventing tumor growth in a host mammal comprising:
   (a) administering non-myeloablative irradiation to said host mammal;
   (b) administering allogeneic donor antigens selected from the group consisting of donor blood cells and donor bone marrow cells to said host mammal;
   (c) administering a non-myeloablative dose of lymphocytotoxic or tolerizing agent to said host mammal to selectively eliminate said host mammal's lymphocytes responding to said donor antigens;
   (d) administering allogeneic donor lymphocytes derived from the same donor mammal as in step (b), which have been activated in vitro in the presence of interleukin-2, to said host mammal; wherein as a result of the administration of said allogeneic donor lymphocytes, tumor growth is delayed or prevented.

10. The method of claim 9, wherein said tumor comprises neural cancer cells.

11. The method of claim 10, wherein said neural cancer cells are brain cancer cells.

12. The method of claim 11, wherein said brain cancer cells are glioblastoma cells.

13. The method of claim 9, wherein said tumor comprises cancer cells selected from the group consisting of breast cancer cells, gastrointestinal tract cancer cells, lung cancer cells, melanoma cells, renal cancer cells, genitourinary cancer cells, leukemia cells, and lymphoma cells.

14. The method of claim 9, wherein said non-myeloablative irradiation is selected from the group consisting of total lymphoid irradiation (TLI), and total body irradiation (TBI).

15. The method of claim 9, wherein said lymphocytotoxic agent is cyclophosphamide.

16. The method of claim 9, wherein (a) further comprises the administration of fludarabine.

* * * * *